(12) United States Patent
Yamada et al.

(10) Patent No.: US 8,846,280 B2
(45) Date of Patent: Sep. 30, 2014

(54) COMPOUND, CHARGE TRANSPORTING FILM, PHOTOELECTRIC CONVERSION DEVICE, ELECTROPHOTOGRAPHIC PHOTORECEPTOR, PROCESS CARTRIDGE, AND IMAGE FORMING APPARATUS

(75) Inventors: Wataru Yamada, Kanagawa (JP); Katsumi Nukada, Kanagawa (JP); Yuko Iwadate, Kanagawa (JP); Tomoya Sasaki, Kanagawa (JP); Kenji Kajiwara, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 3 days.

(21) Appl. No.: 13/398,061

(22) Filed: Feb. 16, 2012

(65) Prior Publication Data
US 2013/0052571 A1    Feb. 28, 2013

(30) Foreign Application Priority Data

Aug. 22, 2011 (JP) ................. 2011-181013
Aug. 22, 2011 (JP) ................. 2011-181014

(51) Int. Cl.

| | |
|---|---|
| G03G 5/04 | (2006.01) |
| H01L 51/00 | (2006.01) |
| G03G 15/00 | (2006.01) |
| G03G 5/05 | (2006.01) |
| C07C 237/20 | (2006.01) |
| G03G 5/06 | (2006.01) |
| G03G 5/07 | (2006.01) |
| G03G 5/147 | (2006.01) |
| C07C 229/44 | (2006.01) |
| C07C 217/76 | (2006.01) |
| C07C 229/42 | (2006.01) |
| C07C 327/22 | (2006.01) |
| H01L 51/50 | (2006.01) |
| C07C 251/86 | (2006.01) |
| C07C 217/92 | (2006.01) |

(52) U.S. Cl.
CPC ............ *G03G 15/75* (2013.01); *C07C 2103/18* (2013.01); *H01L 51/5056* (2013.01); *G03G 5/0532* (2013.01); *H01L 51/0038* (2013.01); *G03G 5/0503* (2013.01); *C07C 2101/14* (2013.01); *C07C 251/86* (2013.01); *C07C 237/20* (2013.01); *H01L 51/0059* (2013.01); *H01L 51/0081* (2013.01); *G03G 5/0614* (2013.01); *G03G 5/071* (2013.01); *G03G 5/0592* (2013.01); *G03G 5/14791* (2013.01); *G03G 5/14795* (2013.01); *C07C 229/44* (2013.01); *C07C 217/76* (2013.01); *C07C 217/92* (2013.01); *G03G 5/14717* (2013.01); *G03G 5/0596* (2013.01); *C07C 229/42* (2013.01); *C07C 327/22* (2013.01)
USPC ....... 430/58.3; 430/58.75; 430/58.8; 564/433

(58) Field of Classification Search
USPC ..................... 564/433; 430/58.3, 58.75, 58.8
See application file for complete search history.

(56) References Cited

U.S. PATENT DOCUMENTS

| | | |
|---|---|---|
| 5,411,827 A | 5/1995 | Tamura et al. |
| 5,427,880 A | 6/1995 | Tamura et al. |
| 5,456,989 A | 10/1995 | Nogami et al. |
| 5,496,671 A | 3/1996 | Tamura et al. |
| 5,695,898 A | 12/1997 | Go et al. |
| 6,180,303 B1 * | 1/2001 | Uematsu et al. ............. 430/59.6 |
| 2002/0119382 A1 | 8/2002 | Nakata et al. |
| 2004/0043312 A1 | 3/2004 | Kikuchi et al. |
| 2005/0019684 A1 * | 1/2005 | Sekiya et al. ................. 430/66 |
| 2006/0160003 A1 | 7/2006 | Nagai et al. |
| 2007/0111121 A1 * | 5/2007 | Kikuchi et al. ............ 430/58.65 |
| 2007/0178400 A1 * | 8/2007 | Kikuchi et al. ............... 430/133 |
| 2011/0215303 A1 * | 9/2011 | Yamada et al. ................. 257/40 |
| 2011/0229809 A1 | 9/2011 | Nukada et al. |
| 2012/0189948 A1 | 7/2012 | Sonobe et al. |
| 2012/0196215 A1 | 8/2012 | Nukada et al. |

IR SPECTRUM OF CTM-39

FOREIGN PATENT DOCUMENTS

| | | |
|---|---|---|
| JP | A-62-251757 | 11/1987 |
| JP | A-05-040360 | 2/1993 |
| JP | A-05-216249 | 8/1993 |
| JP | A-07-072640 | 3/1995 |
| JP | A-07-146564 | 6/1995 |
| JP | B2-2546739 | 10/1996 |
| JP | B2-2852464 | 2/1999 |
| JP | A-2000-019749 | 1/2000 |
| JP | A-2000-066424 | 3/2000 |
| JP | A-2000-206715 | 7/2000 |
| JP | A-2001-175016 | 6/2001 |
| JP | A-2002-082469 | 3/2002 |
| JP | B2-3287678 | 6/2002 |
| JP | A-2004-012986 | 1/2004 |
| JP | A-2004-240079 | 8/2004 |
| JP | A-2005-234546 | 9/2005 |
| JP | A-2006-084711 | 3/2006 |
| JP | A-2006-178285 | 7/2006 |
| JP | A-2007-156081 | 6/2007 |
| JP | B2-4115055 | 7/2008 |
| JP | B2-4115056 | 7/2008 |
| JP | B2-4136238 | 8/2008 |
| JP | A-2008-262232 | 10/2008 |
| JP | B2-4217360 | 1/2009 |
| JP | A-2011-070023 | 4/2011 |

OTHER PUBLICATIONS

U.S. Appl. No. 13/430,242, filed Mar. 26, 2012.
May 9, 2013 Office Action issued in U.S. Appl. No. 13/430,242.
Cui et al. "Covalent Self-Assembly Approach to Improvement of Interfacial OLED Anode/Hole Transport Layer Contacts," Polymer Mater Sci Eng 83,239, 2000, pp. 239-240.

* cited by examiner

*Primary Examiner* — Hoa V Le
(74) *Attorney, Agent, or Firm* — Oliff PLC

(57) ABSTRACT

Provided is a compound represented by the following General Formula (I):

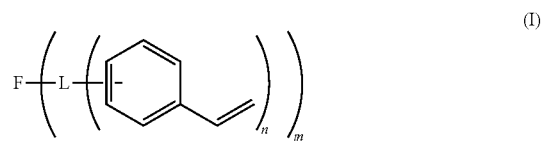

wherein in General Formula (I), F represents a charge transporting subunit, L represents a linking group having a valency of (n+1) that is formed by combining two or more kinds selected from a group consisting of an alkylene group, —C=C— (an alkenylene group), —C(=O)—, —N(R)—, —O—, and —S—, and R represents a hydrogen atom, an alkyl group, an aryl group, or an aralkyl group, m represents an integer of from 1 to 6, and n represents an integer of from 2 to 3.

15 Claims, 11 Drawing Sheets

COMPOUND, CHARGE TRANSPORTING FILM, PHOTOELECTRIC CONVERSION DEVICE, ELECTROPHOTOGRAPHIC PHOTORECEPTOR, PROCESS CARTRIDGE, AND IMAGE FORMING APPARATUS

CROSS-REFERENCE TO RELATED APPLICATIONS

This application is based on and claims priority under 35 USC 119 from Japanese Patent Application Nos. 2011-181013 and 2011-181014 both filed Aug. 22, 2011.

BACKGROUND

1. Technical Field

The present invention relates to a novel compound, a charge transporting film, a photoelectric conversion device, an electrophotographic photoreceptor, a process cartridge, and an image forming apparatus.

2. Related Art

In recent years, films (hereinafter, referred to as a "charge transporting film") using an organic compound and having a charge transport performance, which are used for electronic devices such as an electrophotographic photoreceptor, an organic EL device, an organic transistor, and an organic solar cell, are being actively developed.

SUMMARY

According to an aspect of the invention, there is provided a compound represented by the following General Formula (I).

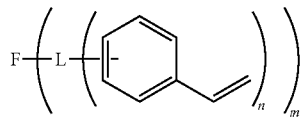
(I)

In General Formula (I), F represents a charge transporting subunit, L represents a linking group having a valency of (n+1) that is formed by combining two or more kinds selected from a group consisting of an alkylene group, —C=C— (an alkenylene group), —C(=O)—, —N(R)—, —O—, and —S—, and R represents a hydrogen atom, an alkyl group, an aryl group, or an aralkyl group. m represents an integer of from 1 to 6, and n represents an integer of from 2 to 3.

BRIEF DESCRIPTION OF THE DRAWINGS

Exemplary embodiments of the present invention will be described in detail based on the following figures, wherein.

DETAILED DESCRIPTION

[Novel Compound]

Figure 1:
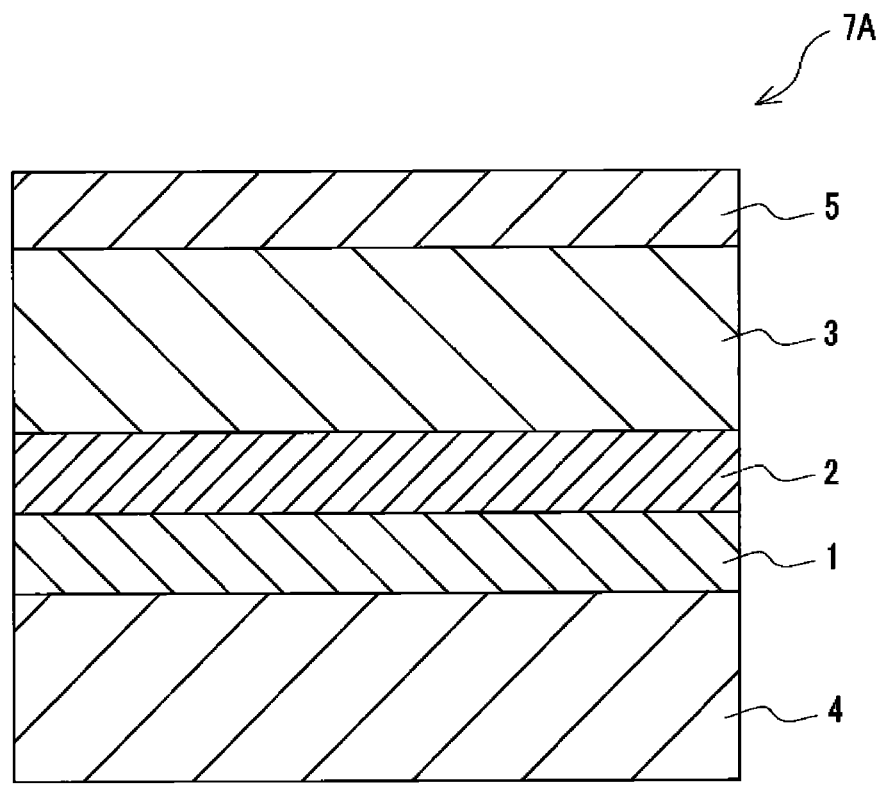
FIG. 1 is a schematic partial cross-sectional view showing an electrophotographic photoreceptor according to an exemplary embodiment.

The novel compound according to the exemplary embodiment is a compound represented by the following General Formula (I).

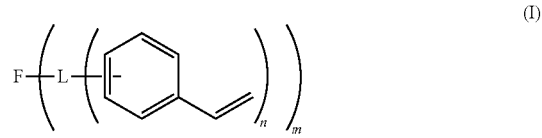
(I)

In General Formula (I), F represents a charge transporting subunit, L represents a linking group having a valency of (n+1) that is formed by combining two or more kinds selected from a group consisting of an alkylene group, —C=C—, —C(=O)—N(R)—O—, and —S—, and R represents a hydrogen atom, an alkyl group, an aryl group, or an aralkyl group. m represents an integer of from 1 to 6, and n represents an integer of from 2 to 3.

The charge transporting subunit represented by F in General Formula (I) is desirably a subunit derived from a compound having a charge transport performance, and specific examples thereof include subunits derived from compounds having a charge transport performance such as a phthalocyanine-based compound, a porphyrin-based compound, an azobenzene-based compound, a triarylamine-based compound, a benzidine-based compound, an arylalkane-based compound, an aryl-substituted ethylene-based compound, a stilbene-based compound, an anthracene-based compound, a hydrazone-based compound, a quinone-based compound, and a fluorenone-based compound.

Among these, a subunit derived from a triarylamine-based compound, which is excellent in terms of charge mobility and oxidation stability, is desirable.

Specific examples of the linking group having a valency of (n+1) that is represented by L in General Formula (I) include a trivalent or a tetravalent group that is formed by combining an alkylene group with a group selected from a group consisting of —C=C—, —C(=O)—N(R)—O—, and —S—.

More specifically, when the linking group is a trivalent group, the following groups are exemplified. In the following trivalent groups, "*" represents a site that is linked to F.

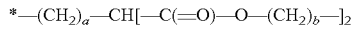

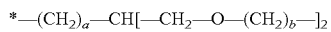

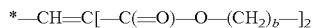

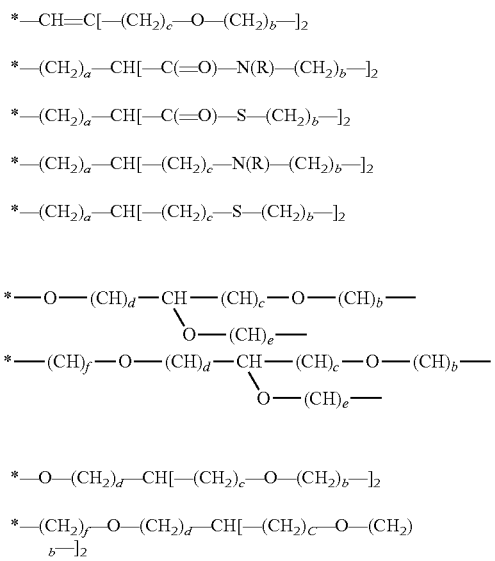

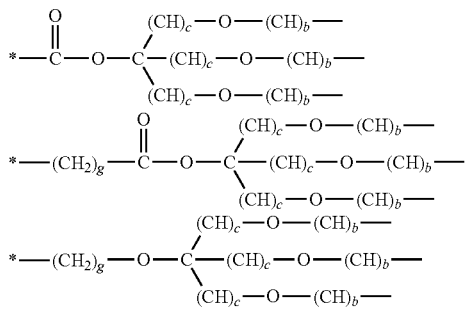

In the above trivalent linking groups, a, b, c, d, e, and f represent a repeating unit of a methylene group and an integer of from 1 to 10 (desirably from 1 to 4).

When L is a tetravalent linking group, the following groups are specifically exemplified. In the following tetravalent linking groups, "*" represents a site that is linked to F.

In the above tetravalent linking groups, b, c, and g represent a repeating unit of a methylene group and an integer of from 1 to 10 (desirably from 1 to 4).

In the linking group represented by L in General Formula (I), examples of the alkyl group represented by R of "—N(R)—" include a linear or branched alkyl group having from 1 to 10 (desirably from 1 to 5) carbon atoms. Specific examples of the alkyl group include a methyl group, an ethyl group, an n-propyl group, an isopropyl group, a butyl group, a t-butyl group, a pentyl group, and the like.

Examples of the aryl group represented by R of "—N(R)—" include an aryl group having from 6 to 20 (desirably from 6 to 12) carbon atoms, and specific examples thereof include a phenyl group, a toluoyl group, a xylyl group, a cumenyl group, a mesityl group, a naphthyl group, and the like.

Examples of the aralkyl group include an aralkyl group having from 7 to 20 (desirably from 7 to 14) carbon atoms, and specific examples thereof include a benzyl group, a phenethyl group, a phenylpropyl group, a naphthylmethyl group, a naphthylethyl group, and the like.

As the positional relationship between L and a vinyl group that bind to an aromatic ring in General Formula (I), a meta-position and a para-position are exemplified. There are plural aromatic rings in General Formula (I). However, in the positional relationship in which L and a vinyl group bind to each other in the plural aromatic rings, L and a vinyl group may bind to each other only in a meta-position or in a para-position, or L and a vinyl group may bind to each other in a meta-position and a para-position in combination.

In regard to solubility, the positional relationship of the combined type is desirable. In addition, in regard to manufacturability of a charge transport agent, since recrystallization enables purification in many cases, the positional relationship is established desirably only in a meta-position or a para-position, and particularly desirably in a para-position.

In General Formula (I), m is an integer of from 1 to 6. In order to improve the charge transport performance, m is desirably from 1 to 3, and in order to improve strength, m is desirably from 2 to 6.

As the novel compound according to the exemplary embodiment, a compound is particularly desirably exemplified which has a charge transporting subunit derived from a triarylamine-based compound as F in General Formula (I). Specifically, a compound represented by the following General Formula (II) is desirable.

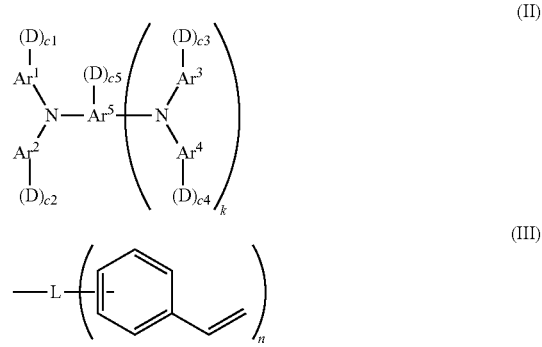

In General Formula (II), each of $Ar^1$ to $Ar^4$ independently represents a substituted or unsubstituted aryl group, $Ar^5$ represents a substituted or unsubstituted aryl group or a substituted or unsubstituted arylene group, and D represents a group represented by General Formula (III). k represents 0 or 1, each of c1 to c5 represents an integer of from 0 to 2, and all of c1 to c5 never become 0 at the same time.

In General Formula (III), L represents a linking group having a valency of (n+1) that is formed by combining two or more kinds selected from a group consisting of an alkylene group, —C═C—, —C(═O)—N(R)—, —O—, and —S—, and R represents a hydrogen atom, an alkyl group, an aryl group, or an aralkyl group. n represents an integer of from 2 to 3.

In General Formula (II), substituted or unsubstituted aryl groups represented by $Ar^1$ to $Ar^4$ may be the same as or different from each other.

Examples of a substituent in the substituted aryl group include an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom, other than "$(D)_C$".

$Ar^1$ to $Ar^4$ are desirably any one of the following Structural Formulae (1) to (7). The following Structural Formulae (1) to (7) in common exhibit "-$(D)_C$" which collectively represents "-$(D)_{C1}$" to "-$(D)_{C4}$" that may be linked to each of $Ar^1$ to $Ar^4$.

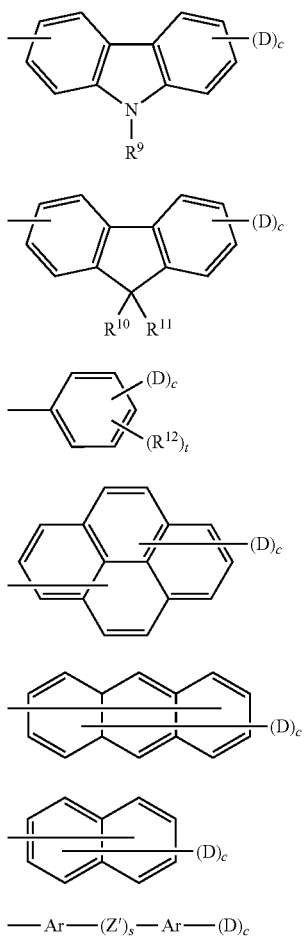

(1)
(2)
(3)
(4)
(5)
(6)
(7)

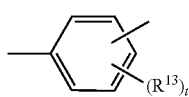

In Structural Formula (1), $R^9$ represents one kind selected from a group consisting of a hydrogen atom, an alkyl group having from 1 to 4 carbon atoms, a phenyl group substituted with an alkyl group having from 1 to 4 carbon atoms or with an alkoxy group having from 1 to 4 carbon atoms, an unsubstituted phenyl group, and an aralkyl group having from 7 to 10 carbon atoms.

In Structural Formulae (2) and (3), each of $R^{10}$ to $R^{12}$ independently represents one kind selected from a group consisting of a hydrogen atom, an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom. t represents an integer of from 1 to 3.

In Structural Formula (7), Ar represents a substituted or unsubstituted arylene group.

Ar in Structural Formula (7) is desirably represented by the following Structural Formula (8) or (9).

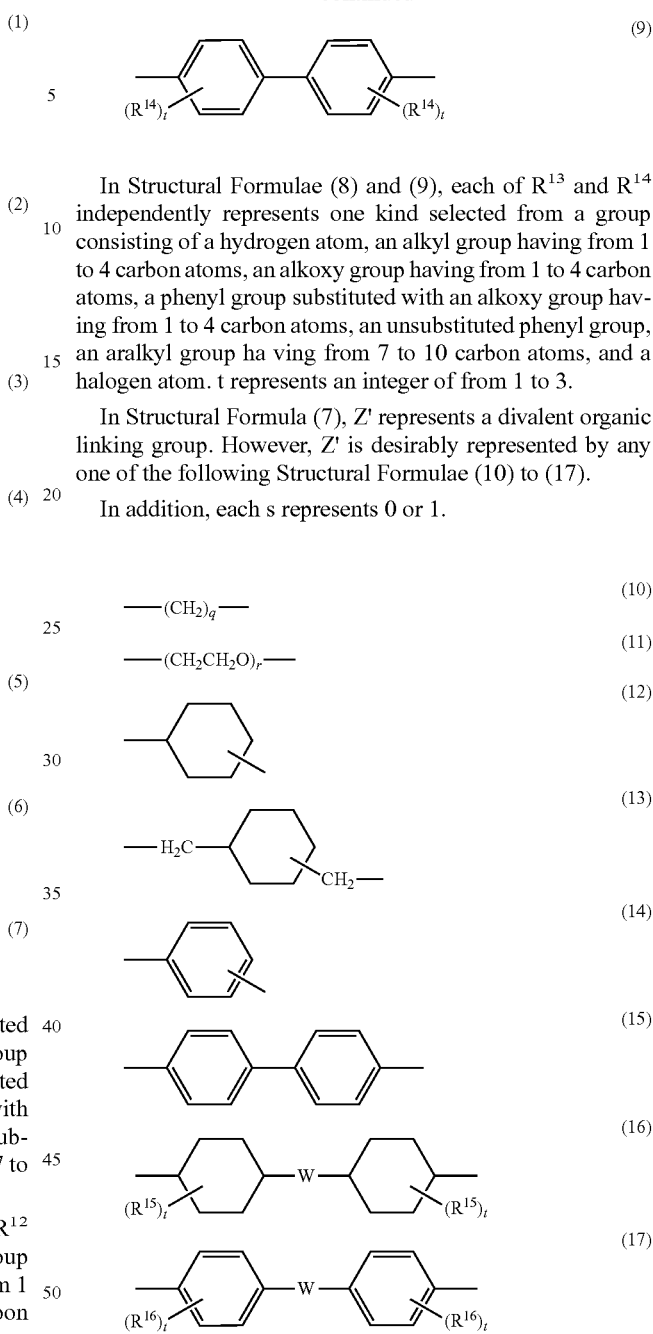

In Structural Formulae (8) and (9), each of $R^{13}$ and $R^{14}$ independently represents one kind selected from a group consisting of a hydrogen atom, an alkyl group having from 1 to 4 carbon atoms, an alkoxy group having from 1 to 4 carbon atoms, a phenyl group substituted with an alkoxy group having from 1 to 4 carbon atoms, an unsubstituted phenyl group, an aralkyl group having from 7 to 10 carbon atoms, and a halogen atom. t represents an integer of from 1 to 3.

In Structural Formula (7), Z' represents a divalent organic linking group. However, Z' is desirably represented by any one of the following Structural Formulae (10) to (17).

In addition, each s represents 0 or 1.

In Structural Formulae (10) to (17), each of $R^{15}$ and $R^{16}$ independently represents one kind selected from a group consisting of a hydrogen atom, an alkyl group having from 1 to 4 carbon atoms, a phenyl group substituted with an alkyl group having from 1 to 4 carbon atoms or with an alkoxy group having from 1 to 4 carbon atoms, an unsubstituted phenyl group, an aralkyl group having from 7 to 10 carbon atoms, and a halogen atom. W represents a divalent group, each of q and r independently represents an integer of from 1 to 10, and each t represents an integer of from 1 to 3.

W in Structural Formulae (16) and (17) is desirably any one of divalent groups represented by the following (18) to (26). Here, in Formula (25), u represents an integer of from 0 to 3.

—CH$_2$— (18)

—C(CH$_3$)$_2$— (19)

—O— (20)

—S— (21)

—C(CF$_3$)$_2$— (22)

—Si(CH$_3$)$_2$— (23)

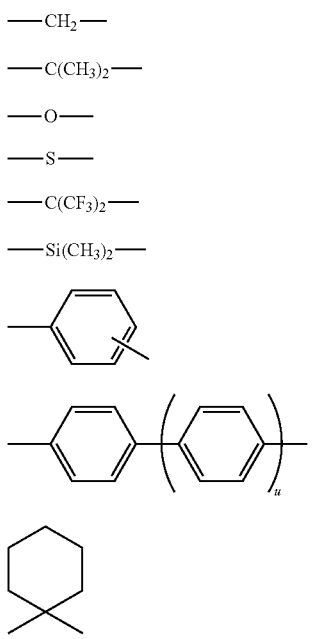

(24)

(25)

(26)

When k is 0, Ar$^5$ in General Formula (II) is a substituted or unsubstituted aryl group, and examples of the aryl group include the aryl group exemplified in the description for Ar$^1$ to Ar$^4$. When k is 1, Ar$^5$ is a substituted or unsubstituted arylene group, and examples of the arylene group include an arylene group obtained by removing one hydrogen atom from the aryl group exemplified in the description for Ar$^1$ to Ar$^4$.

In addition, examples of the substituent in the substituted arylene group include the same substituents as exemplified in the description for Ar$^1$ to Ar$^4$, which are substituents other than "D" in the substituted aryl group.

L in the group which is represented by General Formula (III) and is indicated by D in General Formula (II) has the same definition as L in the description for General Formula (I), and desirable examples thereof include the respective groups that were specifically exemplified.

Each of c1 to c5 in General Formula (III) represents an integer of from 0 to 2, and all of c1 to c5 never become 0 at the same time. In other words, the total number of D in General Formula (III) is 1 or greater, and the total number of D is desirably from 1 to 4.

Next, structures that are desirable as the following partial structure in General Formula (I) and the group represented by General Formula (III) will be described.

As the following partial structure and the group represented by General Formula (III), a group represented by the following General Formula (IV-1), a group represented by General Formula (IV-2), a group represented by General Formula (V-1), or a group represented by General Formula (V-2) is desirable in view of compatibility between electrical characteristics and the degree of curing.

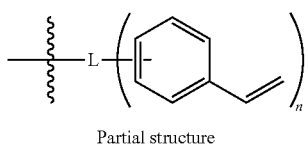

Partial structure

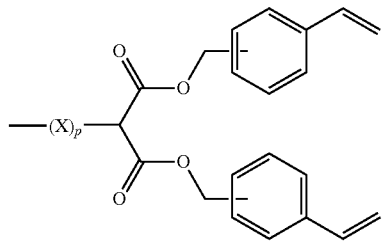

(IV-1)

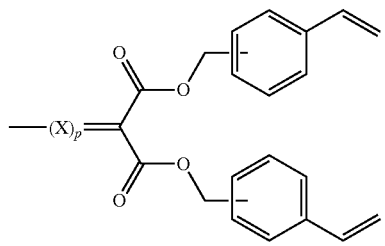

(IV-2)

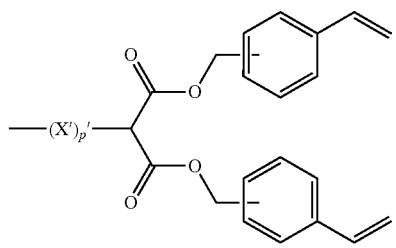

(V-1)

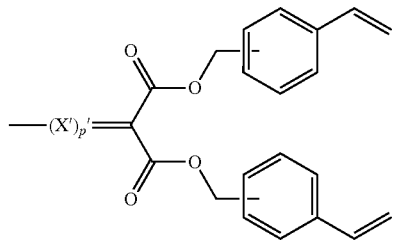

(V-2)

In General Formulae (IV-1) and (IV-2), X represents a linking group, and p represents 0 or 1.

In addition, in General Formulae (V-1) and (V-2), X' represents a linking group, and p' represents 0 or 1.

The wavy line in the above partial structure represents a site binding to the charge transporting subunit represented by F.

Examples of the linking group represented by X and X' include —CH=, an alkylene group having 1 or more carbon atoms, —C=C—, —C(=O)—, —N(R)—, —O—, —S—, and the like.

Hereinafter, specific examples of the compound represented by General Formula (I) will be shown, but the compound represented by General Formula (I) is not limited to the examples.

First, specific examples of the charge transporting subunit (skeleton excluding the partial structure) represented by F in General Formula (I) and specific examples of the partial structure (group represented by General Formula (III)) are exemplified. Subsequently, combinations of these examples are described in Table 1, and these are exemplified as specific examples (example compounds) of the compound represented by General Formula (I).

"*" in the following various specific examples indicates a linkage site. Herein, among example compounds described in Table 1, a compound No. CTM-1 is obtained by combining a specific example (described as "skeleton" in Table 1) (1)-1 of the charge transporting subunit represented by F with a specific example (III)-1 of the partial structure (group represented by General Formula (III), described as "functional group" in Table 1), and represents a compound linked via "*". Specifically, CTM-1 has the following structure.

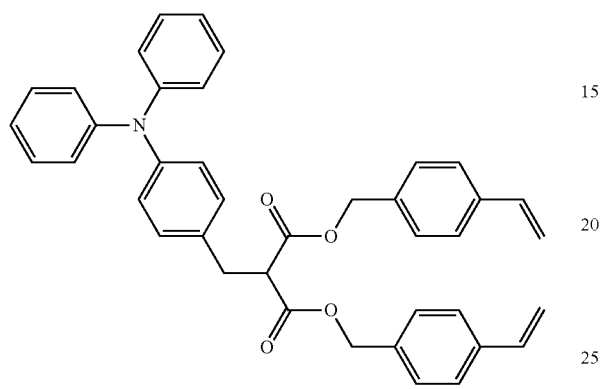

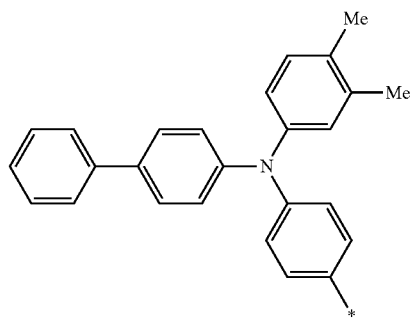
(1)-4

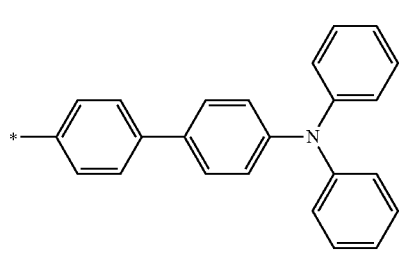
(1)-5

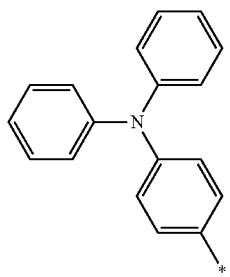
(1)-1

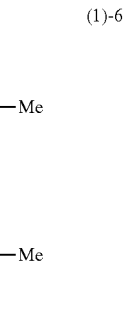
(1)-6

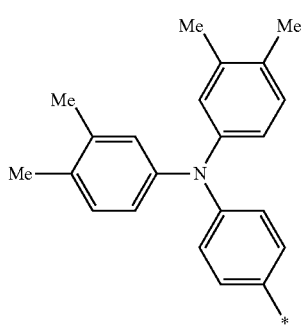
(1)-2

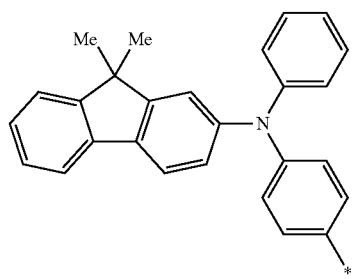
(1)-7

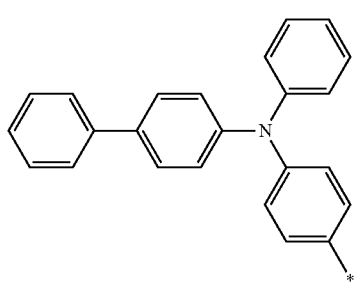
(1)-3

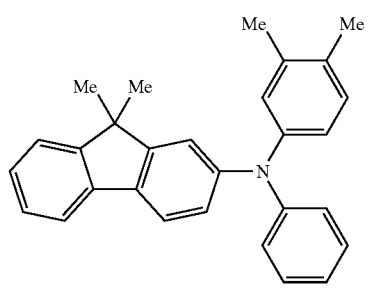
(1)-8

(1)-9
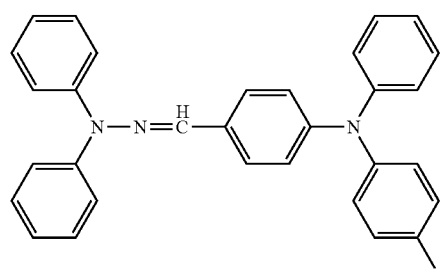
(1)-10
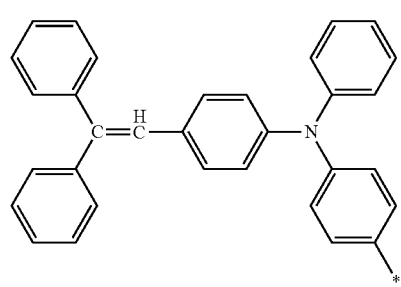
(1)-11
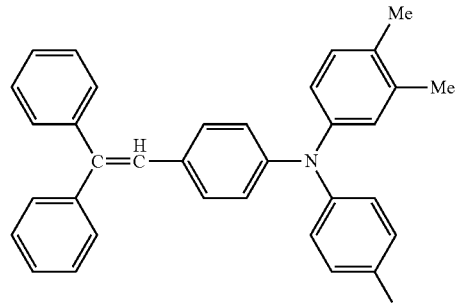
(1)-12
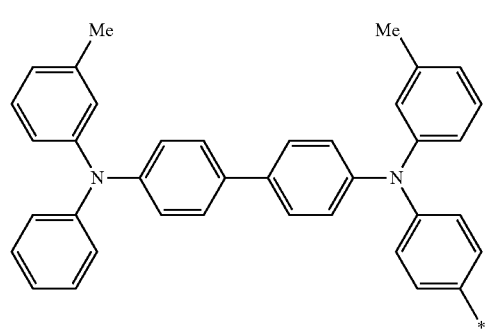
(1)-13
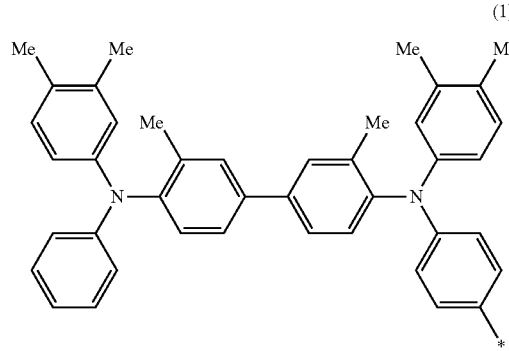
(1)-14
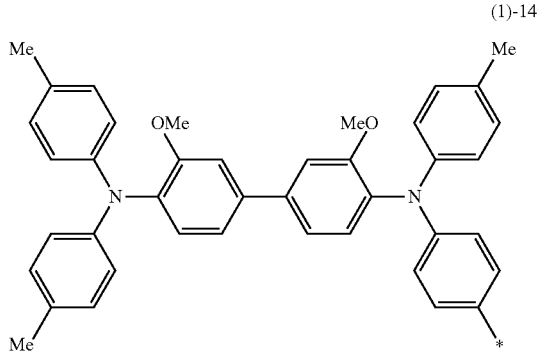
(1)-15
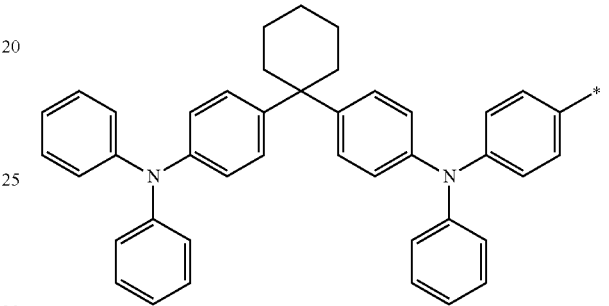
(1)-16
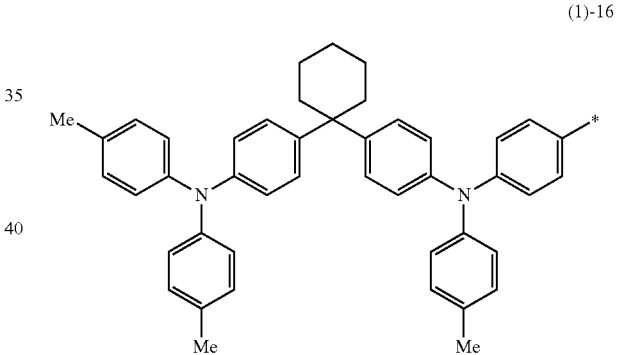
(1)-17
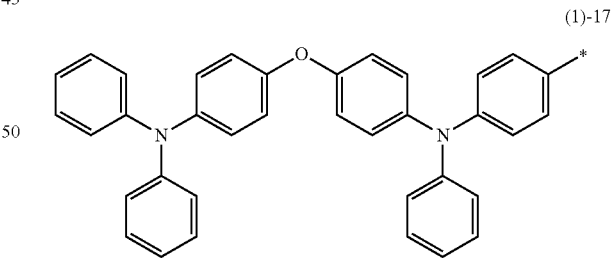
(1)-18
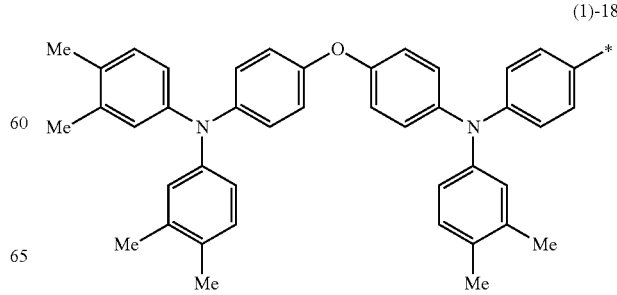

(1)-19
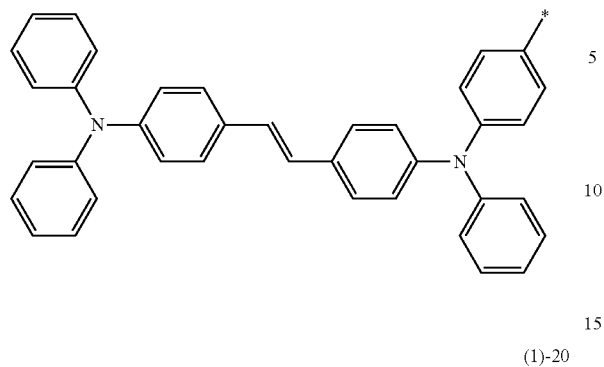
(1)-20
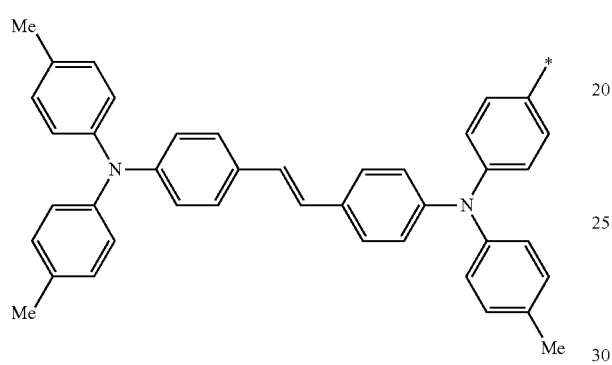
(1)-21
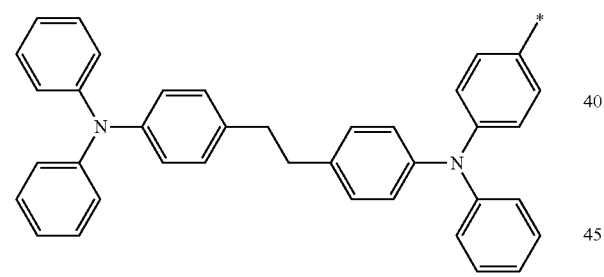
(1)-22
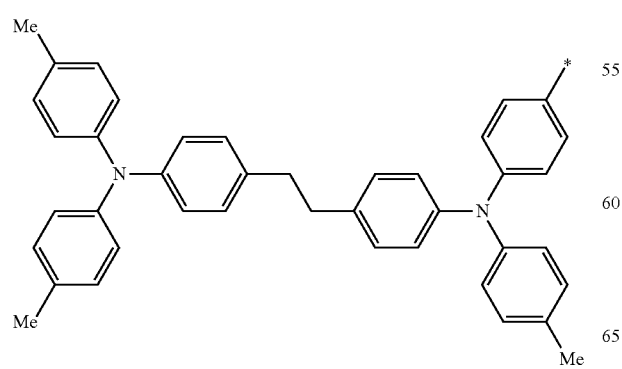
(2)-1
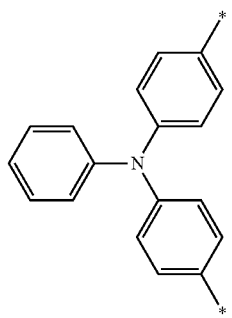
(2)-2
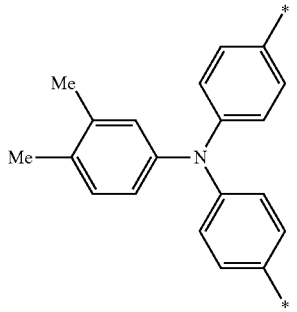
(2)-3
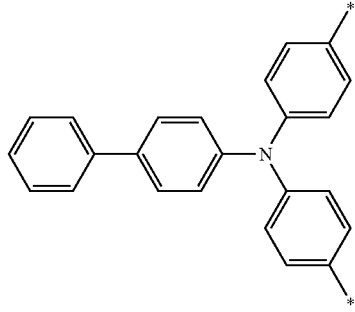
(2)-4
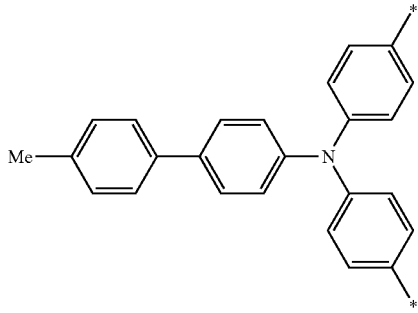
(2)-5
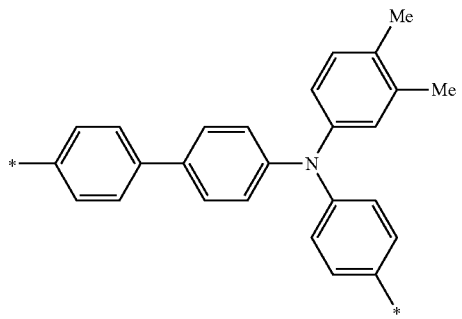

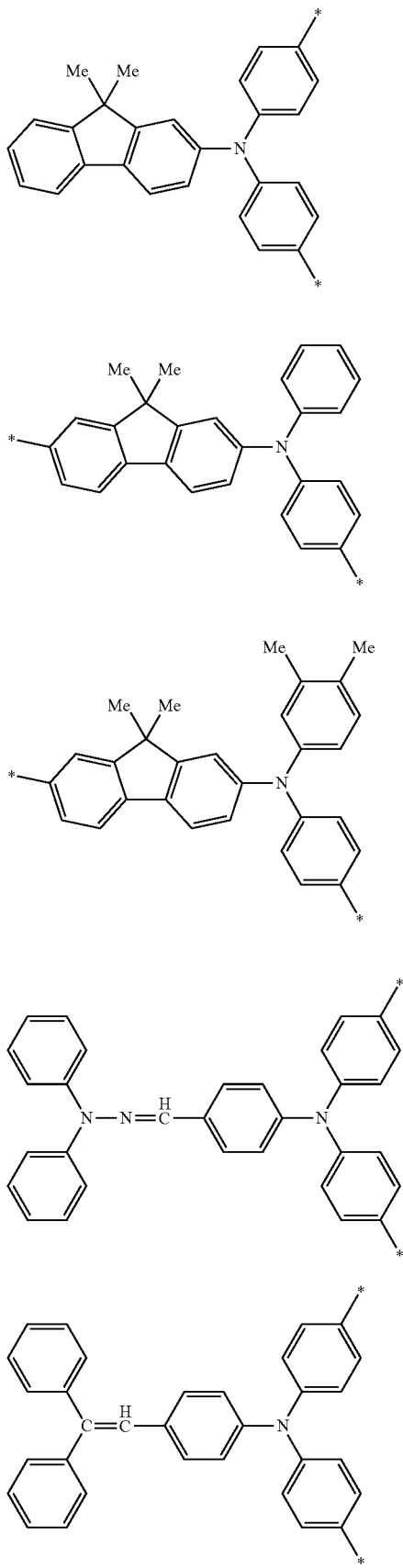
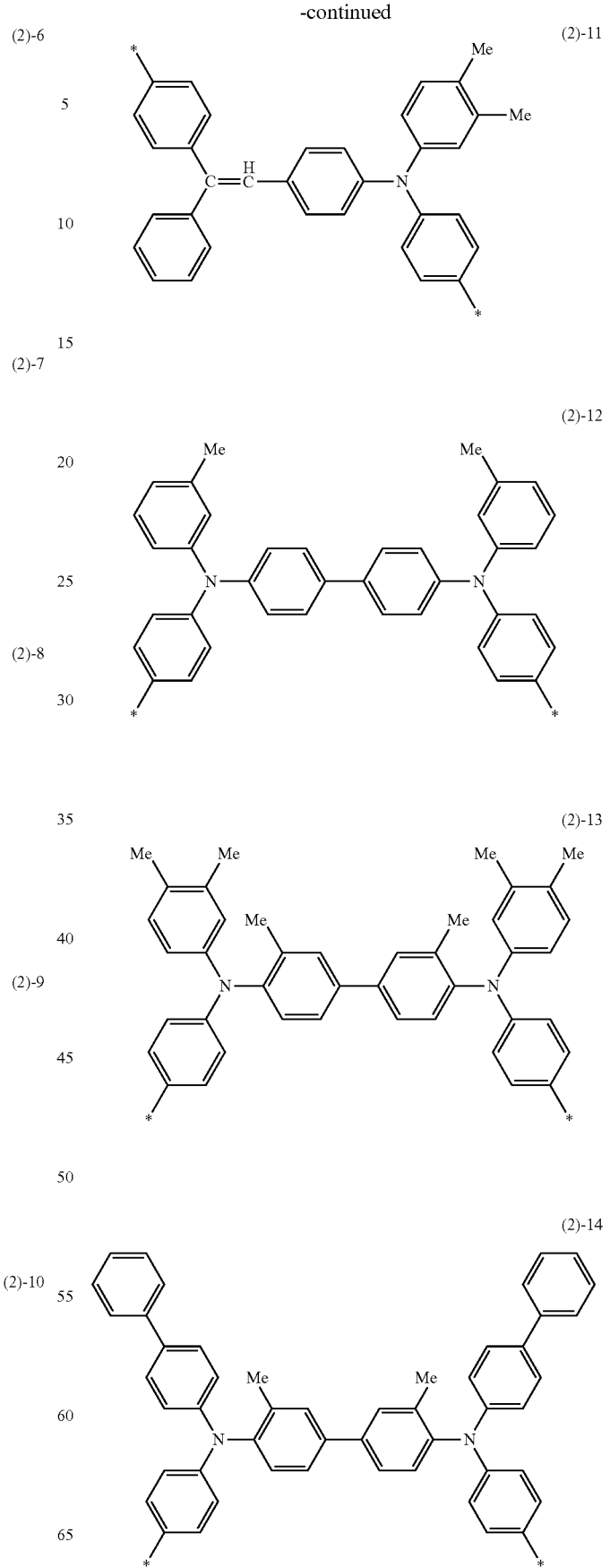

-continued
(2)-15
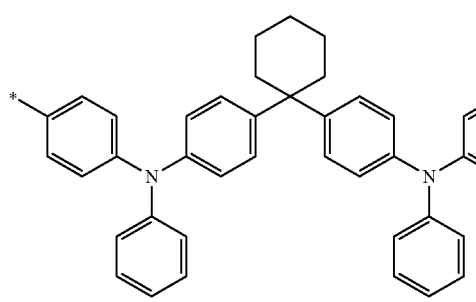
(2)-16
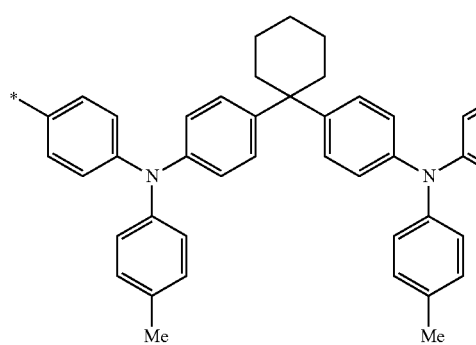
(2)-17
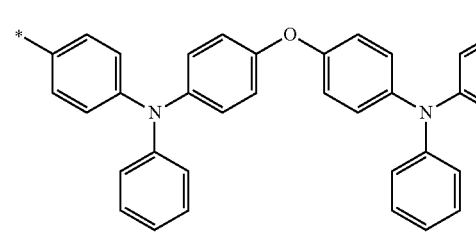
(2)-18
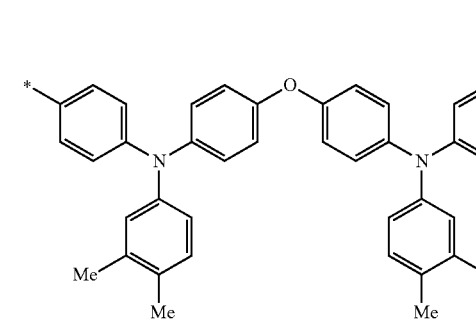
(2)-19
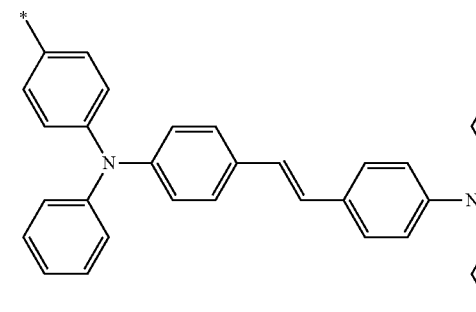
-continued
(2)-20
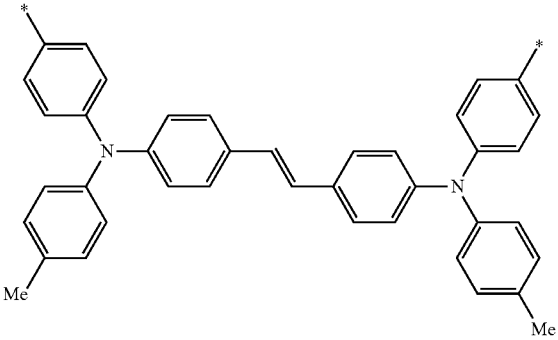
(2)-21
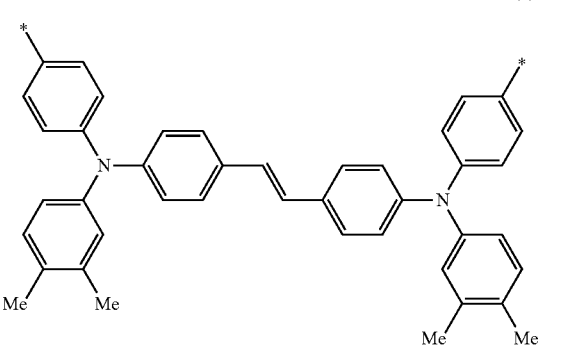
(2)-22
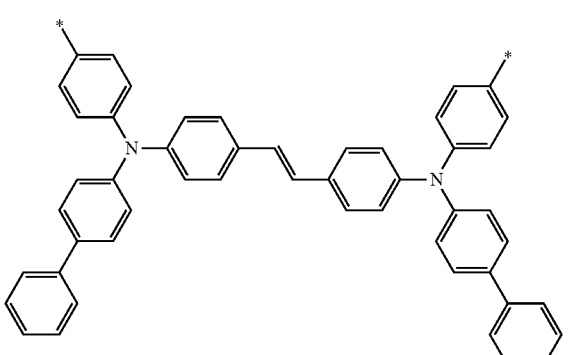
(2)-23
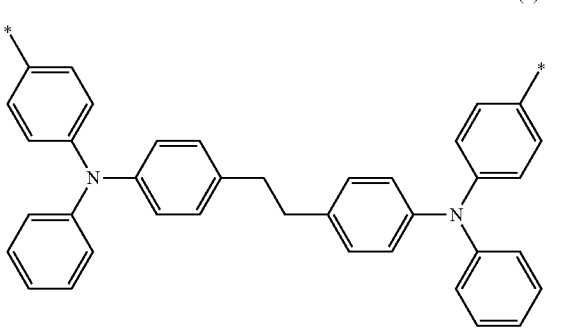

(2)-24
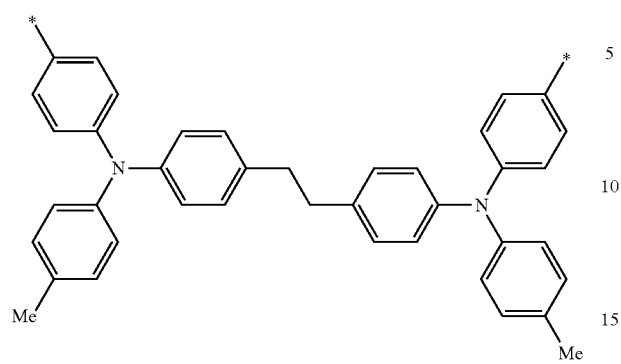
(2)-25
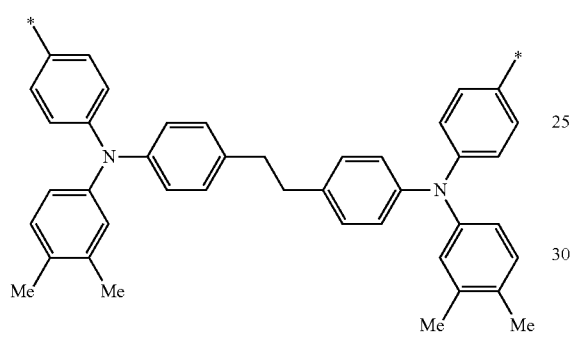
(2)-26
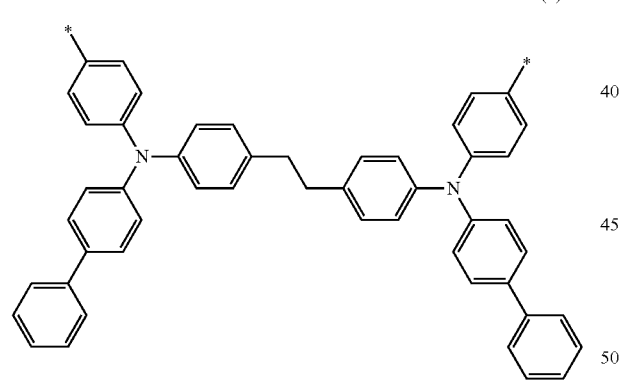
(3)-1
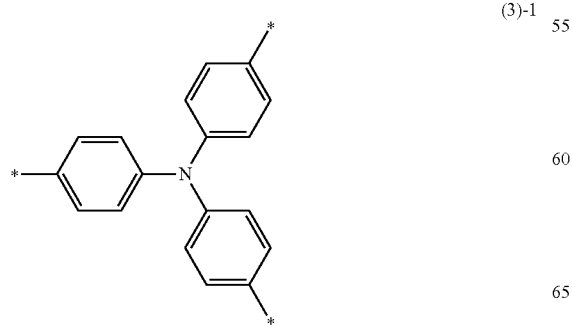
(3)-2
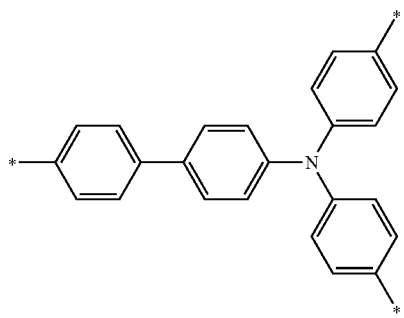
(3)-3
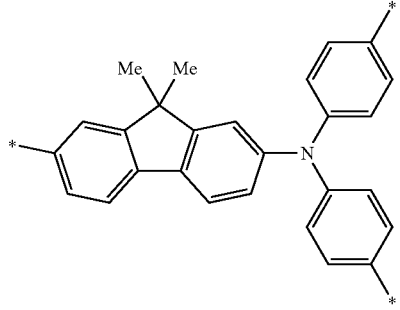
(3)-4
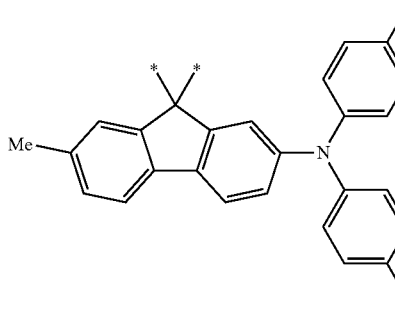
(3)-5
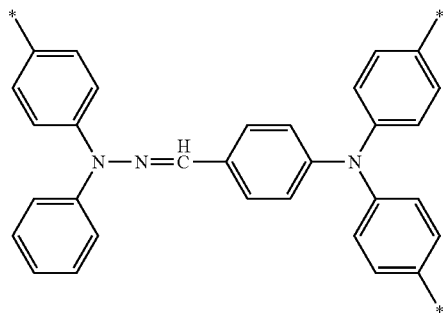
(3)-6
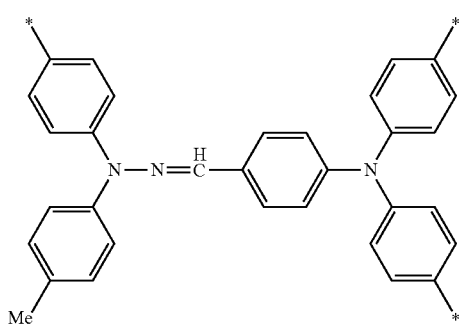

(3)-7
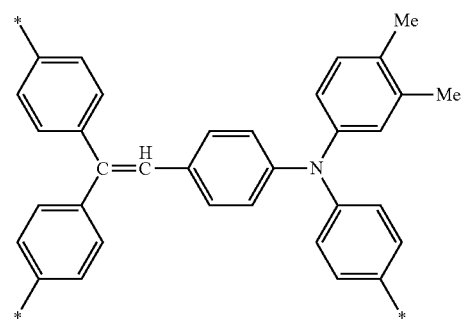
(3)-14
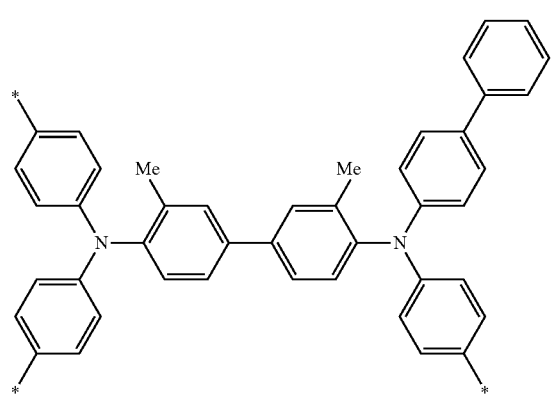
(3)-8
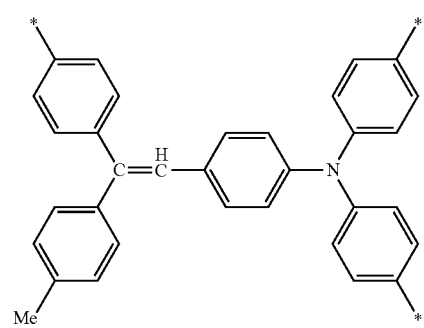
(3)-9
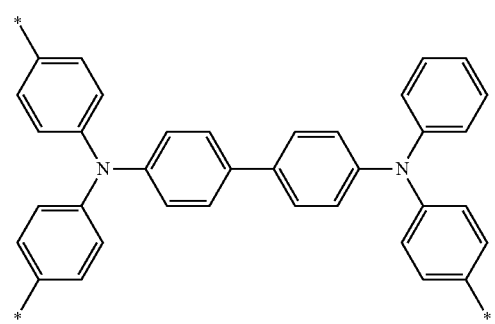
(3)-10
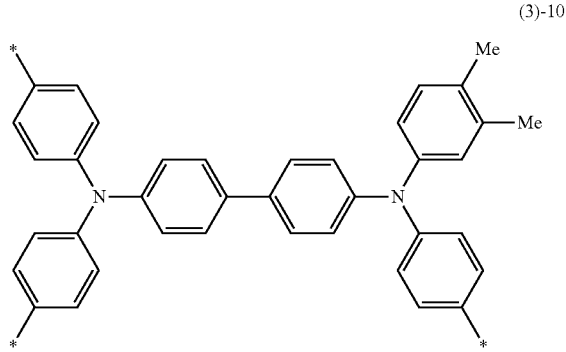
(3)-11
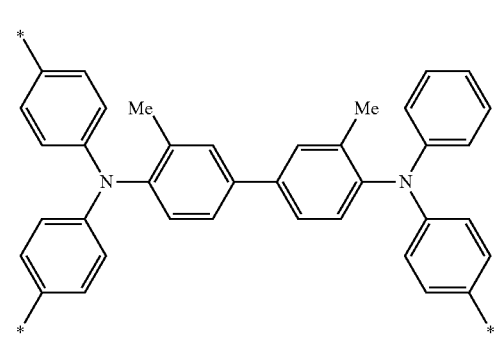
(3)-12
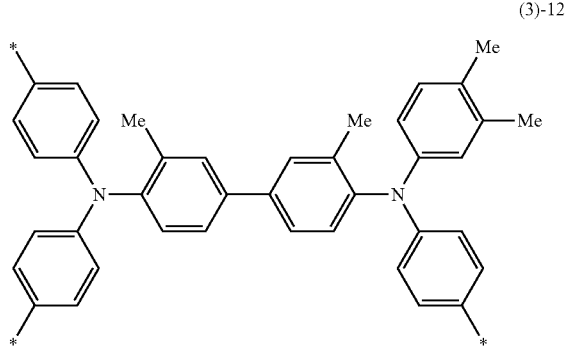
(3)-13
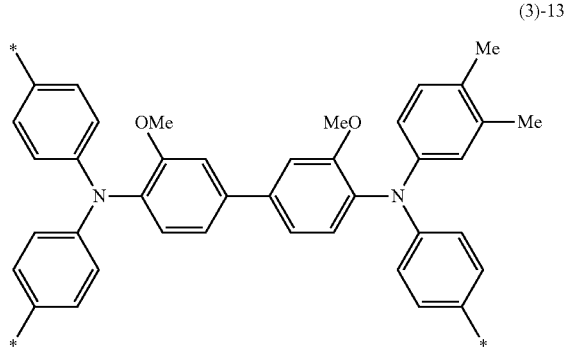

-continued
(3)-15
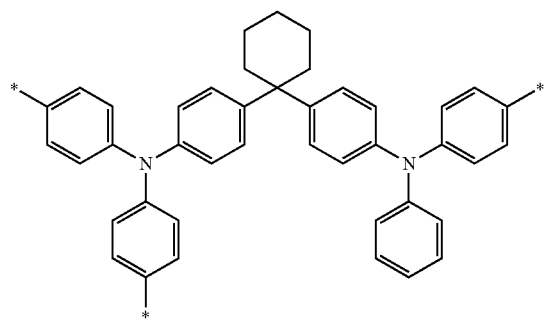
(3)-16
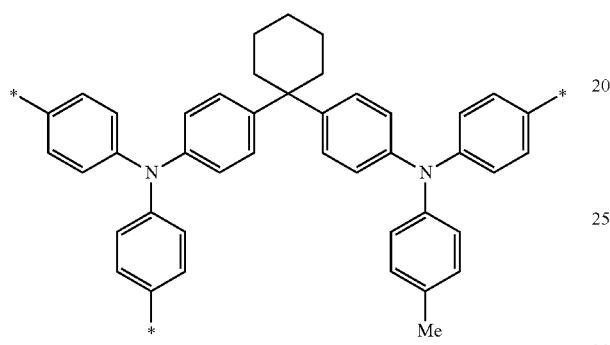
(3)-17
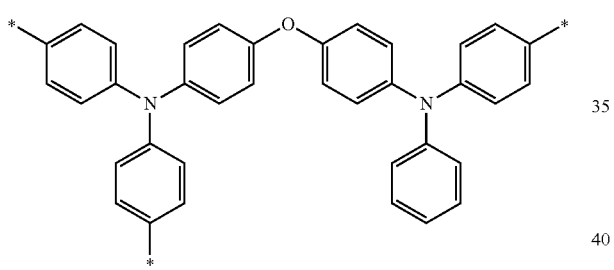
(3)-18
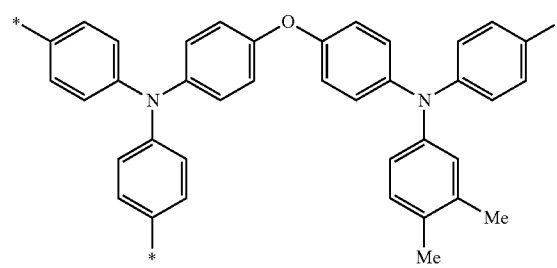
(3)-19
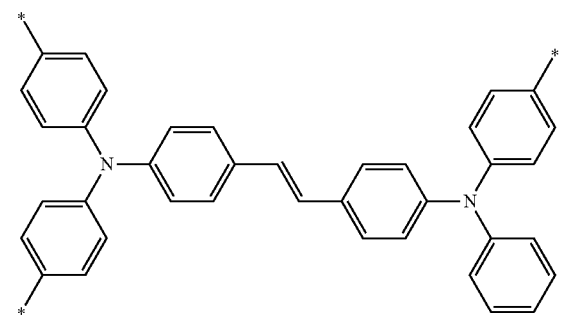
-continued
(3)-20
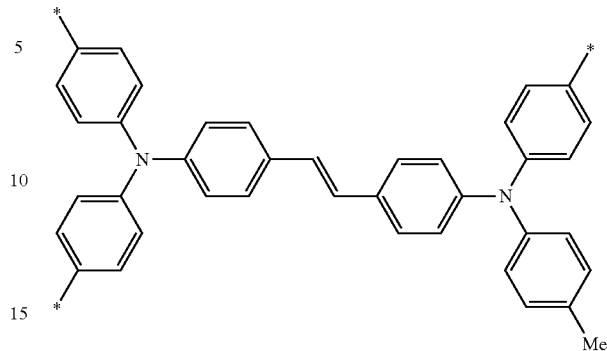
(3)-21
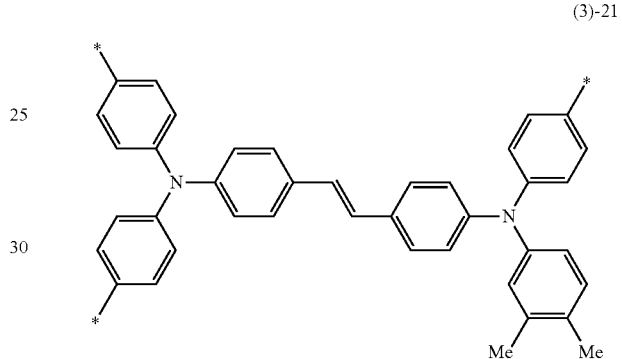
(3)-22
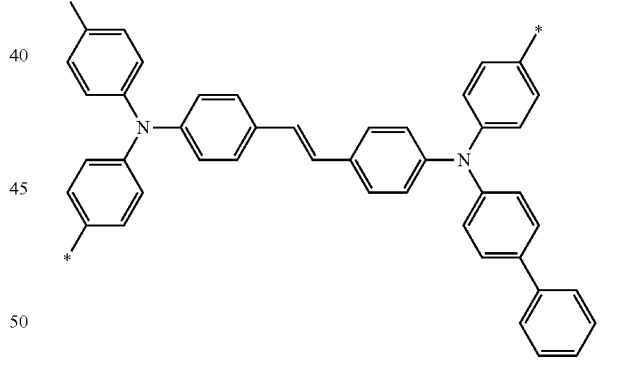
(3)-23

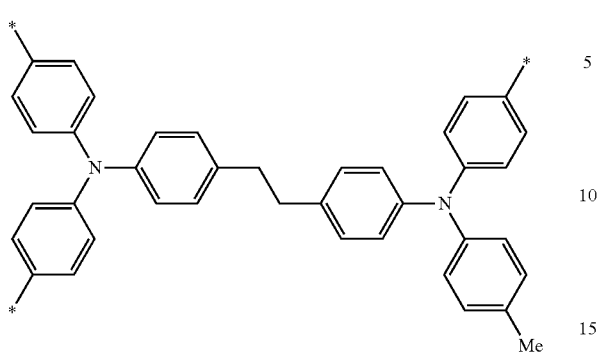
(3)-24
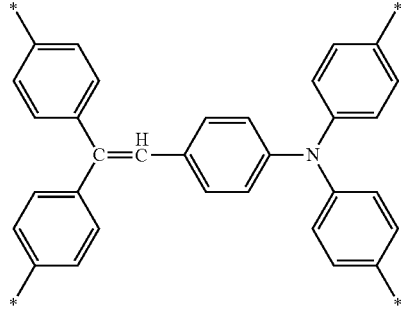
(4)-2
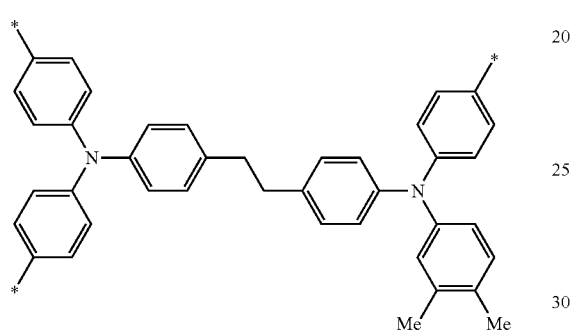
(3)-25
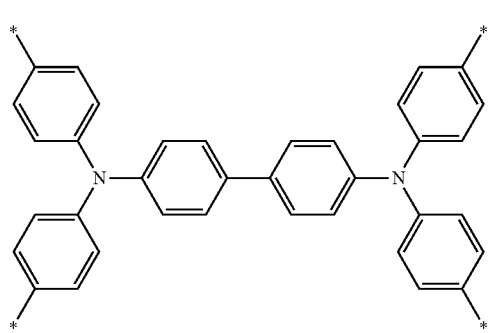
(4)-3
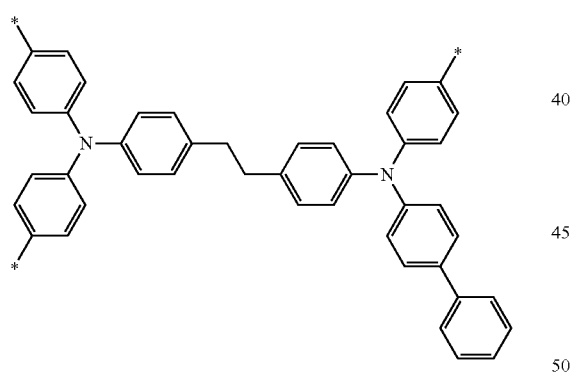
(3)-26
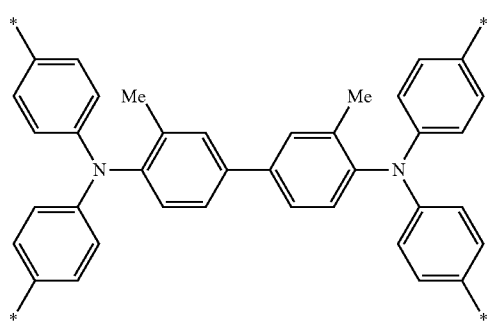
(4)-4
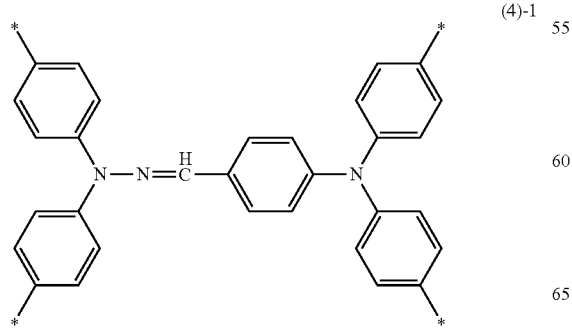
(4)-1
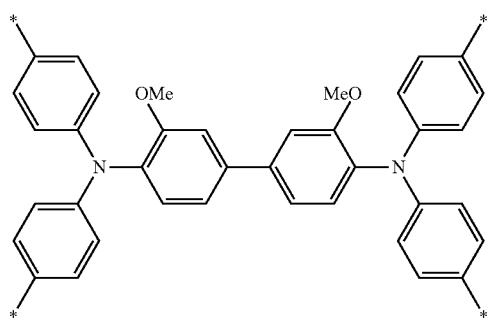
(4)-5

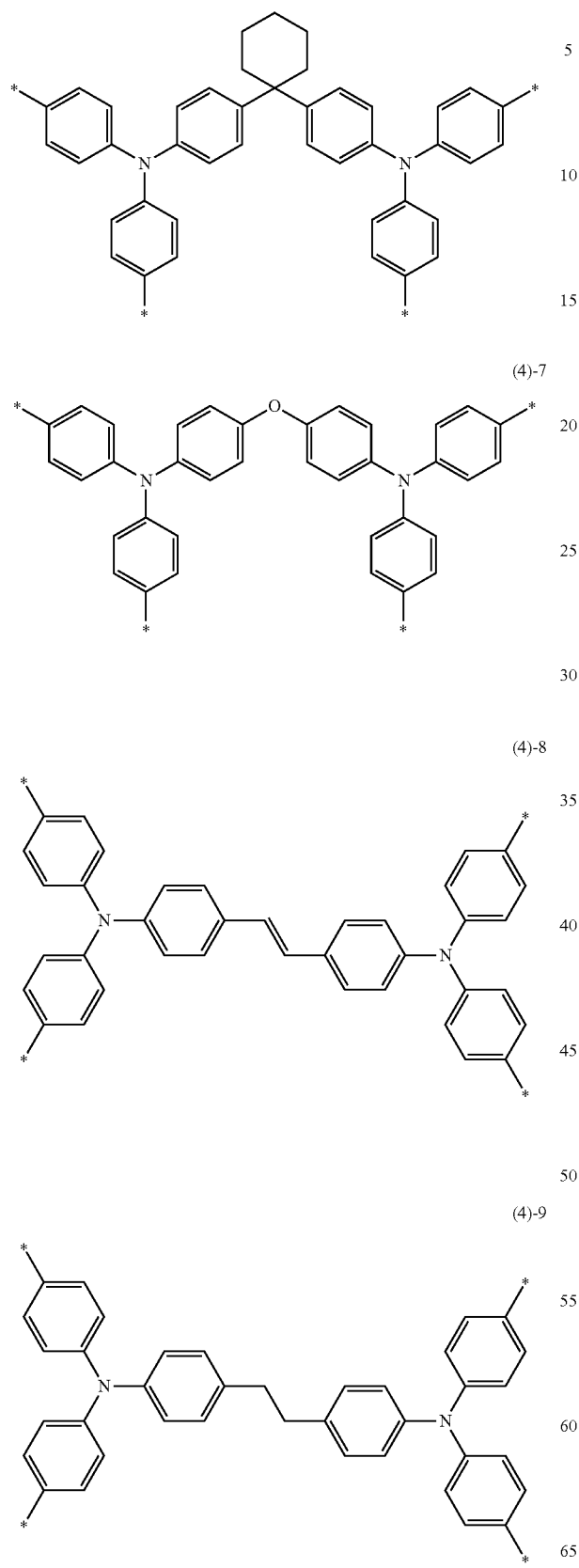
(4)-6
(4)-7
(4)-8
(4)-9
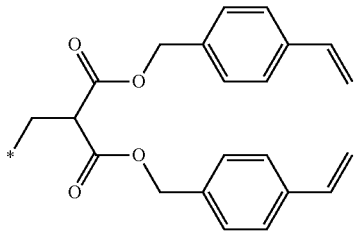
(III)-1
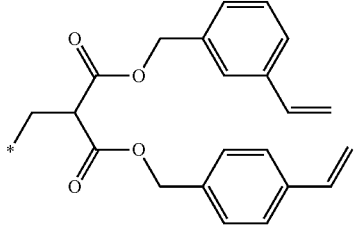
(III)-2
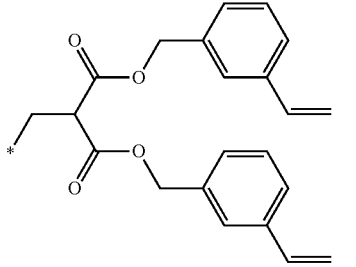
(III)-3
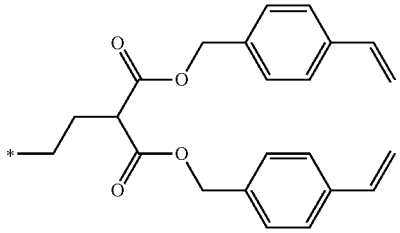
(III)-4
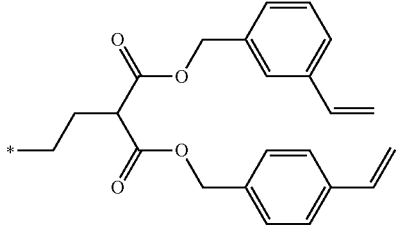
(III)-5
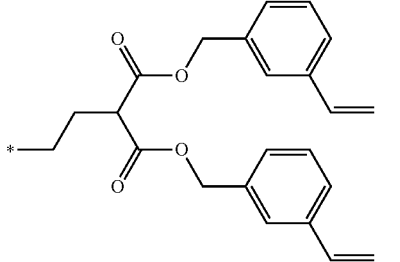
(III)-6

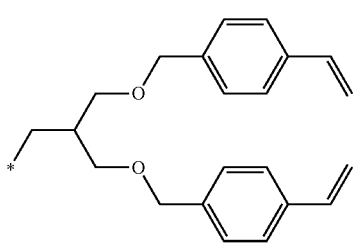
(III)-7
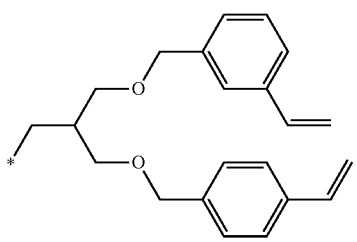
(III)-8
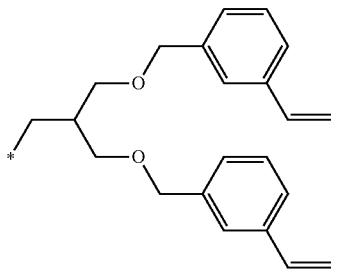
(III)-9
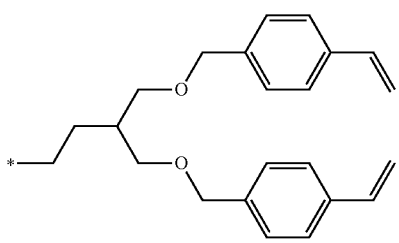
(III)-10
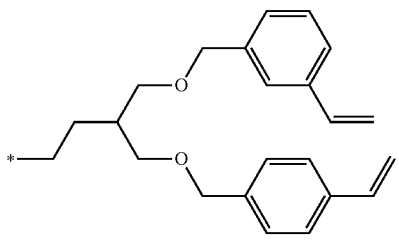
(III)-11
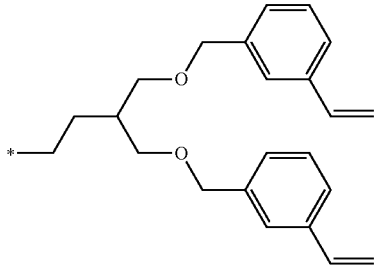
(III)-12
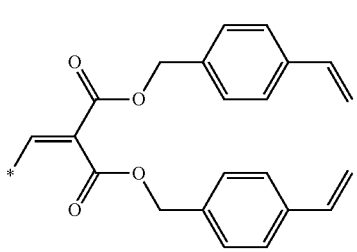
(III)-13
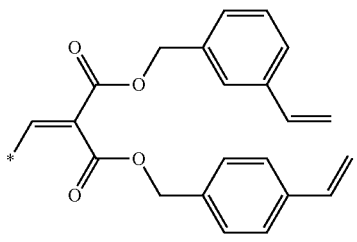
(III)-14
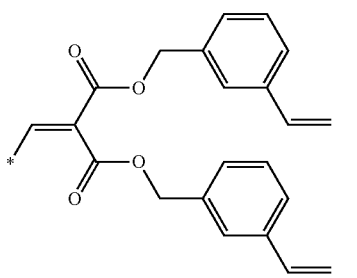
(III)-15
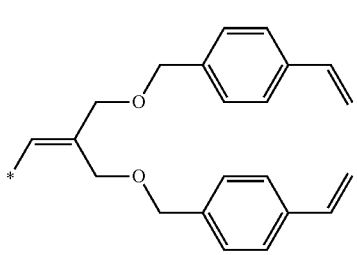
(III)-16
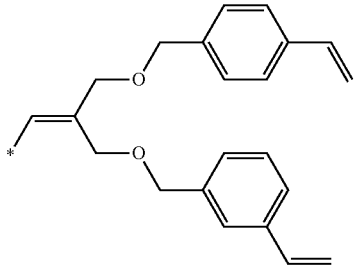
(III)-17
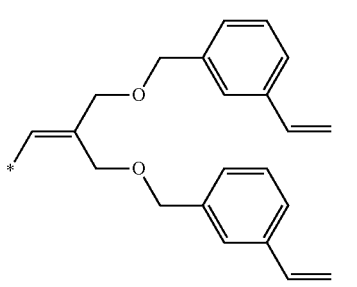
(III)-18

(III)-20
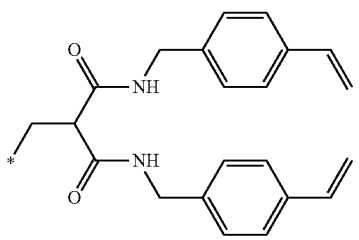
(III)-21
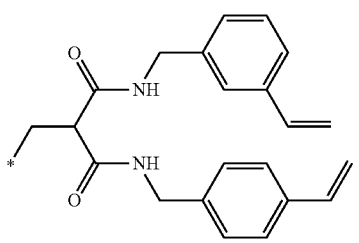
(III)-22
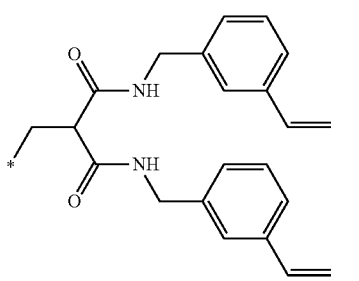
(III)-23
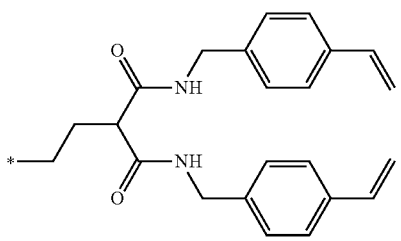
(III)-24
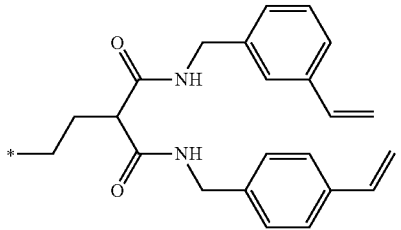
(III)-25
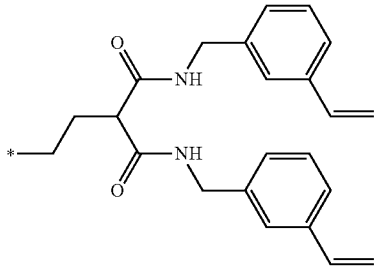
(III)-26
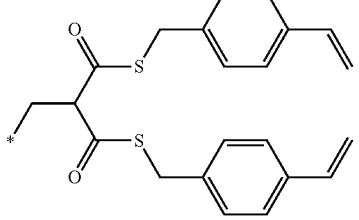
(III)-27
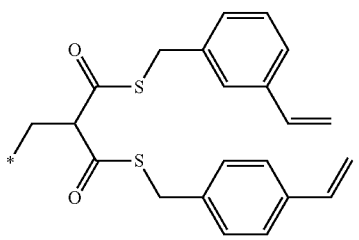
(III)-28
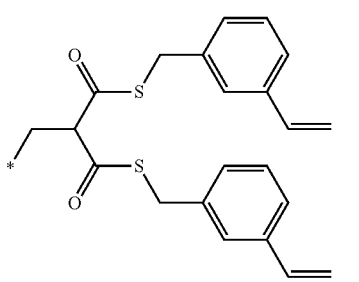
(III)-29
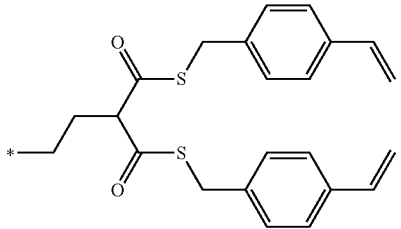
(III)-30
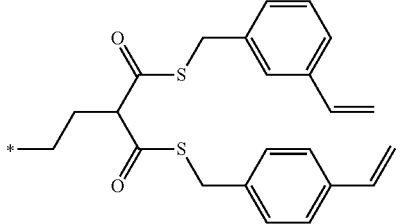
(III)-31
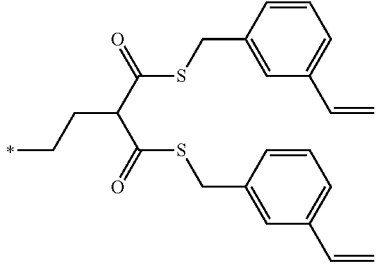

(III)-32
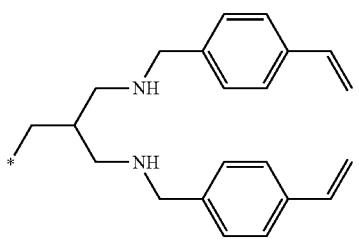
(III)-33
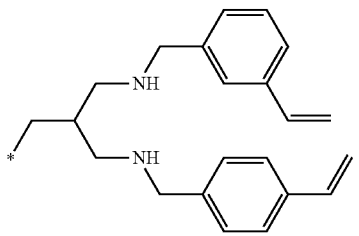
(III)-34
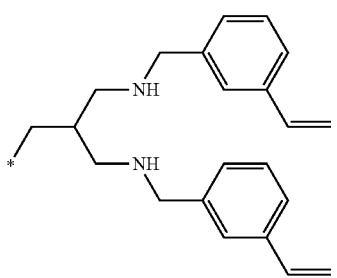
(III)-35
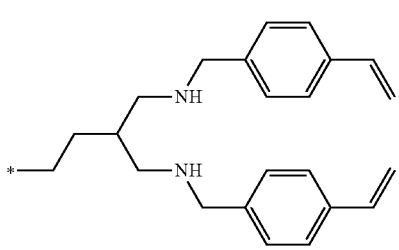
(III)-36
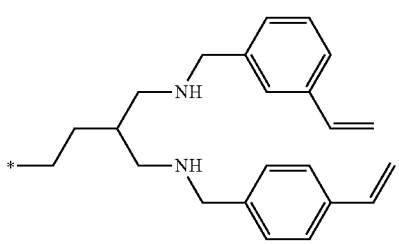
(III)-37
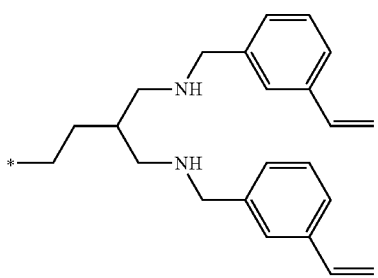
(III)-38
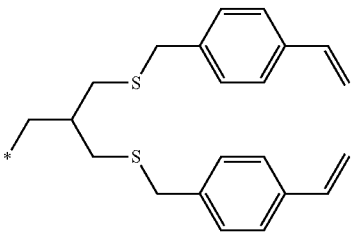
(III)-39
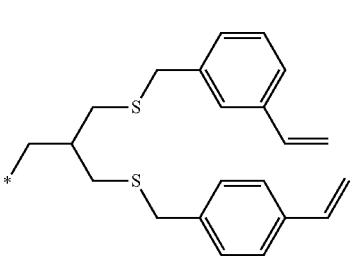
(III)-40
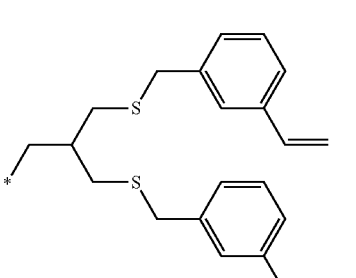
(III)-41
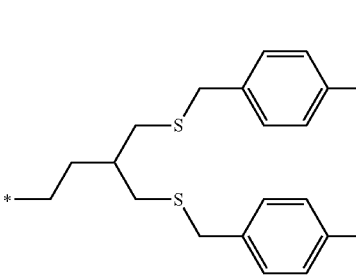
(III)-42
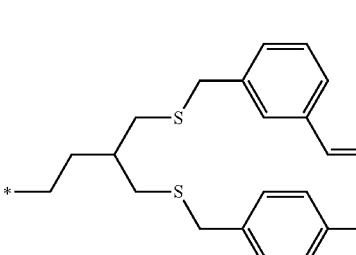
(III)-43
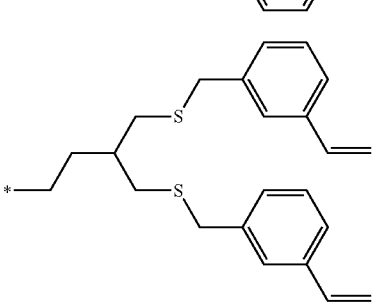

(III)-44
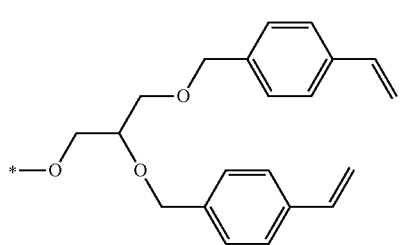
(III)-45
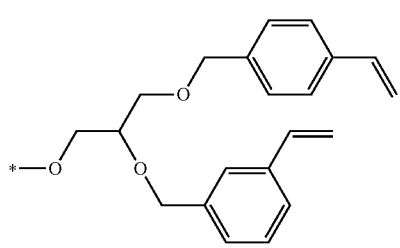
(III)-46
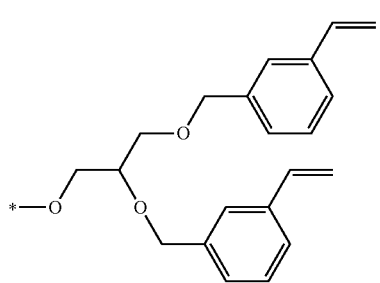
(III)-47
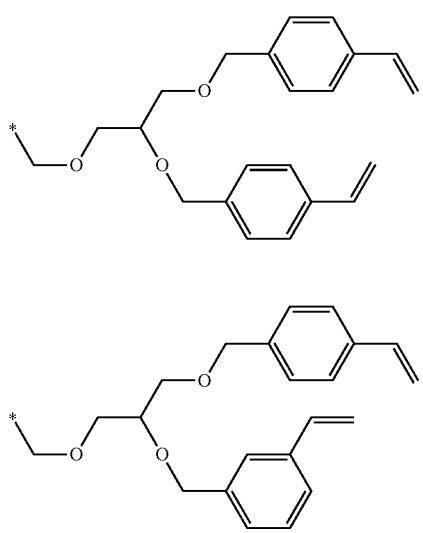
(III)-48
(III)-49
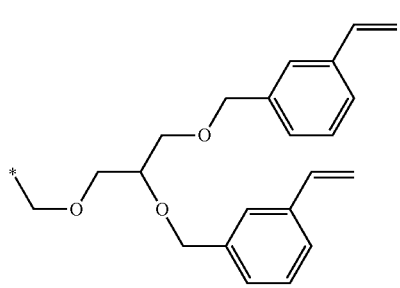
(III)-50
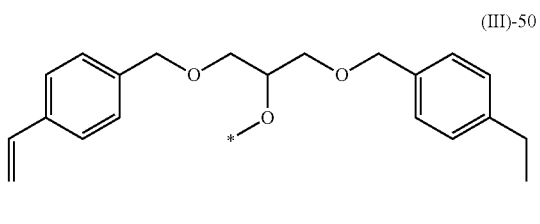
(III)-51
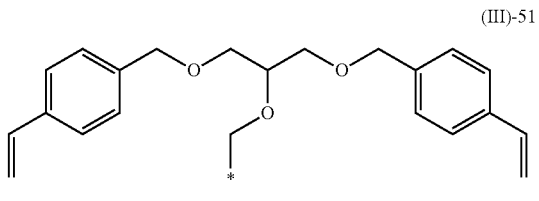
(III)-52
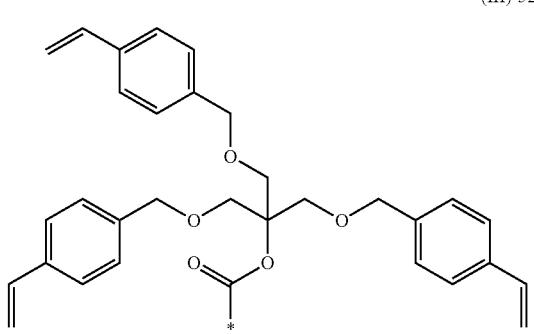
(III)-53
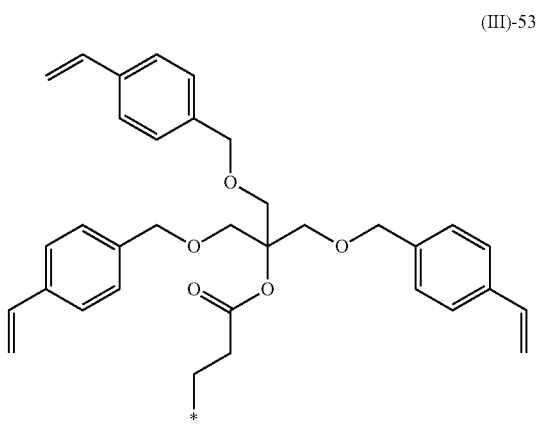
(III)-54
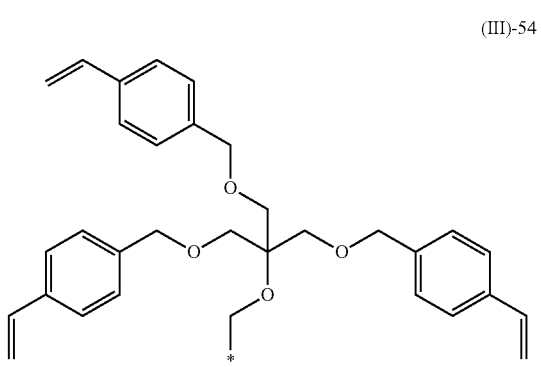

(III)-55

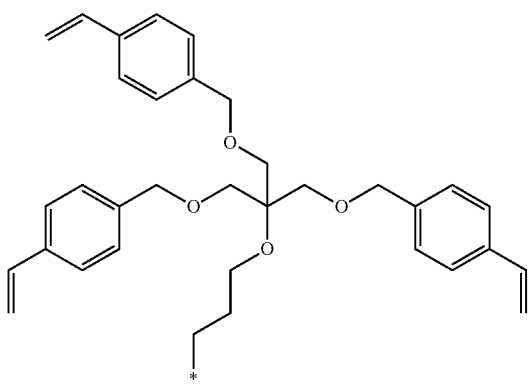

TABLE 1

| Compound No | Skeleton | Functional group |
|---|---|---|
| CTM-1 | (1)-1 | (III)-1 |
| CTM-2 | (1)-1 | (III)-7 |
| CTM-3 | (1)-1 | (III)-13 |
| CTM-4 | (1)-1 | (III)-16 |
| CTM-5 | (1)-2 | (III)-1 |
| CTM-6 | (1)-2 | (III)-7 |
| CTM-7 | (1)-2 | (III)-13 |
| CTM-8 | (1)-2 | (III)-16 |
| CTM-9 | (1)-4 | (III)-1 |
| CTM-10 | (1)-4 | (III)-7 |
| CTM-11 | (1)-4 | (III)-9 |
| CTM-12 | (1)-4 | (III)-13 |
| CTM-13 | (1)-4 | (III)-16 |
| CTM-14 | (1)-4 | (III)-23 |
| CTM-15 | (1)-4 | (III)-29 |
| CTM-16 | (1)-4 | (III)-44 |
| CTM-17 | (1)-11 | (III)-1 |
| CTM-18 | (1)-11 | (III)-7 |
| CTM-19 | (1)-21 | (III)-1 |
| CTM-20 | (1)-21 | (III)-7 |
| CTM-31 | (2)-1 | (III)-16 |
| CTM-32 | (2)-1 | (III)-29 |
| CTM-33 | (2)-2 | (III)-1 |
| CTM-34 | (2)-2 | (III)-7 |
| CTM-35 | (2)-3 | (III)-1 |
| CTM-36 | (2)-3 | (III)-13 |
| CTM-37 | (2)-12 | (III)-7 |
| CTM-38 | (2)-12 | (III)-29 |
| CTM-39 | (2)-13 | (III)-1 |
| CTM-40 | (2)-13 | (III)-7 |
| CTM-41 | (2)-13 | (III)-13 |
| CTM-42 | (2)-13 | (III)-16 |
| CTM-43 | (2)-13 | (III)-29 |
| CTM-44 | (2)-25 | (III)-1 |
| CTM-45 | (2)-25 | (III)-7 |
| CTM-46 | (2)-25 | (III)-13 |
| CTM-47 | (2)-25 | (III)-16 |
| CTM-48 | (2)-25 | (III)-23 |
| CTM-49 | (2)-25 | (III)-29 |
| CTM-50 | (2)-25 | (III)-44 |
| CTM-51 | (3)-1 | (III)-1 |
| CTM-52 | (3)-1 | (III)-7 |
| CTM-53 | (3)-1 | (III)-9 |
| CTM-54 | (3)-1 | (III)-13 |
| CTM-55 | (3)-1 | (III)-16 |
| CTM-56 | (3)-8 | (III)-1 |
| CTM-57 | (3)-8 | (III)-7 |
| CTM-58 | (3)-9 | (III)-1 |
| CTM-59 | (3)-11 | (III)-1 |
| CTM-60 | (3)-11 | (III)-7 |
| CTM-61 | (4)-4 | (III)-1 |
| CTM-62 | (4)-4 | (III)-7 |
| CTM-63 | (4)-4 | (III)-9 |
| CTM-64 | (4)-4 | (III)-13 |

TABLE 1-continued

| Compound No | Skeleton | Functional group |
|---|---|---|
| CTM-65 | (4)-4 | (III)-16 |
| CTM-66 | (4)-9 | (III)-1 |
| CTM-67 | (4)-9 | (III)-7 |
| CTM-68 | (4)-9 | (III)-9 |
| CTM-69 | (4)-9 | (III)-13 |
| CTM-70 | (4)-9 | (III)-16 |
| CTM-101 | (2)-26 | (III)-1 |
| CTM-102 | (2)-26 | (III)-7 |
| CTM-103 | (4)-3 | (III)-1 |
| CTM-104 | (4)-3 | (III)-7 |
| CTM-105 | (4)-3 | (III)-9 |
| CTM-106 | (4)-3 | (III)-13 |
| CTM-107 | (4)-3 | (III)-16 |

Next, a method of synthesizing the compound represented by General Formula (I) will be described.

For synthesizing the compound represented by General Formula (I), the methods used for synthesizing and reacting general charge transport materials as exemplified below may be applied. Specifically, the methods exemplified in the examples may be used.

Formylation: A reaction suitable for introducing a formyl group to an aromatic compound, a heterocyclic compound, or an alkene having an electron-donating group. In this reaction, N,N-dimethylformamide (hereinafter, written as "DMF") and phosphorous trioxychloride are used in general, and the reaction is performed at from room temperature to 100° C. in many cases.

Esterification: A condensation reaction between an organic acid and a compound including a hydroxyl group such as alcohol or phenol. In this reaction, it is desirable to use a technique that causes the reaction to be biased toward the ester side by adding a dehydrating agent or removing water from the reaction system.

Etherification: Williamson synthesis that condenses alkoxide and an organic halogen compound is generally used as this reaction.

Hydrogenation: A method of reacting hydrogen with an unsaturated bond by using various catalysts.

The novel compound (compound represented by General Formula (I)) according to the exemplary embodiment is a compound that obtains two or three chain-polymerizable reactive groups (styrene groups) from the charge transporting subunit represented by F via a linking group L.

Through a detailed examination, the present inventors clarified that if a degree of curing of a charge transporting compound is increased, that is, if the number of crosslinking sites is increased, the charge transport performance deteriorates. The reason is unclear. However, at the present stage, it is assumed that this is because a charge transporting site (charge transporting subunit) is distorted when being cured (crosslinked), if a degree of curing of the charge transporting compound, that is, the number of crosslinking sites is increased.

However, the compound represented by General Formula (I) has a structure in which the compound has two or three chain-polymerizable reactive groups via one linking group L. Consequently, even if the degree of curing and the number of crosslinking sites are kept to be high, the charge transporting subunit is not easily distorted when being cured (crosslinked) due to the existence of the linking group L, and a high curing degree may be compatible with an excellent charge transport performance.

The charge transporting compound having a (meth)acryl group, which has been used in the related art, is not only easily distorted, but also easily undergoes microphase separation since the reactive site thereof is highly hydrophilic while the charge transporting site thereof is highly hydrophobic. On the other hand, the compound represented by General Formula (I) has a styrene group as a reactive group and has a structure that includes the linking group L for which the charge transporting site (charge transporting subunit) is not easily distorted when being cured (crosslinked), and the phase separation does not easily occur in this compound since both the reactive site and charge transporting site are hydrophobic. Therefore, it is considered that the effective charge transport performance and high strength are realized for these reasons. Consequently, it is considered that the charge transporting film including a polymer of this compound represented by General Formula (I) is excellent in mechanical strength and exhibits a better charge transport performance (electrical characteristics).

In this respect, the novel compound (compound represented by General Formula (I)) according to the exemplary embodiment is useful for the charge transporting film.

[Charge Transporting Film]

The charge transporting film according to the exemplary embodiment is characterized by including at least a polymer of the novel compound (compound represented by General Formula (I)) according to the exemplary embodiment described above. The compound represented by General Formula (I) enables a high degree of curing and excellent charge transport performance to be compatible with each other. Accordingly, the charge transporting film containing the polymer of this compound becomes a charge transporting film that is excellent in both the mechanical strength and the charge transport performance.

This polymer is obtained by polymerizing the compound represented by General Formula (I) by using energy of heat, light, electron beams, and the like.

In addition, the charge transporting film containing this polymer is obtained by preparing a composition that contains the compound represented by General Formula (I) and optionally other components, and polymerizing (curing) this composition by energy of heat, light, electron beams, and the like.

The content of the polymer of the compound represented by General Formula (I) in the charge transporting film according to the exemplary embodiment may be set based on the charge transport performance according to the use of the charge transporting film. Generally, the content may be set within a range of from 5% by weight to 100% by weight (desirably from 40% by weight to 100% by weight) in the charge transporting film.

Moreover, the charge transporting film according to the exemplary embodiment may contain the compound itself (in an unreacted state) represented by General Formula (I), in addition to the polymer of the compound represented by General Formula (I).

As the compound represented by General Formula (I), compounds differing in the functional number of the chain-polymerizable functional group, that is, compounds differing in the number of the partial structure (group represented by General Formula (III)) may be used concurrently, whereby the strength of the charge transporting film (cured product) may be adjusted without deteriorating the charge transport performance.

Specifically, as the compound represented by General Formula (III), a compound having two or more functional groups may be concurrently used with a compound having the smaller number of functional groups, so as to adjust the strength of the charge transporting film (cured product) without deteriorating the charge transport performance.

When the compounds are concurrently used, the content of the compound having 2 or more functional groups may be set within a range of from 5% by weight to 95% by weight (desirably from 10% by weight to 90% by weight) based on the total content of the compound represented by General Formula (III).

The charge transporting film may further contain a thermal radical generator or a derivative thereof. That is, for forming the charge transporting film, a thermal radical generator or a derivative thereof may be used.

Herein, the "derivative of a thermal radical generator" refers to a reaction residue remaining after the radical is generated by heat or a substance formed when a radical active species binds to a polymer terminal.

The charge transporting film (crosslinked film) is obtained by curing a composition for forming a charge transporting film that contains the respective components described above through various methods such as heat, light, and electron beams. However, in order to keep balance between characteristics such as electrical characteristics and mechanical strength of the cured film, thermal curing is desirable. Usually, when a general acrylic coating material or the like is cured, electron beams that cure the material without using a catalyst or photopolymerization that cures the material in a short time is suitably used. However, since most of the charge transporting subunit has a structure that absorbs the light used for photopolymerization, the charge transport performance markedly deteriorates in many cases due to side reactions caused after the absorption. Therefore, it is desirable to perform thermal curing in which the reaction proceeds slowly, so as to improve surface properties of the obtained cured film.

Consequently, the thermal curing may be performed without a catalyst, but it is desirable to use the above-described thermal radical generator or a derivative thereof as a catalyst.

The thermal radical generator is not particularly limited. However, in order to prevent side reactions, the thermal radical generator is desirably the one having a 10-hour half life temperature of from 40° C. to 110° C.

Examples of the thermal radical generator include azo-based initiators such as V-30, (10-hour half life temperature: 104° C.), V-40 (10-hour half life temperature: 88° C.), V-59 (10-hour half life temperature: 67° C.), V-601 (10-hour half life temperature: 66° C.), V-65 (10-hour half life temperature: 51° C.), V-70 (10-hour half life temperature: 30° C.), VF-096 (10-hour half life temperature: 96° C.), Vam-110 (10-hour half life temperature: 111° C.), Vam-111 (10-hour half life temperature: 111° C.), VE-073 (10-hour half life temperature: 73° C.) (all manufactured by Wako Pure Chemical Industries, Ltd.), $OT_{AZO}$-15 (10-hour half life temperature: 61° C.), $OT_{AZO}$-30 (10-hour half life temperature: 57° C.), AIBN (10-hour half life temperature: 65° C.), AMBN (10-hour half life temperature: 67° C.), ADVN (10-hour half life temperature: 52° C.), and ACVA (10-hour half life temperature: 68° C.) (all manufactured by Otsuka Chemical Co., Ltd.); Pertetra A, Perhexa HC, Perhexa C, Perhexa V, Perhexa 22, Perhexa MC, Perbutyl H, Percumyl H, Percumyl P, Permenta H, Perocta H, Perbutyl C, Perbutyl D, Perhexyl D, Peroyl IB, Peroyl 355, Peroyl L, Peroyl SA, Nyper BW, Nyper BMT-K40/M, Peroyl IPP, Peroyl NPP, Peroyl TCP, Peroyl OPP, Peroyl SBP, Percumyl ND, Perocta ND, Perhexyl ND, Perbutyl ND, Perbutyl NHP, Perhexyl PV, Perbutyl PV, Perhexa 250, Perocta O, Perhexyl O, Perbutyl O, Perbutyl L, Perbutyl 355, Perhexyl I, Perbutyl I, Perbutyl E, Perhexa 25Z, Perbutyl A, Perhexyl Z, Perbutyl ZT, and Perbutyl Z (all manufactured by NOF CORPORATION); Kayaketal AM-055, Trigonox 36-C75, Laurox, Perkadox L-W75, Perkadox CH-50L, Trigonox TMBH, Kayacumene H, Kayabutyl H-70, Perkadox BC-FF, Kayahexa AD, Perkadox 14, Kayabutyl C, Kayabutyl D, Kayahexa YD-E85, Perkadox 12-XL25, Perkadox 12-EB20, Trigonox 22-N70, Trigonox 22-70E, Trigonox D-T50, Trigonox 423-C70, Kayaester CND-C70, Kayaester CND-W50, Trigonox 23-C70, Trigonox 23-W50N, Trigonox 257-C70, Kayaester α-70, Kayaester TMPO-70, Trigonox 121, Kayaester O, Kayaester HTP-65W, Kayaester AN, Trigonox 42, Trigonox F-050, Kayabutyl B, Kayacarbon EH-C70, Kayacarbon EH-W60, Kayacarbon 1-20, Kayacarbon BIC-75, Trigonox 117, and Kayalene 6-70 (all manufactured by KAYAAKZO CO., LTD.); Luperox LP (10-hour half life temperature: 64° C.), Luperox 610 (10-hour half life temperature: 37° C.), Luperox 188 (10-hour half life temperature: 38° C.), Luperox 844 (10-hour half life temperature: 44° C.), Luperox 259 (10-hour half life temperature: 46° C.), Luperox 10 (10-hour half life temperature: 48° C.), Luperox 701 (10-hour half life temperature: 53° C.), Luperox 11 (10-hour half life temperature: 58° C.), Luperox 26 (10-hour half life temperature: 77° C.), Luperox 80 (10-hour half life temperature: 82° C.), Luperox 7 (10-hour half life temperature: 102° C.), Luperox 270 (10-hour half life temperature: 102° C.), Luperox P (10-hour half life temperature: 104° C.), Luperox 546 (10-hour half life temperature: 46° C.), Luperox 554 (10-hour half life temperature: 55° C.), Luperox 575 (10-hour half life temperature: 75° C.), Luperox TANPO (10-hour half life temperature: 96° C.), Luperox 555 (10-hour half life temperature: 100° C.), Luperox 570 (10-hour half life temperature: 96° C.), Luperox TAP (10-hour half life temperature: 100° C.), Luperox TBIC (10-hour half life temperature: 99° C.), Luperox TBEC (10-hour half life temperature: 100° C.), Luperox JW (10-hour half life temperature: 100° C.), Luperox TAIC (10-hour half life temperature: 96° C.), Luperox TAEC (10-hour half life temperature: 99° C.), Luperox DC (10-hour half life temperature: 117° C.), Luperox 101 (10-hour half life temperature: 120° C.), Luperox F (10-hour half life temperature: 116° C.), Luperox DI (10-hour half life temperature: 129° C.), Luperox 130 (10-hour half life temperature: 131° C.), Luperox 220 (10-hour half life temperature: 107° C.), Luperox 230 (10-hour half life temperature: 109° C.), Luperox 233 (10-hour half life temperature: 114° C.), and Luperox 531 (10-hour half life temperature: 93° C.) (all manufactured by ARKEMA YOSHITOMI, LTD.); and the like.

The thermal radical generator or a derivative thereof is contained in the composition desirably at from 0.001% by weight to 10% by weight, more desirably at from 0.01% by weight to 5% by weight, and even more desirably at from 0.1% by weight to 3% by weight, based on the reactive compound (reactive compound represented by General Formula (I)+other reactive compounds) in the composition for forming a charge transporting film.

Other components used for forming the charge transporting film may be appropriately selected according to the use of the charge transporting film. Examples of other components include a polymerizable compound not having a charge transport performance and a compound that has a charge transport performance but is different from the compound represented by General Formula (I) as compounds involving curing or polymerization, a non-polymerizable charge transporting compound, a surfactant, other thermosetting resins, an antioxidant, and the like.

Specific examples of the polymerizable compound not having a charge transport performance include the following ones.

Examples of a monofunctional radical-polymerizable monomer include isobutyl acrylate, t-butyl acrylate, isooctyl acrylate, lauryl acrylate, stearyl acrylate, isobornyl acrylate, cyclohexyl acrylate, 2-methoxyethyl acrylate, methoxy triethylene glycol acrylate, 2-ethoxyethyl acrylate, tetrahydrofurfuryl acrylate, benzyl acrylate, ethyl carbitol acrylate, phenoxyethyl acrylate, 2-hydroxy acrylate, 2-hydroxypropyl acrylate, 4-hydroxybutyl acrylate, methoxy polyethylene glycol acrylate, methoxy polyethylene glycol methacrylate, phenoxy polyethylene glycol acrylate, phenoxy polyethylene glycol methacrylate, hydroxyethyl γ-phenyl phenol acrylate, o-phenyl phenol glycidyl ether acrylate, and the like.

Examples of a bifunctional radical-polymerizable monomer include 1,4-butanediol diacrylate, 1,6-hexanediol diacrylate, 1,9-nonanediol diacrylate, 2-n-butyl-2-ethyl-1,3-propanediol diacrylate, tripropylene glycol diacrylate, tetraethylene glycol diacrylate, dioxane glycol diacrylate, polytetramethylene glycol diacrylate, ethoxylated bisphenol A diacrylate, ethoxylated bisphenol A dimethacrylate, tricyclodecane methanol diacrylate, tricyclodecane methanol dimethacrylate, and the like.

Examples of a tri- or higher functional radical-polymerizable monomer include trimethylolpropane triacrylate, trimethylolpropane trimethacrylate, pentaerythritol acrylate, trimethylolpropane EO-added triacrylate, glycerin PO-added triacrylate, trisacryloyloxy ethyl phosphate, pentaerythritol tetraacrylate, ethoxylated isocyanur triacrylate, and the like.

In addition, examples of a radical-polymerizable oligomer include oligomers based on epoxy acrylate, urethane acrylate, and polyester acrylate.

Examples of the compound that has a charge transport performance but is different from the compound represented by General Formula (I) include a compound having an acryl group, a compound having a reactive hydroxyl group, a compound having an alkoxysilyl group, and the like.

Examples of the non-polymerizable charge transporting compound include oxadiazole derivative such as 2,5-bis(p-diethylaminophenyl)-1,3,4-oxadiazole; a pyrazoline derivative such as 1,3,5-triphenyl-pyrazoline or 1-[pyridyl-(2)]-3-(p-diethylaminostyryl)-5-(p-diethylamino styryl)pyrazoline; an aromatic tertiary amino compound such as triphenylamine, N,N'-bis(3,4-dimethylphenyl)biphenyl-4-amine, tri(p-methylphenyl)aminyl-4-amine, or dibenzylaniline; an aromatic tertiary diamino compound such as N,N'-bis(3-methylphenyl)-N,N'-diphenylbenzidine; a 1,2,4-triazine derivative such as 3-(4'-dimethylaminophenyl)-5,6-di-(4'-methoxyphenyl)-1,2,4-triazine; a hydrazone derivative such as 4-diethylaminobenzaldehyde-1,1-diphenylhydrazone; a quinazoline derivative such as 2-phenyl-4-styryl-quinazoline; a benzofuran derivative such as 6-hydroxy-2,3-di(p-methoxyphenyl)benzofuran; an α-stilbene derivative such as p-(2,2-diphenylvinyl)-N,N-diphenyl aniline; an enamine derivative; a carbazole derivative such as N-ethylcarbazole; hole transport materials such as poly-N-vinylcarbazole and a derivative thereof; a quinone-based compound such as chloranil or bromoanthraquinone; a tetracyanoquinodimethane-based compound; a fluorenone compound, such as 2,4,7-trinitrofluorenone or 2,4,5,7-tetranitro-9-fluorenone; a xanthone-based compound; and an electron transport material such as a thiophene compound; and a polymer having a group including the above compounds in a main chain or a side chain thereof. These charge transporting materials may be used alone or in combination of two or more kinds thereof.

The surfactant includes one or more structures among (A) a structure formed by polymerizing acrylic monomers having a fluorine atom, (B) a structure having a carbon-carbon double bond and a fluorine atom, (C) an alkylene oxide structure, and (D) a structure having a carbon-carbon triple bond and a hydroxyl group, in a molecule.

Specific examples of the surfactant include Polyflow KL-600 (manufactured by KYOEISHA CHEMICAL Co., LTD); Eftop Eftop EF-351, Eftop EF-352, Eftop EF-801, Eftop EF-802, and Eftop EF-601 (all manufactured by JEMCO, Inc.); Ftergent 100, Ftergent 100C, Ftergent 110, Ftergent 140A, Ftergent 150, Ftergent 150CH, Ftergent A-K, Ftergent 501, Ftergent 250, Ftergent 251, Ftergent 222F, Ftergent FTX-218, Ftergent 300, Ftergent 310, Ftergent 400SW, Ftergent 212M, Ftergent 245M, Ftergent 290M, Ftergent FTX-207S, Ftergent FTX-211S, Ftergent FTX-220S, Ftergent FTX-230S, Ftergent FTX-209F, Ftergent FTX-213F, Ftergent FTX-222F, Ftergent FTX-233F, Ftergent FTX-245F, Ftergent FTX-208G, Ftergent FTX-218G, Ftergent FTX-230G, Ftergent FTX-240G, Ftergent FTX-204D, Ftergent FTX-280D, Ftergent FTX-212D, Ftergent FTX-216D, Ftergent FTX-218D, Ftergent FTX-220D, and Ftergent FTX-222D (manufactured by NEOS COMPANY LIMITED.); PE-M and PE-L (all manufactured by Wako Pure Chemical Industries, Ltd.); antifoam agents No. 1 and No. 5 (all manufactured by Kao Corporation); KF351 (A), KF352 (A), KF353 (A), KF354 (A), KF355 (A), KF615 (A), KF618, KF945 (A), and KF6004 (all manufactured by Shin-Etsu Chemical Co., Ltd.); TSF4440, TSF4445, TSF4450, TSF4446, TSF4452, TSF4453, and TSF4460 (all manufactured by GE Toshiba Silicones, Co., Ltd.); BYK-300, 302, 306, 307, 310, 315, 320, 322, 323, 325, 330, 331, 333, 337, 341, 344, 345, 346, 347, 348, 370, 375, 377, 378, UV3500, UV3510, and UV3570 (all manufactured by BYK-Chemie Japan KK), and the like.

Examples of other thermosetting resins include a phenol resin, a melamine resin, a benzoguanamine resin, and the like.

As the antioxidant, antioxidants based on hindered phenol or hindered amine are desirable, and known antioxidants such as an organic sulfur-based antioxidant, a phosphite-based antioxidant, a dithiocarbamic acid salt-based antioxidant, a thiourea-based antioxidant, and a benzimidazole-based antioxidant may also be used.

Examples of the hindered phenol-based antioxidant include 2,6-di-t-butyl-4-methylphenol, 2,5-di-t-butylhydroquinone, N,N'-hexamethylenebis (3,5-di-t-butyl-4-hydroxyhydrocinnamide, 3,5-di-t-butyl-4-hydroxy-benzylphosphonate-diethyl ester, 2,4-bis[(octylthio)methyl]-o-cresol, 2,6-di-t-butyl-4-ethylphenol, 2,2'-methylenebis(4-methyl-6-t-butylphenol), 2,2'-methylenebis(4-ethyl-6-t-butylphenol), 4,4'-butylidenebis(3-methyl-6-t-butylphenol), 2,5-di-t-amylhydroguinone, 2-t-butyl-6-(3-butyl-2-hydroxy-5-methylbenzyl)-4-methylphenyl acrylate, 4,4'-butylidenebis (3-methyl-6-t-butylphenol), and the like.

The charge transporting film according to the exemplary embodiment is used for, for example, an electrophotographic photoreceptor, an organic EL device, an organic transistor, and an organic solar cell.

[Photoelectric Conversion Device]

The photoelectric conversion device according to the exemplary embodiment is characterized by including the charge transporting film according to the exemplary embodiment described above.

As described above, the charge transporting film according to the exemplary embodiment is excellent in both the mechanical strength and charge transport performance. Therefore, this film may be suitably applied to a layer which needs to have mechanical strength in a photoelectric conversion device.

Examples of the photoelectric conversion device according to the exemplary embodiment include an electrophotographic photoreceptor, an organic EL device, an organic transistor, an organic solar cell, and the like.

Specifically, for example, the organic EL device is configured with a pair of electrodes in which at least one of the electrodes is transparent or semitransparent, and one or plural organic compound layers interposed between these electrodes. The charge transporting film according to the exemplary embodiment of the invention may be used for at least one of the organic compound layers, and the layer configuration thereof is not particularly limited. Specifically, the charge transporting film according to the exemplary embodiment is applied as a luminous layer, a hole transporting layer, and a hole injecting layer.

In addition, for example, an organic thin film transistor includes an organic semiconductor layer that contacts both a source electrode and a drain electrode facing each other, a gate electrode that is separated from both the source electrode and drain electrode, and an insulating layer disposed between the organic semiconductor layer and the gate electrode. The charge transporting film according to the exemplary embodiment of the invention may be used for at least one of the organic semiconductor layers, and the layer configuration thereof is not particularly limited.

<Electrophotographic Photoreceptor>

The electrophotographic photoreceptor according to the exemplary embodiment is characterized by including a charge transporting layer that contains at least the polymer of the compound represented by General Formula (I) described above.

As described above, the compound represented by General Formula (I) may form a charge transporting layer that is excellent in both the mechanical strength and the charge transport performance. Accordingly, in the electrophotographic photoreceptor to which this charge transporting layer is applied, the deterioration of electrical characteristics is inhibited even if the electrophotographic photoreceptor is repeatedly used for a long time, and consequently, it is considered that stabilized images may be continuously obtained for this reason.

Particularly, since the charge transporting layer also has high mechanical strength, it is desirable to apply this layer to an outermost surface layer of the electrophotographic photoreceptor. When such a configuration is employed, the deterioration of electrical characteristics is inhibited even if the electrophotographic photoreceptor is repeatedly used for a long time, and consequently, it is considered that stabilized images may be continuously obtained for this reason.

The polymer included in the charge transporting layer is obtained by polymerizing the compound represented by General Formula (I) by using energy of heat, light, electron beams, and the like.

In addition, the charge transporting layer including the polymer is obtained by preparing a composition that contains the compound represented by General Formula (I) and optionally other components, and polymerizing (curing) this composition by using energy of heat, light, electron beams, and the like.

The content of the polymer of the compound represented by General Formula (I) in the charge transporting layer according to the exemplary embodiment may be set based on the charge transport performance according to the use of the charge transporting layer. Generally, the content may be set within a range of from 5% by weight to 100% by weight (desirably from 40% by weight to 100% by weight) in the charge transporting layer.

Moreover, the charge transporting layer according to the exemplary embodiment may contain the compound itself (in an unreacted state) represented by General Formula (I), in addition to the polymer of the compound represented by General Formula (I).

In the charge transporting layer in the electrophotographic photoreceptor according to the exemplary embodiment, compounds differing in the functional number of the chain-polymerizable functional group, that is, compounds differing in the number of the partial structure (group represented by General Formula (III)) may be used concurrently as the compound represented by General Formula (I), whereby the strength of the charge transporting layer (cured product) may be adjusted without deteriorating the charge transport performance.

Specifically, as the compound represented by General Formula (III), a compound having two or more functional groups may be concurrently used with a compound having the smaller number of functional groups, so as to adjust the strength of the charge transporting layer (cured product) without deteriorating the charge transport performance.

When the compounds are concurrently used, the content of the compound having two or more functional groups may be set within a range of from 5% by weight to 95% by weight (desirably from 10% by weight to 90% by weight) based on the total content of the compound represented by General Formula (III).

The electrophotographic photoreceptor according to the exemplary embodiment includes the charge transporting layer according to the exemplary embodiment. The charge transporting layer may be anyone of the outermost surface layer and a layer other than the outermost surface layer. However, as described above, the charge transporting layer is desirably the outermost surface layer, in the respect that the charge transporting layer is excellent in both the mechanical strength and the charge transport performance.

The outermost surface layer forms an uppermost surface of the electrophotographic photoreceptor itself, and particularly, the outermost surface layer is desirably provided as a layer functioning as a protective layer or as a layer functioning as a charge transporting layer.

When the outermost surface layer functions as a protective layer, an embodiment is exemplified in which a photosensitive layer and a protective layer as an outermost surface layer are provided on a conductive substrate, and the protective layer configures a charge transporting layer described above.

On the other hand, when the outermost surface layer functions as a charge transporting layer, an embodiment is exemplified in which a charge generating layer and a charge transporting layer as an outermost surface layer are provided on a conductive substrate, and this charge transporting layer configures the charge transporting layer described above.

In addition, when the charge transporting layer described above configures a layer other than the outermost surface layer, an embodiment is exemplified in which a photosensitive layer including a charge generating layer and an outermost surface layer is provided on a conductive substrate, a protective layer is provided on the photosensitive layer as an outermost surface layer, and this protective layer configures the charge transporting layer described above.

Hereinafter, the electrophotographic photoreceptor according to the exemplary embodiment in a case where the charge transporting layer described above functions as a protective layer that becomes an outermost surface layer will be described in detail with reference to drawings. In the drawing, the same or corresponding portions are marked with the same reference numerals to omit repeated description.

Figure 2:
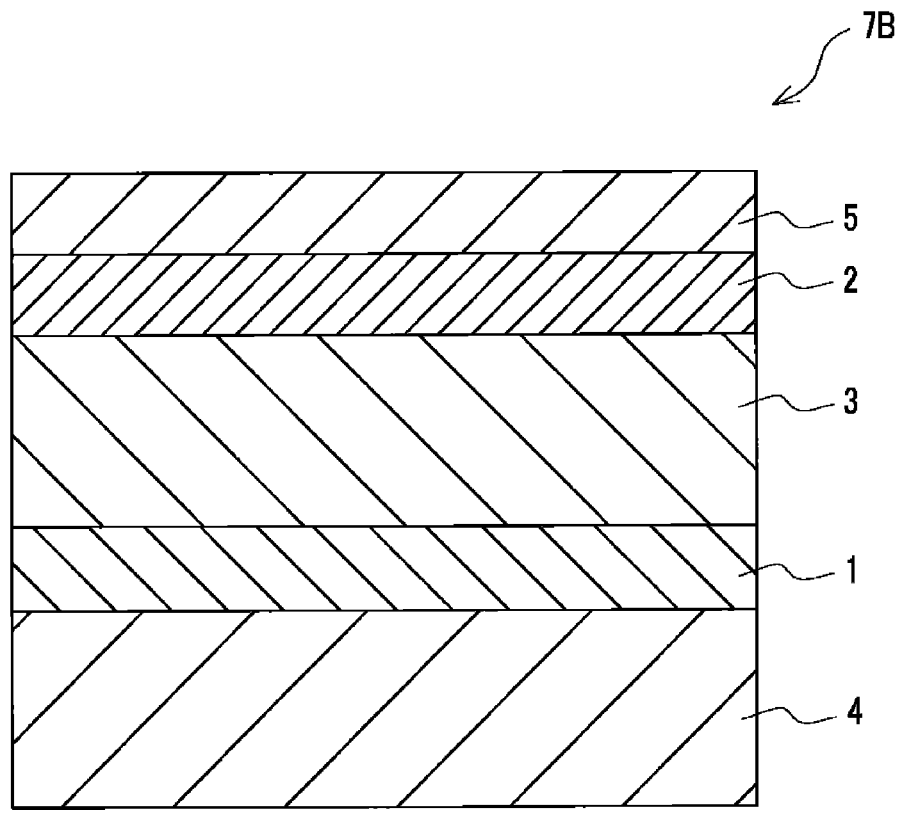
FIG. 2 is a schematic partial cross-sectional view showing an electrophotographic photoreceptor according to an exemplary embodiment.
Figure 3:
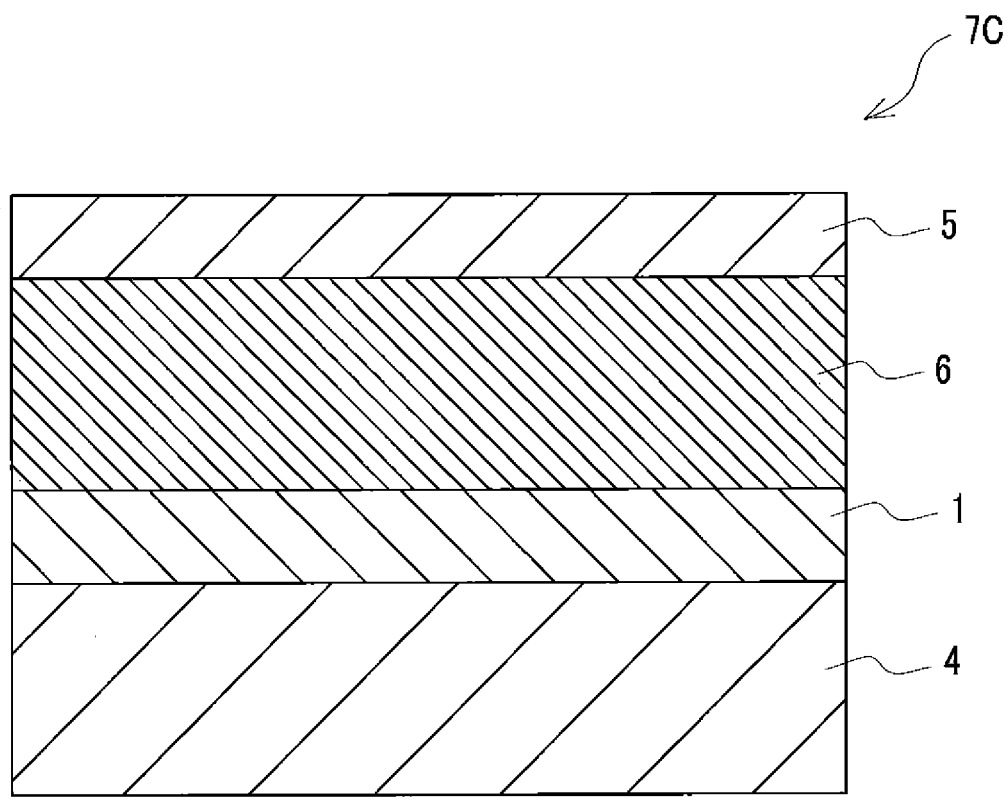
FIG. 3 is a schematic partial cross-sectional view showing an electrophotographic photoreceptor according to an exemplary embodiment.

FIG. 1 is a schematic cross-sectional view showing a suitable exemplary embodiment of the electrophotographic photoreceptor according to the exemplary embodiment. FIGS. 2 and 3 are schematic cross-sectional views showing electrophotographic photoreceptors according to other exemplary embodiments.

An electrophotographic photoreceptor 7A shown in FIG. 1 is a so-called functional separation type photoreceptor (or laminated type photoreceptor). The electrophotographic photoreceptor 7A has a structure in which an undercoat layer 1 is provided on a conductive substrate 4, and a charge generating layer 2, a charge transporting layer 3, and a protective layer 5 are formed in this order on the undercoat layer 1. In the electrophotographic photoreceptor 7A, a photosensitive layer is configured with the charge generating layer 2 and the charge transporting layer 3.

An electrophotographic photoreceptor 7B shown in FIG. 2 is a functional separation type photoreceptor that is functionally divided into the charge generating layer 2 and the charge transporting layer 3, similarly to the electrophotographic photoreceptor 7A shown in FIG. 1. In addition, an electrophotographic photoreceptor 7C shown in FIG. 3 contains a charge generating material and a charge transporting material in the same layer (single layer type photosensitive layer 6 (charge generating/charge transporting layer)).

The electrophotographic photoreceptor 7B shown in FIG. 2 has a structure in which the undercoat layer 1 is provided on the conductive substrate 4, and the charge transporting layer 3, the charge generating layer 2, and the protective layer 5 are formed in this order on the undercoat layer 1. In the electrophotographic photoreceptor 7B, the charge transporting layer 3 and the charge generating layer 2 configure a photosensitive layer.

The electrophotographic photoreceptor 7C shown in FIG. 3 has a structure in which the undercoat layer 1 is provided on the conductive substrate 4, and the single layer type photosensitive layer 6 and the protective layer 5 are formed in this order on the undercoat layer 1.

In the electrophotographic photoreceptors 7A to 7C shown in FIGS. 1 to 3, the protective layer 5 is an outermost surface layer that is disposed farthest away from the conductive substrate 4, and this outermost surface layer configures the charge transporting layer described above.

In the electrophotographic photoreceptors shown in FIGS. 1 to 3, the undercoat layer 1 may or may not be provided.

Hereinafter, based on the electrophotographic photoreceptor 7A shown in FIG. 1 as a typical example, the respective elements will be described.

(Conductive Substrate)

Any material may be used as the conductive substrate so long as the material has been used in the related art. Examples of the material include paper, plastic film, or the like coated or impregnated with a conductivity-imparting agent, such as a plastic film provided with a thin film (for example, metals such as aluminum, nickel, chromium, and stainless steel; and a film of aluminum, titanium, nickel, chromium, stainless steel, gold, vanadium, tin oxide, indium oxide, indium tin oxide (hereinafter, written as "ITO"), or the like). The shape of the substrate is not limited to a cylindrical shape, and the substrate may have an approximately sheet shape or plate shape.

The conductive substrate desirably has conductivity in which volume resistivity is less than $10^7 \Omega \cdot cm$, for example.

When a metal pipe is used as the conductive substrate, the surface of the pipe may remain as it is or may be treated in advance with mirror surface cutting, etching, anodization, rough cutting, centerless grinding, sand blasting, wet honing, or the like.

(Undercoat Layer)

The undercoat layer is provided optionally, for the purposes of preventing light reflection in the surface of the conductive substrate, preventing unnecessary inflow of a carrier to the photosensitive layer from the conductive substrate, and the like.

The undercoat layer is configured with, for example, a binder resin and optionally other additives.

Examples of the binder resin included in the undercoat layer include known polymeric resin compounds such as an acetal resin including polyvinyl butyral, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a phenol resin, a phenol-formaldehyde resin, a melamine resin, and a urethane resin, a charge transporting resin having a charge transporting group, a conductive resin such as polyaniline, and the like. Among these, a resin insoluble in a coating solvent of the upper layer is desirably used, and particularly, a phenol resin, a phenol-formaldehyde resin, a melamine resin, a urethane resin, an epoxy resin, and the like are desirably used.

The undercoat layer may contain a metal compound such as a silicon compound, an organic zirconium compound, an organic titanium compound, an organic aluminum compound, or the like.

The proportion between the metal compound and the binder resin is not particularly limited and may be set within a range in which desired characteristics of the electrophotographic photoreceptor are obtained.

In order to adjust the surface roughness, resin particles may be added to the undercoat layer. Examples of the resin particles include silicone resin particles, crosslinked polymethyl methacrylate (PMMA) resin particles, and the like. In addition, to adjust the surface roughness, the surface of the formed undercoat layer may be polished. As the polishing method, buffing, sand blasting, wet honing, grinding, and the like are used.

Herein, examples of the configuration of the undercoat layer include a configuration that contains at least a binder resin and conductive particles. The conductive particles desirably have conductivity in which volume resistivity is, for example, less than $10^7 \Omega \cdot cm$.

Examples of the conductive particles include metal particles (particles of aluminum, copper, nickel, silver, or the like), conductive metallic oxide particles (particles of antimony oxide, indium oxide, tin oxide, zinc oxide, or the like), and conductive material particles (particles of carbon fiber, carbon black, graphite powder, or the like). Among these, conductive metallic oxide particles are suitable. The conductive particles may be used as a mixture of two or more kinds thereof.

The conductive particles may be used after being surface-treated using a hydrophobicizing agent (for example, a coupling agent) to adjust resistance.

The content of the conductive particles is, for example, desirably from 10% by weight to 80% by weight, and more desirably from 40% by weight to 80% by weight, based on the binder resin.

For the formation of the undercoat layer, a coating liquid for forming an undercoat layer obtained by adding the above components to a solvent is used.

As methods of dispersing the particles in the coating liquid for forming an undercoat layer, a media dispersing machine such as a ball mill, a vibration ball mill, an attritor, a sand mill, or a horizontal sand mill; stirring; and a media-less dispersing machine such as an ultrasonic dispersing machine, a roll mill, or a high pressure homogenizer are used. Herein, examples of the high pressure homogenizer include a collision type which disperses a dispersion through liquid-to-liquid collision or liquid-to-wall, collision in a high pressure state, a penetration type which disperses the dispersion by causing the dispersion to penetrate a fine flow path in a high pressure state, and the like.

Examples of a method of coating the coating liquid for forming an undercoat layer onto the conductive substrate include dip coating, push-up coating, wire bar coating, spray coating, blade coating, knife coating, curtain coating, and the like.

The film thickness of the undercoat layer is desirably 15 µm or more, and more desirably from 20 µm to 50 µm.

Though not shown in the drawing, an interlayer may be provided between the undercoat layer and the photosensitive layer. Examples of the binder resin used for the interlayer include polymeric resin compounds such as an acetal resin including polyvinyl butyral, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a phenol-formaldehyde resin, a melamine resin, and organic metal compounds containing zirconium, titanium, aluminum, manganese, silicon atoms, and the like. These compounds may be used alone, or may be used as a mixture of plural compounds or as a polycondensate. Among these, an organic metal compound containing zirconium or silicon is suitable in respect that residual potential is low, and potential change caused by environments and repeated use is small in this compound.

For the formation of the interlayer, a coating liquid for forming an interlayer obtained by adding the above components to a solvent is used.

As a coating method for forming the interlayer, general methods such as dip coating, push-up coating, wire bar coating, spray coating, blade coating, knife coating, and curtain coating are used.

The interlayer not only plays a role of improving a coating property of the upper layer, but also plays a role of an electrical blocking layer. However, when the film thickness of the interlayer is too large, an electrical barrier becomes too strong, which leads to desensitization or potential increase caused by repeated use in some cases. Accordingly, when the interlayer is formed, the film thickness thereof is desirably set in a range of from 0.1 µm to 3 µm. In addition, the interlayer in this case may be used as an undercoat layer.

(Charge Generating Layer)

The charge generating layer is configured with, for example, a charge generating material and a binder resin. Examples of the charge generating material include phthalocyanine pigments such as metal-free phthalocyanine, chlorogallium phthalocyanine, hydroxygallium phthalocyanine, dichlorotin phthalocyanine, and titanyl phthalocyanine. The examples particularly include chlorogallium phthalocyanine crystals having strong diffraction peaks at Bragg angles) (2θ±0.2°) of at least 7.4°, 16.6°, 25.5°, and 28.3° with respect to an X-ray with CuKα characteristics, metal-free phthalocyanine crystals having strong diffraction peaks at Bragg angles (2θ±0.2°) of at least 7.7°, 9.3°, 16.9°, 17.5°, 22.4°, and 28.8° with respect to an X-ray with CuKα characteristics, hydroxygallium phthalocyanine crystals having strong diffraction peaks at Bragg angles (2θ±0.2°) of at least 7.5°, 9.9°, 12.5°, 16.3°, 18.6°, 25.1°, and 28.3° with respect to an X-ray with CuKα characteristics, and titanyl phthalocyanine crystals having strong diffraction peaks at Bragg angles) (2θ±0.2°) of at least 9.6°, 24.1°, and 27.2° with respect to an X-ray with CuKα characteristics. Examples of the charge generating material also include a quinone pigment, a perylene pigment, an indigo pigment, a bisbenzimidazole pigment, an anthrone pigment, a quinacridone pigment, and the like. These charge generating materials may be used alone or used as a mixture of two or more kinds thereof.

Examples of the binder resin configuring the charge generating layer include a bisphenol A type or bisphenol Z type polycarbonate resin, an acrylic resin, a methacrylic resin, a polyarylate resin, a polyester resin, a polyvinyl chloride resin, a polystyrene resin, an acrylonitrile-styrene copolymer resin, an acrylonitrile-butadiene copolymer, a polyvinyl acetate resin, a polyvinyl formal resin, a polysulfone resin, a styrene-butadiene copolymer resin, a vinylidene chloride-acrylonitrile copolymer resin, a vinyl chloride-vinyl acetate-maleic anhydride resin, a silicone resin, a phenol-formaldehyde resin, a polyacrylamide resin, a polyamide resin, a poly-N-vinylcarbazole resin, and the like. These binder resins may be used alone or used as a mixture of two or more kinds thereof.

The mixing ratio between the charge generating material and the binder resin is desirably in a range of from 10:1 to 1:10, for example.

For the formation of the charge generating layer, a coating liquid for forming a charge generating layer obtained by adding the above components in a solvent is used.

As a method of dispersing particles (for example, the charge generating material) in the coating liquid for forming a charge generating layer, a media dispersing machine such as a ball mill, a vibration ball mill, an attritor, a sand mill, or a horizontal sand mill; stirring; and a media-less dispersing machine such as an ultrasonic dispersing machine, a roll mill, or a high pressure homogenizer are used. Herein, examples of the high pressure homogenizer include a collision type which disperses a dispersion through liquid-to-liquid collision or liquid-to-wall collision in a high pressure state, a penetration type which disperses the dispersion by causing the dispersion to penetrate a fine flow path in a high pressure state, and the like.

Examples of a method of coating the coating liquid for forming a charge generating layer onto the undercoat layer include dip coating, push-up coating, wire bar coating, spray coating, blade coating, knife coating, curtain coating, and the like.

The film thickness of the charge generating layer is set desirably in a range of from 0.01 μm to 5 μm, and more desirably in a range of from 0.05 μm to 2.0 μm.

(Charge Transporting Layer)

The charge transporting layer is configured with a charge transporting material and optionally a binder resin.

Examples of the charge transporting material include oxadiazole derivative such as 2,5-bis(p-diethylaminophenyl)-1,3,4-oxadiazole; a pyrazoline derivative such as 1,3,5-triphenyl-pyrazoline or 1-[pyridyl-(2)]-3-(p-diethylaminostyryl)-5-(p-diethylamino styryl)pyrazoline; an aromatic tertiary amino compound such as triphenylamine, N,N'-bis(3,4-dimethylphenyl)biphenyl-4-amine, tri(p-methylphenyl)aminyl-4-amine, or dibenzylaniline; an aromatic tertiary diamino compound such as N,N'-bis(3-methylphenyl)-N,N'-diphenylbenzidine; a 1,2,4-triazine derivative such as 3-(4'-dimethylaminophenyl)-5,6-di-(4'-methoxyphenyl)-1,2,4-triazine; a hydrazone derivative such as 4-diethylaminobenzaldehyde-1,1-diphenylhydrazone; a quinazoline derivative such as 2-phenyl-4-styryl-quinazoline; a benzofuran derivative such as 6-hydroxy-2,3-di(p-methoxyphenyl)benzofuran; an α-stilbene derivative such as p-(2,2-diphenylvinyl)-N,N-diphenyl aniline; an enamine derivative; a carbazole derivative such as N-ethylcarbazole; hole transport materials such as poly-N-vinylcarbazole and a derivative thereof; a quinone-based compound such as chloranil or bromoanthraquinone; a tetracyanoquinodimethane-based compound; a fluorenone compound such as 2,4,7-trinitrofluorenone or 2,4,5,7-tetranitro-9-fluorenone; a xanthone-based compound; and an electron transport material such as a thiophene compound; and a polymer having a group including the above compounds in a main chain or a side chain thereof. These charge transport materials may be used alone or in combination of two or more kinds thereof.

Examples of the binder resin configuring the charge transporting layer include bisphenol A type or bisphenol Z type polycarbonate resin, an acrylic resin, a methacrylic resin, a polyarylate resin, a polyester resin, a polyvinyl chloride resin, a polystyrene resin, an acrylonitrile-styrene copolymer resin, an acrylonitrile-butadiene copolymer resin, a polyvinyl acetate resin, a polyvinyl formal resin, a polysulfone resin, a styrene-butadiene copolymer resin, a vinylidene chloride-acrylonitrile copolymer resin, a vinyl chloride-vinyl acetate-maleic anhydride resin, a silicone resin, a phenol-formaldehyde resin, a polyacrylamide resin, a polyamide resin, an insulating resin such as chlorinated rubber, an organic photoconductive polymer such as polyvinyl carbazole, polyvinyl anthracene, or polyvinyl pyrene, and the like. These binder resins may be used alone or used as a mixture of two or more kinds thereof.

The mixing ratio between the charge transporting material and the binder resin is desirably from 10:1 to 1:5, for example.

The charge transporting layer is formed using a coating liquid for forming a charge transporting layer obtained by adding the above components to a solvent.

As a method of dispersing particles (for example, fluororesin particles) in the coating liquid for forming a charge transporting layer, a media dispersing machine such as a ball mill, a vibration ball mill, an attritor, a sand mill, or a horizontal sand mill; stirring; and a media-less dispersing machine such as an ultrasonic dispersing machine, a roll mill, or a high pressure homogenizer are used. Examples of the high pressure homogenizer include a collision type which disperses a dispersion through liquid-to-liquid collision or liquid-to-wall collision in a high pressure state, a penetration type which disperses the dispersion by causing the dispersion to penetrate a fine flow path in a high pressure state, and the like.

As a method of coating the coating liquid for forming a charge transporting layer onto the charge generating layer, a general method such as dip coating, push-up coating, wire bar coating, spray coating, blade coating, knife coating, or curtain coating is used.

The film thickness of the charge transporting layer is set desirably in a range of from 5 μm 50 μm, and more desirably in a range of from 10 μm to 40 μm.

(Protective Layer)

The protective layer is a layer to which the charge transporting layer described above is applied, and contains a polymer of the compound represented by General Formula (I).

To form this protective layer, a charge transporting composition that contains the compound represented by General Formula (I) is used. The total content of the compound represented by General Formula (I) in the composition is, for example, desirably 40% by weight or more, more desirably 50% or more, and even more desirably 60% by weight or more, based on the charge transporting composition (total weight of solid contents excluding a solvent).

If the content is in this range, excellent electrical characteristics are obtained, and the thickness of the cured film is increased.

In the exemplary embodiment, the compound represented by General Formula (I) may be concurrently used with a known charge transporting material that does not have a reactive group. The known charge transporting material that does not have a reactive group does not have a reactive group which does not transport charge. Accordingly, this material is effective for further improving electrical characteristics by increasing component concentration of the charge transporting material.

As the known charge transporting material, those exemplified as the charge transporting material configuring the charge transporting layer are used.

Hereinafter, other components of the charge transporting composition for forming a protective layer will be described.

The charge transporting composition used for forming a protective layer may contain the following surfactant, in view of securing film formability.

For example, the surfactant includes one or more structures among (A) a structure formed by polymerizing acrylic monomers having a fluorine atom, (B) a structure having a carbon-carbon double bond and a fluorine atom, (C) an alkylene oxide structure, and (D) a structure having a carbon-carbon triple bond and a hydroxyl group, in a molecule.

This surfactant may contain one or two or more structures among structures (A) to (D), in a molecule.

Hereinafter, the structures (A) to (D) and the surfactants having these structures will be described.

(A) Structure Formed by Polymerizing Acrylic Monomers Having a Fluorine Atom

Though not particularly limited, the structure formed by polymerizing acrylic monomers having a fluorine atom is desirably a structure formed by polymerizing acrylic monomers having a fluoroalkyl group, and more desirably a structure formed by polymerizing acrylic monomers having a perfluoroalkyl group.

Specific examples of the surfactant having the (A) structure include Polyflow KL-600 (manufactured by KYOEISHA CHEMICAL Co., LTD), Eftop EF-351, Eftop EF-352, Eftop EF-801, Eftop EF-802, and Eftop EF-601 (manufactured by JEMCO, Inc.), and the like.

(B) Structure Having Carbon-Carbon Double Bond and Fluorine Atom

Though not particularly limited, the structure having a carbon-carbon double bond and a fluorine atom is desirably a group represented by at least any one of the following Structural Formulae (B1) and (B2).

(B1)

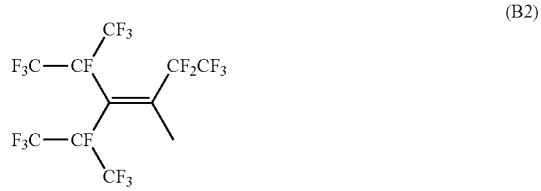

(B2)

The surfactant having the (B) structure is desirably a compound having a group represented by at least any one of Structural Formulae (B1) and (B2) in a side chain of an acrylic polymer, or a compound represented by any one of the following Structural Formulae (B3) to (B5).

When the surfactant having the (B) structure is a compound having at least any one of Structural Formulae (B1) and (B2) in a side chain of an acrylic polymer, the acrylic structure is easily mixed with other components in the composition, and accordingly, a uniform outermost surface layer may be formed.

When the surfactant having the (B) structure is a compound represented by any one of Structural Formulae (B3) to (B5), cissing caused during coating tends to be prevented, and accordingly, defects in a coating film may be inhibited.

(B3)

(B4)

(B5)

In Structural Formulae (B3) to (B5), each of v and w independently represents an integer of 1 or greater, R' represents a hydrogen atom or a monovalent organic group, and each Rf independently represents a group represented by Structural Formula (B1) or (B2).

In Structural Formulae (B3) to (B5), examples of the monovalent organic group represented by R' include an alkyl group having from 1 to 30 carbon atoms and a hydroxyalkyl group having from 1 to 30 carbon atoms.

Examples of commercially available products of the surfactant having the (B) structure include the following ones.

Examples of the compound represented by any one of Structural Formulae (B3) to (B5) includes Ftergent 100, Ftergent 100C, Ftergent 110, Ftergent 140A, Ftergent 150, Ftergent 150CH, Ftergent A-K, Ftergent 501, Ftergent 250, Ftergent 251, Ftergent 222F, Ftergent FTX-218, Ftergent 300, Ftergent 310, Ftergent 400SW, Ftergent 212M, Ftergent 245M, Ftergent 290M, Ftergent FTX-207S, Ftergent FTX-211S, Ftergent FTX-220S, Ftergent FTX-230S, Ftergent FTX-209F, Ftergent FTX-213F, Ftergent FTX-222F, Ftergent FTX-233F, Ftergent FTX-245F, Ftergent FTX-208G, Ftergent FTX-218G, Ftergent FTX-230G, Ftergent FTX-240G, Ftergent FTX-204D, Ftergent FTX-280D, Ftergent FTX-212D, Ftergent FTX-216D, Ftergent FTX-218D, Ftergent FTX-220D, Ftergent FTX-222D (manufactured by NEOS COMPANY LIMITED.), and the like.

Examples of the compound having at least any one of Structural Formulae (B1) and (B2) in a side chain of the acrylic polymer include KB-L82, KB-L85, KB-L97, KB-L109, KB-L110, KB-F2L, KB-F2M, KB-F2S, KB-F3M, KB-FaM (manufactured by NEOS COMPANY LIMITED.), and the like.

(C) Alkylene Oxide Structure (C) alkylene oxide structure includes alkylene oxide and polyalkylene oxide. Specifically, alkylene oxide includes ethylene oxide, propylene oxide, and the like. The alkylene oxide structure may be polyalkylene oxide in which the repeating number of the alkylene oxide is from 2 to 10000.

Examples of the surfactant having the (C) alkylene oxide structure include polyethylene glycol, a polyether antifoam agent, polyether-modified silicone oil, and the like.

The average molecular weight of the polyethylene glycol is desirably 2000 or less, and examples of the polyethylene glycol having an average molecular weight of 2000 or less include polyethylene glycol 2000 (average molecular weight of 2000), polyethylene glycol 600 (average molecular weight of 600), polyethylene glycol 400 (average molecular weight of 400), polyethylene glycol 200 (average molecular weight of 200), and the like.

In addition, polyether antifoam agents such as PE-M and PE-L (all manufactured by Wako Pure Chemical Industries, Ltd.) and antifoam agents No. 1 and No. 5 (all manufactured by Kao Corporation) are also exemplified as suitable examples.

Examples of the surfactant having a fluorine atom in a molecule in addition to the (C) alkylene oxide structure include a surfactant having alkylene oxide or polyalkylene oxide in a side chain of a polymer that has a fluorine atom, a surfactant in which the terminal of alkylene oxide or polyakylene oxide is substituted with a substituent that has a fluorine atom, and the like.

Specific examples of the surfactant having a fluorine atom in a molecule in addition to the (C) alkylene oxide structure include Megafac F-443, Megafac F-444, Megafac F-445, and Megafac F-446 (all manufactured by DIC Corporation), Ftergent 250, Ftergent 251, and Ftergent 222F (all manufactured by NEOS COMPANY LIMITED.), POLY FOX PF636, POLY FOX PF6320, POLY FOX PF6520, and POLY FOX PF656 (all manufactured by KITAMURA CHEMICALS CO., LTD.), and the like.

Specific examples of the surfactant having a silicone structure in a molecule in addition to the (C) alkylene oxide structure include KF351 (A), KF352 (A), KF353 (A), KF354 (A), KF355 (A), KF615 (A), KF618, KF945 (A), and KF6004 (all manufactured by Shin-Etsu Chemical Co., Ltd.), TSF4440, TSF4445, TSF4450, TSF4446, TSF4452, TSF4453, and TSF4460 (all manufactured by GE Toshiba Silicones, Co., Ltd.), BYK-300, BYK-302, BYK-306, BYK-307, BYK-310, BYK-315, BYK-320, BYK-322, BYK-323, BYK-325, BYK-330, BYK-331, BYK-333, BYK-337, BYK-341, BYK-344, BYK-345, BYK-346, BYK-347, BYK-348, BYK-370, BYK-375, BYK-377, BYK-378, UV3500, UV3510, and UV3570 (all manufactured by BYK-Chemie Japan KK), and the like.

(D) Structure Having Carbon-Carbon Triple Bond and Hydroxyl Group (D) structure having a carbon-carbon triple bond and a hydroxyl group is not particularly limited, and examples of the surfactant having this structure include the following compounds.

Examples of the surfactant having the (D) structure including a carbon-carbon triple bond and a hydroxyl group include a compound having a triple bond and a hydroxyl group in a molecule, and specific examples thereof include 2-propyn-1-ol, 1-butyn-3-ol, 2-butyn-1-ol, 3-butyn-1-ol, 1-pentyn-3-ol, 2-pentyn-1-ol, 3-pentyn-1-ol, 4-pentyn-1-ol, 4-pentyn-2-ol, 1-hexyn-3-ol, 2-hexyn-1-ol, 3-hexyn-1-ol, 5-hexyn-1-ol, 5-hexyn-3-ol, 1-heptyn-3-ol, 2-heptyn-1-ol, 3-heptyn-1-ol, 4-heptyn-2-ol, 5-heptyn-3-ol, 1-octyn-3-ol, 3-octyn-1-ol, 3-nonyn-1-ol, 2-decyn-1-ol, 3-decyn-1-ol, 10-undecyn-1-ol, 3-methyl-1-butyn-3-ol, 3-methyl-1-penten-4-yn-3-ol, 3-methyl-1-pentyn-3-ol, 5-methyl-1-hexyn-3-ol, 3-ethyl-1-pentyn-3-ol, 3-ethyl-1-heptyn-3-ol, 4-ethyl-1-octyn-3-ol, 3,4-dimethyl-1-pentyn-3-ol, 3,5-dimethyl-1-hexyn-3-ol, 3,6-dimethyl-1-heptyn-3-ol, 2,2,8,8-tetramethyl-3,6-nonadiyn-5-ol, 4,6-nonadecadiyn-1-ol, 10,12-pentacosadiyn-1-ol, 2-butyne-1,4-diol, 3-hexyne-2,5-diol, 2,4-hexadiyne-1,6-diol, 2,5-dimethyl-3-hexyne-2,5-diol, 3,6-dimethyl-4-octyne-3,6-diol, 2,4,7,9-tetramethyl-5-decyne-4,7-diol, (+)-1,6-bis(2-chlorophenyl)-1,6-diphenyl-2,4-hexadiyne-1,6-diol, (−)-1,6-bis(2-chlorophenyl)-1,6-diphenyl-2,4-hexadiyne-1,6-diol, 2-butyne-1,4-diol bis(2-hydroxyethyl), 1,4-diacetoxy-2-butyne, 4-diethylamino-2-butyn-1-ol, 1,1-diphenyl-2-propyn-1-ol, 1-ethynyl-1-cyclohexanol, 9-ethynyl-9-fluorenol, 2,4-hexadiynediyl-1,6-bis(4-phenylazobenzenesulfonate), 2-hydroxy-3-butynic acid, 2-hydroxy-3-butynic acid ethyl ester, 2-methyl-4-phenyl-3-butyn-2-ol, methyl propargyl ether, 5-phenyl-4-pentyn-1-ol, 1-phenyl-1-propyn-3-ol, 1-phenyl-2-propyn-1-ol, 4-trimethylsilyl-3-butyn-2-ol, 3-trimethylsilyl-2-propyn-1-ol, and the like.

The examples also include a compound (for example a Surfynol 400 series (manufactured by Shin-Etsu Chemical Co., Ltd.)) obtained by adding alkylene oxide such as ethylene oxide to a portion or all of hydroxyl groups in the above compound, and the like.

As the surfactant having the (D) structure including a carbon-carbon triple bond and a hydroxyl group, compounds represented by any one of the following General Formulae (D1) and (D2) are desirable.

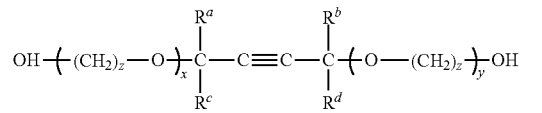

(D1)

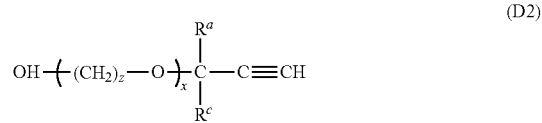

(D2)

In General Formulae (D1) and (D2), each of $R^a$, $R^b$, $R^c$, and $R^d$ independently represents a monovalent organic group, and each of x, y, and z independently represents an integer of 1 or greater.

Among the compounds represented by General Formula (D1) or (D2), compounds in which $R^a$, $R^b$, $R^c$, and $R^d$ are alkyl groups are desirable, and compounds in which at least one of $R^a$ and $R^b$ and at least one of $R^c$ and $R^d$ are branched alkyl groups are more desirable. z is desirably from 1 to 10, and each of x and y is desirably from 1 to 500.

Examples of commercially available products of the compound represented by General Formula (D1) or (D2) include a Surfynol 400 series (manufactured by Shin-Etsu Chemical Co., Ltd.).

The surfactant having the structure of (A) to (D) described above may be used alone or used as a mixture of plural kinds thereof. When the surfactant is used as a mixture of plural kinds thereof, a surfactant having a structure differing from that of the surfactant having the structure of (A) to (D) may be concurrently used, within a range that does not impair the effect of the exemplary embodiment.

Examples of the surfactant that may be concurrently used include the following surfactants having a fluorine atom and surfactants having a silicone structure.

That is, suitable examples of the surfactant that has a fluorine atom and may be concurrently used with the surfactant having the structure of (A) to (D) include perfluoroalkyl sulfonic acids (for example, perfluorobutane sulfonic acid, perfluorooctane sulfonic acid, and the like), perfluoroalkyl carboxylic acids (for example, perfluorobutane carboxylic acid, perfluorooctane carboxylic acid, and the like), and perfluoroalkyl group-containing phosphoric acid ester. The perfluoroalkyl sulfonic acids and perfluoroalkyl carboxylic acids may be a salt thereof and an amide-modified product thereof.

Examples of commercially available products of the perfluoroalkyl sulfonic acids include Megafac F-114 (manufactured by DIC Corporation), Eftop EF-101, Eftop EF-102, Eftop EF-103, Eftop EF-104, Eftop EF-105, Eftop EF-112, Eftop EF-121, Eftop EF-122A, Eftop EF-122B, Eftop EF-122C, and Eftop EF-123A (all manufactured by JEMCO, Inc.), Ftergent 100, Ftergent 100C, Ftergent 110, Ftergent 140A, Ftergent 150, Ftergent 150CH, Ftergent A-K, and Ftergent 501 (all manufactured by NEOS COMPANY LIMITED.), and the like.

Examples of commercially available products of the perfluoroalkyl carboxylic acids include Megafac F-410 (manufactured by DIC Corporation), Eftop EF-201 and Eftop EF-204 (all manufactured by JEMCO, Inc.), and the like.

Examples of commercially available products of the perfluoroalkyl group-containing phosphoric acid ester include Megafac F-493 and Megafac F-494 (manufactured by DIC Corporation), Eftop EF-123A, Eftop EF-123B, Eftop EF-125M, and Eftop EF-132 (manufactured by JEMCO, Inc.), and the like.

The surfactant that has a fluorine atom and may be concurrently used with the surfactant having the structure of (A) to (D) is not limited to the above-described surfactants. For example, a fluorine atom-containing compound having a betaine structure (for example, Ftergent 400SW manufactured by NEOS COMPANY LIMITED.) and a surfactant having an amphoteric ion group (for example, Ftergent SW manufactured by NEOS COMPANY LIMITED.) are also suitably used as the surfactant.

Examples of the surfactant that has a silicone structure and may be concurrently used with the surfactant having the structure of (A) to (D) include general silicone oil such as dimethyl silicone, methyl phenyl silicone, diphenyl silicone, or a derivative thereof.

The content of the surfactant is desirably from 0.01% by weight to 1% by weight, and more desirably from 0.02% by weight to 0.5% by weight, based on the charge transporting composition (total weight of solid content excluding a solvent). If the content of the surfactant is less than 0.01% by weight, the effect of preventing defects in coating film tends to be insufficient. If the content of the surfactant exceeds 1% by weight, the surfactant and curing components (compound represented by General Formula (I) and another monomer, oligomer, and the like) are separated from each other, and consequently, the strength of the obtained cured film tends to be reduced.

In addition, among all surfactants, the surfactant having the structure of (A) to (D) is contained in the composition desirably at 1% by weight or more, and more desirably at 10% by weight or more.

For the purpose of controlling the viscosity of the composition and the strength, flexibility, smoothness, a cleaning property, and the like of the film, a radical-polymerizable monomer, oligomer, or the like that does not have a charge transport function may be added to the charge transporting composition used for forming a protective layer.

Examples of a monofunctional radical-polymerizable monomer include isobutyl acrylate, t-butyl acrylate, isooctyl acrylate, lauryl acrylate, stearyl acrylate, isobornyl acrylate, cyclohexyl acrylate, 2-methoxyethyl acrylate, methoxy triethylene glycol acrylate, 2-ethoxyethyl acrylate, tetrahydrofurfuryl acrylate, benzyl acrylate, ethyl carbitol acrylate, phenoxyethyl acrylate, 2-hydroxy acrylate, 2-hydroxypropyl acrylate, 4-hydroxybutyl acrylate, methoxy polyethylene glycol acrylate, methoxy polyethylene glycol methacrylate, phenoxy polyethylene glycol acrylate, phenoxy polyethylene glycol methacrylate, hydroxyethyl o-phenyl phenol acrylate, o-phenyl phenol glycidyl ether acrylate, and the like.

Examples of a bifunctional radical-polymerizable monomer include 1,4-butanediol diacrylate, 1,6-hexanediol diacrylate, 1,9-nonanediol diacrylate, 2-n-butyl-2-ethyl-1,3-propanediol diacrylate, tripropylene glycol diacrylate, tetraethylene glycol diacrylate, dioxane glycol diacrylate, polytetramethylene glycol diacrylate, ethoxylated bisphenol A diacrylate, ethoxylated bisphenol A dimethacrylate, tricyclodecane methanol diacrylate, tricyclodecane methanol dimethacrylate, and the like.

Examples of a tri- or higher functional radical-polymerizable monomer include trimethylolpropane triacrylate, trimethylolpropane trimethacrylate, pentaerythritol acrylate, trimethylolpropane EO-added triacrylate, glycerin PO-added triacrylate, trisacryloyloxy ethyl phosphate, pentaerythritol tetraacrylate, ethoxylated isocyanur triacrylate, and the like.

Examples of a radical-polymerizable oligomer include oligomers based on epoxy acrylate, urethane acrylate, and polyester acrylate.

The radical-polymerizable monomer or oligomer that does not have a charge transport function is contained in the composition desirably at from 0% by weight to 50% by weight, more desirably at from 0% by weight to 40% by weight, and even more desirably at from 0% by weight to 30% by weight, based on the charge transporting composition (total weight of solid contents excluding a solvent).

It is desirable to include a thermal radical generator or a derivative thereof in the charge transporting composition used for forming a protective layer. That is, a protective layer desirably includes a thermal radical generator or a derivative thereof.

Herein, the "derivative of a thermal radical generator" refers to a reaction residue remaining after radical is generated by heat or a substance formed when a radical active species bind to a polymer terminal.

The cured film (crosslinked film) configuring a protective layer is obtained by curing the charge transporting composition that contains the respective components described above through various methods such as heat, light, and electron beams. However, in order to keep the balance between characteristics such as electrical characteristics and mechanical strength of the cured film, thermal curing is desirable. Usually, when a general acrylic coating material or the like is cured, electron beams that may cure the material without using a catalyst or photopolymerization that may cure the material in a short time is suitably used. However, in an electrophotographic photoreceptor, since a photosensitive layer, which is the surface to be formed, of an outermost surface layer contains photosensitive materials, it is desirable to perform thermal curing in which the reaction proceeds slowly, in order that the photosensitive materials are not easily damaged and that the surface properties of the obtained cured film are improved.

Consequently, the thermal curing may be performed without a catalyst, but it is desirable to use the above-described thermal radical generator or a derivative thereof as a catalyst. In this manner, the occurrence of ghost caused by repeated use is easily inhibited.

The thermal radical generator or a derivative thereof is not limited. However, in order to inhibit the photosensitive materials in the photosensitive layer from being damaged during the formation of a protective layer, the thermal radical generator is desirably the one having a 10-hour half life temperature of from 40° C. to 110° C.

Examples of commercially available products of the thermal radical generator include azo-based initiators such as V-30, (10-hour half life temperature: 104° C.), V-40 (10-hour half life temperature: 88° C.), V-59 (10-hour half life temperature: 67° C.), V-601 (10-hour half life temperature: 66° C.), V-65 (10-hour half life temperature: 51° C.), V-70 (10-hour half life temperature: 30° C.), VF-096 (10-hour half life temperature: 96° C.), Vam-110 (10-hour half life temperature: 111° C.), Vam-111 (10-hour half life temperature: 111° C.), VE-073 (10-hour half life temperature: 73° C.) (all manufactured by Wako Pure Chemical Industries, Ltd.), $OT_{AZO}$-15 (10-hour half life temperature: 61° C.), $OT_{AZO}$-30 (10-hour half life temperature: 57° C.) AIBN (10-hour half life temperature: 65° C.), AMBN (10-hour half life temperature: 67° C.), ADVN (10-hour half life temperature: 52° C.), and ACVA (10-hour half life temperature: 68° C.) (all manufactured by Otsuka Chemical Co., Ltd.); Pertetra A, Perhexa HC, Perhexa C, Perhexa V, Perhexa 22, Perhexa MC, Perbutyl H, Percumyl H, Percumyl P, Permenta H, Perocta H, Perbutyl C, Perbutyl D, Perhexyl D, Peroyl IB, Peroyl 355, Peroyl L, Peroyl SA, Nyper BW, Nyper BMT-K40/M, Peroyl IPP, Peroyl NPP, Peroyl TCP, Peroyl OPP, Peroyl SBP, Percumyl ND, Perocta ND, Perhexyl ND, Perbutyl ND, Perbutyl NHP, Perhexyl PV, Perbutyl PV, Perhexa 250, Perocta O, Perhexyl o, Perbutyl O, Perbutyl L, Perbutyl 355, Perhexyl I, Perbutyl I, Perbutyl E, Perhexa 25Z, Perbutyl A, Perhexyl Z, Perbutyl ZT, and Perbutyl Z (all manufactured by NOF CORPORATION); Kayaketal AM-055, Trigonox 36-C75, Laurox, Perkadox L-W75, Perkadox CH-50L, Trigonox TMBH, Kayacumene H, Kayabutyl H-70, Perkadox BC-FF, Kayahexa AD, Perkadox 14, Kayabutyl C, Kayabutyl D, Kayahexa YD-E85, Perkadox 12-XL25, Perkadox 12-EB20, Trigonox 22-N70, Trigonox 22-70E, Trigonox D-T50, Trigonox 423-C70, Kayaester CND-C70, Kayaester CND-W50, Trigonox 23-C70, Trigonox 23-W50N, Trigonox 257-C70, Kayaester P-70, Kayaester TMPO-70, Trigonox 121, Kayaester O, Kayaester HTP-65W, Kayaester AN, Trigonox 42, Trigonox F-050, Kayabutyl B, Kayacarbon EH-C70, Kayacarbon EH-W60, Kayacarbon I-20, Kayacarbon BIC-75, Trigonox 117, and Kayalene 6-70 (all manufactured by KAYA AKZO CO., LTD.); Luperox LP (10-hour half life temperature: 64° C.), Luperox 610 (10-hour half life temperature: 37° C.), Luperox 188 (10-hour half life temperature: 38° C.), Luperox 844 (10-hour half life temperature: 44° C.), Luperox 259 (10-hour half life temperature: 46° C.), Luperox 10 (10-hour half life temperature: 48° C.), Luperox 701 (10-hour half life temperature: 53° C.), Luperox 11 (10-hour half life temperature: 58° C.), Luperox 26 (10-hour half life temperature: 77° C.), Luperox 80 (10-hour half life temperature: 82° C.), Luperox 7 (10-hour half life temperature: 102° C.), Luperox 270 (10-hour half life temperature: 102° C.), Luperox P (10-hour half life temperature: 104° C.), Luperox 546 (10-hour half life temperature: 46° C.), Luperox 554 (10-hour half life temperature: 55° C.), Luperox 575 (10-hour half life temperature: 75° C.), Luperox TANPO (10-hour half life temperature: 96° C.), Luperox 555 (10-hour half life temperature: 100° C.), Luperox 570 (10-hour half life temperature: 96° C.), Luperox TAP (10-hour half life temperature: 100° C.), Luperox TBIC (10-hour half life temperature: 99° C.), Luperox TBEC (10-hour half life temperature: 100° C.), Luperox JW (10-hour half life temperature: 100° C.), Luperox TAIC (10-hour half life temperature: 96° C.), Luperox TAEC (10-hour half life temperature: 99° C.), Luperox DC (10-hour half life temperature: 117° C.), Luperox 101 (10-hour half life temperature: 120° C.), Luperox F (10-hour half life temperature: 116° C.), Luperox D1 (10-hour half life temperature: 129° C.), Luperox 130 (10-hour half life temperature: 131° C.), Luperox 220 (10-hour half life temperature: 107° C.), Luperox 230 (10-hour half life temperature: 109° C.), Luperox 233 (10-hour half life temperature: 114° C.), and Luperox 531 (10-hour half life temperature: 93° C.) (all manufactured by ARKEMA YOSHITOMI, LTD.); and the like.

The thermal radical generator or a derivative thereof is contained in the composition desirably at from 0.001% by weight to 10% by weight, more desirably at from 0.01% by weight to 5% by weight, and even more desirably at from 0.1% by weight to 3% by weight, based on the reactive compound (compound represented by General Formula (I)+ other reactive compounds) in the charge transporting composition.

To the charge transporting composition used for forming a protective layer, other thermosetting resins such as a phenol resin, a melamine resin, and a benzoguanamine resin may be added, in order that oxidation caused by gas generated by discharge is effectively inhibited by these resins which are added to keep the composition from adsorbing too much gas generated by discharge.

In addition, for the purpose of adjusting formability, flexibility, smoothness, and adhesiveness of the film, a coupling agent, a hard coating agent, and a fluorine-containing compound may be further added to the charge transporting composition used for forming a protective layer. Specifically, as these additives, various silane coupling agents and commercially available silicone-based hard coating agents are used.

As the silane coupling agents, vinyl trichlorosilane, vinyl trimethoxysilane, vinyl triethoxysilane, γ-glycidoxypropyl methyl diethoxysilane, γ-glycidoxypropyl trimethoxysilane, γ-aminopropyl triethoxysilane, γ-aminopropyl trimethoxysilane, γ-aminopropyl methyl dimethoxysilane, N-β(aminoethyl) γ-aminopropyl triethoxysilane, tetramethoxysilane, methyltrimethoxysilane, dimethyl dimethoxysilane, and the like are used.

As the commercially available hard coating agents, KP-85, X-40-9740, and X-8239 (all manufactured by ShinEtsu Silicones); AY42-440, AY42-441, and AY49-208 (all manufactured by Dow Corning Toray); and the like are used.

In addition, in order to impart water repellency or the like, fluorine-containing compounds such as (tridecafluoro-1,1,2,2-tetrahydrooctyl) triethoxysilane, (3,3,3-trifluoropropyl)trimethoxysilane, 3-(heptafluoroisopropoxy)propyl triethoxysilane, 1H,1H,2H,2H-perfluoroalkyl triethoxysilane, 1H,1H,2H,2H-perfluorodecyl triethoxysilane, and 1H,1H,2H,2H-perfluoroctyl triethoxysilane may also be added.

The silane coupling agent is used in an arbitrary amount, but the amount of the fluorine-containing compound is desirably 0.25 time or less of the compound not containing fluorine in terms of a weight ratio. If the amount of the silane coupling agent used exceeds this amount, the formability of the crosslinked film becomes problematic in some cases.

For the purposes of adjusting the discharge gas resistance, mechanical strength, and damage resistance of the protective layer, reducing torque, controlling abrasion loss, and extending pot life, or for the purposes of controlling particle dispersibility and viscosity, a thermoplastic resin may be added to the charge transporting composition used for forming a protective layer.

Examples of the thermoplastic resin include a polyvinyl butyral resin, a polyvinyl formal resin, a polyvinyl acetal resin (for example S-LEC B, K, and the like manufactured by SEKISUI CHEMICAL CO., LTD.) such as a partially acetalized polyvinyl acetal resin obtained when a portion of butyral is modified with formal, acetoacetal, or the like, a polyamide resin, a cellulose resin, a polyvinyl phenol resin, and the like.

Particularly, in view of electrical characteristics, a polyvinyl acetal resin and a polyvinyl phenol resin are desirable. The weight average molecular weight of the resin is desirably from 2,000 to 100,000, and more desirably from 5,000 to 50,000. If the molecular weight of the resin is less than 2,000, the effect produced by the addition of the resin tends to be insufficient. If the molecular weight exceeds 100,000, solubility decreases, the amount of the resin added is restricted, and a defective film tends to be formed when the composition is coated. The amount of the resin added is desirably from 1% by weight to 40% by weight, more desirably from 1% by weight to 30% by weight, and even more desirably from 5% by weight to 20% by weight. If the amount of the resin added is less than 1% by weight, the effect produced by the addition of the resin tends to be insufficient, and if it exceeds 40% by weight, image blurring easily occurs at a high temperature and high humidity (for example, 28° C. and 85% RH).

For the purpose of preventing the deterioration of the protective layer caused by oxidizing gas such as ozone which is generated by a charging device, it is desirable to add an antioxidant to the charge transporting composition used for forming a protective layer. If the mechanical strength of the photoreceptor surface increases, and the life of the photoreceptor is extended, the photoreceptor contacts the oxidizing gas for a long time. Accordingly, oxidation resistance stronger than that in the related art is required.

As the antioxidant, antioxidants based on hindered phenol or hindered amine are desirable, and known antioxidants such as an organic sulfur-based antioxidant, a phosphite-based antioxidant, a dithiocarbamic acid salt-based antioxidant, a thiourea-based antioxidant, and a benzimidazole-based antioxidant may also be used. The amount of the antioxidant added is desirably 20% by weight or less, and more desirably 10% by weight or less.

Examples of the hindered phenol-based antioxidant include 2,6-di-t-butyl-4-methylphenol, 2,5-di-t-butylhydroquinone, N,N'-hexamethylenebis (3,5-di-t-butyl-4-hydroxyhydrocinnamide, 3,5-di-t-butyl-4-hydroxy-benzylphosphonate-diethyl ester, 2,4-bis[(octylthio)methyl]-o-cresol, 2,6-di-t-butyl-4-ethylphenol, 2,2'-methylenebis(4-methyl-6-t-butylphenol), 2,2'-methylenebis(4-ethyl-6-t-butylphenol), 4,4'-butylidenebis(3-methyl-6-t-butylphenol), 2,5-di-t-amylhydroquinone, 2-t-butyl-6-(3-butyl-2-hydroxy-5-methylbenzyl)-4-methylphenyl acrylate, 4,4'-butylidenebis (3-methyl-6-t-butylphenol), and the like.

For the purpose of decreasing the residual potential of a protective layer or improving the strength of a protective layer, various particles may be added to the charge transporting composition used for forming a protective layer.

An example of the particles includes silicon-containing particles. The silicon-containing particles are particles containing silicon as a constituent element, and specific examples thereof include colloidal silica, silicone particles, and the like. The colloidal silica used as the silicon-containing particles is selected from those obtained by dispersing silica having an average particle size of from 1 nm to 100 nm and desirably from 10 nm to 30 nm in an organic solvent such as an acidic or alkaline aqueous dispersion, an alcohol, a ketone, or an ester, and commercially available general colloidal silica may also be used. The solid content of the colloidal silica in the protective layer is not particularly limited. However, the colloidal silica is used in a range of from 0.1% by weight to 50% by weight, and desirably in a range of from 0.1% by weight to 30% by weight, based on the charge transporting composition (total weight of solid contents excluding a solvent), in respect of film formability, electrical characteristics, and strength.

The silicone particles used as the silicon-containing particles are selected from silicone resin particles, silicone rubber particles, and silica particles that are surface-treated with silicone, and commercially available general silicone particles are used. These silicone particles are spherical, and the average particle size thereof is desirably from 1 nm to 500 nm, and more desirably from 10 nm to 100 nm. The silicone particles are small size particles that are chemically inactive and have excellent dispersibility with a resin. The amount of the silicone particles added that is required for obtaining more sufficient characteristics is small. Accordingly, the surface properties of the electrophotographic photoreceptor are improved without hindering a crosslinking reaction. That is, while these particles are incorporated in a strong crosslinked structure without variation, the lubricity and water repellency of the electrophotographic photoreceptor surface are improved, and excellent abrasion resistance and a contaminant-repelling property are maintained over a long time.

The content of the silicone particles in the protective layer is desirably from 0.1% by weight to 30% by weight, and more desirably from 0.5% by weight to 10% by weight, based on the charge transporting composition (total weight of solid contents excluding a solvent).

Examples of other particles include fluorine-based particles such as tetrafluoroethylene, trifluoroethylene, hexafluoropropylene, vinyl fluoride, vinylidene fluoride; particles including a resin that is obtained by copolymerizing a fluororesin with a monomer having a hydroxyl group, as disclosed in "Proceedings of the 8$^{th}$ Polymer Material Forum, p. 89"; and semiconductive metallic oxides such as ZnO—$Al_2O_3$, $SnO_2$—$Sb_2O_3$, $In_2O_3$—$SnO_2$, $ZnO_2$—$TiO_2$, ZnO—$TiO_2$, MgO—$Al_2O_3$, FeO—$TiO_2$, $TiO_2$, $SnO_2$, $In_2O_3$, ZnO, and MgO. For the same purpose as described above, oil such as silicone oil may be added. Examples of the silicone oil include silicone oil such as dimethyl polysiloxane, diphenyl polysiloxane, or phenyl methyl siloxane; reactive silicone oil such as amino-modified polysiloxane, epoxy-modified polysiloxane, carboxyl-modified polysiloxane, carbinol-modified polysiloxane, methacryl-modified polysiloxane, mercapto-modified polysiloxane, or phenol-modified polysiloxane; cyclic dimethyl cyclosiloxanes such as hexamethyl cyclotrisiloxane, octamethyl cyclotetrasiloxane, decamethyl cyclopentasiloxane, and dodecamethyl cyclohexasiloxane; cyclic methylphenyl cyclosiloxanes such as 1,3,5-trimethyl-1,3,5-triphenyl cyclotrisiloxane, 1,3,5,7-tetramethyl-1,3,5,7-tetraphenyl cyclotetrasiloxane, and 1,3,5,7,9-pentamethyl-1,3,5,7,9-pentaphenyl cyclopentasiloxane; cyclic phenyl cyclosiloxanes such as hexaphenyl cyclotrisiloxane; fluorine-containing cyclosiloxanes such as (3,3,3-trifluoropropyl)methyl cyclotrisiloxane; hydrosilyl group-containing cyclosiloxanes such as a methyl hydrosiloxane mixture, pentamethyl cyclopentasiloxane, and phenyl hydrocyclosiloxane; vinyl group-containing cyclosiloxanes such as pentavinyl pentamethyl cyclopentasiloxane; and the like.

A metal, metallic oxide, carbon black, and the like may also be added to the charge transporting composition used for forming a protective layer. Examples of the metal include aluminum, zinc, copper, chromium, nickel, silver and stainless steel, or those obtained by vapor-depositing these metals onto the surface of plastic particles. Examples of the metallic oxide include zinc oxide, titanium oxide, tin oxide, antimony oxide, indium oxide, bismuth oxide, indium oxide doped with tin, tin oxide doped with antimony or tantalum, zirconium oxide doped with antimony, and the like. These metallic oxides may be used alone or in combination of two or more kinds thereof. When used in combination of two or more kinds thereof, the metallic oxide may be simply mixed, or may be used in the form of a solid solution or may be melted. The average particle size of the conductive particles is 0.3 μm or less, and particularly desirably 0.1 μm or less, in view of the transparency of the protective layer.

The charge transporting composition used for forming a protective layer is desirably prepared as a coating liquid for forming a protective layer. This coating liquid for forming a protective layer may be free of a solvent, or if necessary, this coating liquid may contain a solvent including alcohols such as methanol, ethanol, propanol, butanol, cyclopentanol, cyclohexanol; ketones such as acetone and methyl ethyl ketone; ethers such as tetrahydrofuran, diethyl ether, and dioxane; and the like.

These solvents may be used alone or used as a mixture of two or more kinds thereof, and a boiling point of the solvent is desirably 100° C. or lower. As the solvent, it is particularly desirable to use a solvent (for example, alcohols) having at least one or more kinds of hydroxyl group.

The coating liquid used for forming a protective layer that contains the charge transporting composition used for forming a protective layer is coated onto the charge transporting layer by general methods such as blade coating, wire bar coating, spray coating, dip coating, bead coating, air knife coating, and curtain coating, and polymerized (cured) if necessary by being heated at, for example, from 100° C. to 170° C., thereby obtaining a film. In this manner, a protective layer including this film is obtained.

The oxygen concentration in the coating liquid for forming a protective layer during polymerizing (curing) is desirably 1% or less, more desirably 1000 ppm or less, and even more desirably 500 ppm or less.

So far, as an electrophotographic photoreceptor, a functional separation type has been described, for example. The content of the charge generating material in the single layer type photosensitive layer 6 (charge generating/charge transporting layer) shown in FIG. 2 is from 10% by weight to 85% by weight, and desirably from 20% by weight to 50% by weight. The content of the charge transporting material is desirably from 5% by weight to 50% by weight. The method of forming the single layer type photosensitive layer 6 (charge generating/charge transporting layer) is the same as the method of forming the charge generating layer and the charge transporting layer. The film thickness of the single layer type photosensitive layer (charge generating/charge transporting layer) 6 is desirably from 5 μm to 50 μm, and more desirably from 10 μm to 40 μm.

In the exemplary embodiment, an embodiment in which the outermost surface layer including the charge transporting layer described above is a protective layer has been described. However, when there is no protective layer in the layer configuration, the charge transporting layer positioned at the uppermost surface in the layer configuration becomes the outermost surface layer, and the charge-transportable layer may be applied to the outermost surface layer.

In addition, even if there is a protective layer, the charge transporting layer described above may be applied as a charge transporting layer below the protective layer.

[Image Forming Apparatus/Process Cartridge]

Figure 4:
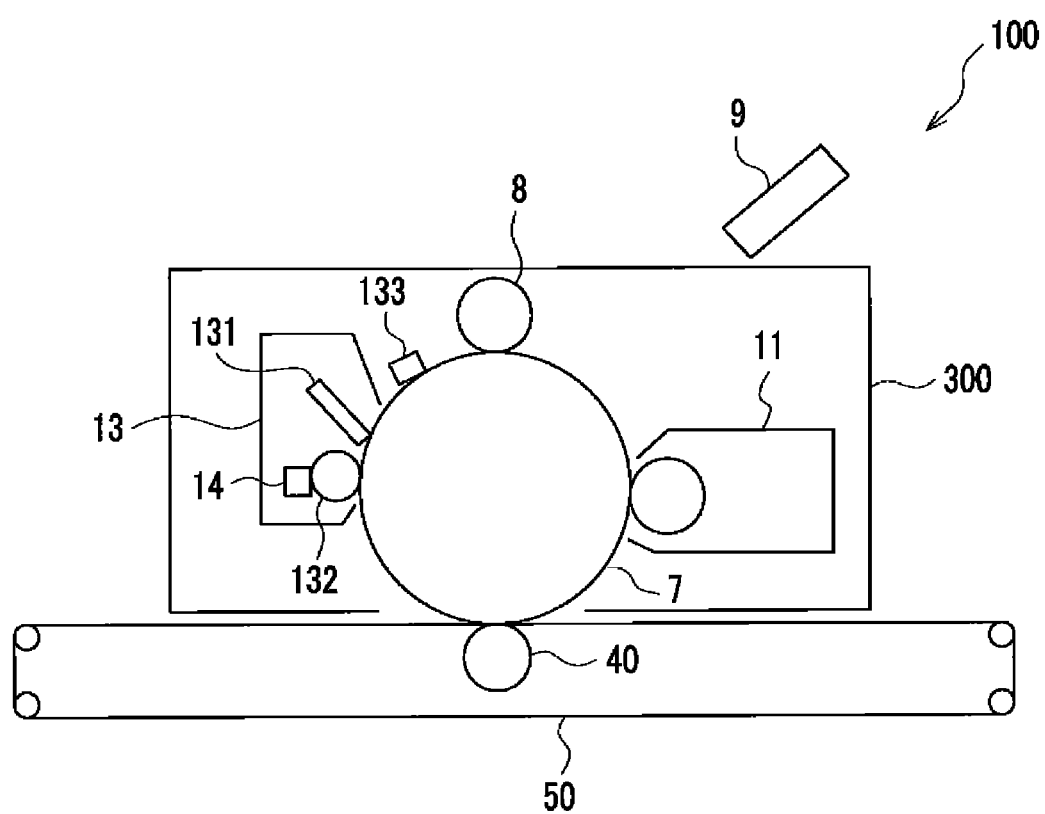
FIG. 4 is a schematic configuration view showing an image forming apparatus according to an exemplary embodiment.

FIG. 4 is a schematic configuration view showing an image forming apparatus 100 according to the embodiment.

The image forming apparatus 100 shown in FIG. 4 includes a process cartridge 300 provided with an electrophotographic photoreceptor 7, an exposure device (electrostatic latent image forming unit) 9, a transfer device (transfer unit) 40, and an intermediate transfer member 50. In the image forming apparatus 100, the exposure device 9 is disposed in a position for exposing the electrophotographic photoreceptor 7 through an opening portion of the process cartridge 300, the transfer device 40 is disposed in a position where the transfer device 40 faces the electrophotographic photoreceptor 7 across the intermediate transfer member 50, and the intermediate transfer member 50 is disposed while bringing a portion thereof into contact with the electrophotographic photoreceptor 7.

Herein, as the electrophotographic photoreceptor 7, the above-described electrophotographic photoreceptor according to the exemplary embodiment is used. As described above, in the electrophotographic photoreceptor according to the exemplary embodiment, the deterioration of electrical characteristics is inhibited even if the electrophotographic photoreceptor is repeatedly used for a long time. Accordingly, a process cartridge and an image forming apparatus including this electrophotographic photoreceptor may provide stabilized images for a long time.

The process cartridge 300 in FIG. 4 integrally supports the electrophotographic photoreceptor 7, a charging device (charging unit) 8, a developing device (developing unit) 11, and a cleaning device 13 inside a housing. The cleaning device 13 includes a cleaning blade (cleaning member), and a cleaning blade 131 is disposed so as to contact the surface of the electrophotographic photoreceptor 7.

The process cartridge 300 is not particularly limited as long as the process cartridge 300 includes the electrophotographic photoreceptor 7 and is configured so as to be detachable from an image forming apparatus. If necessary, the process cartridge 300 may be configured so as to integrally supports a device (for example, a device selected from the charging device (charging unit) 8, the developing device (developing unit) 11, and the cleaning device 13) other than the electrophotographic photoreceptor 7 with the electrophotographic photoreceptor 7.

FIG. 4 shows an example that includes fibrous member 132 (roll shape) supplying a lubricant 14 to the surface of the photoreceptor 7 as the cleaning device 13, and uses a fibrous member 133 (flat brush shape) assisting cleaning, but these members are optionally used.

As the charging device 8, for example, a contact type charging device using a conductive or semiconductive charging roll, a charging brush, a charging film, a charging rubber blade, a charging tube, or the like is used. In addition, known charging devices such as a non-contact type of roll charging device, a scorotron charging device using corona discharge, and a corotron charging device may also be used.

Though not shown in the drawing, a photoreceptor heating member for increasing the temperature of the electrophotographic photoreceptor 7 and reducing a relative temperature is provided around the electrophotographic photoreceptor 7 so as to heighten the image stability.

Examples of the exposure device 9 include an optical system instrument or the like that exposes a desired image with light such as a semiconductor laser beam, LED light, or liquid crystal shutter light on the surface of the electrophotographic photoreceptor 7. As the wavelength of a light source, wavelengths in a spectrophotometric region of the photoreceptor are used. As the wavelength of the semiconductor laser, near infrared having an oscillation wavelength near 780 nm is used in most cases. However, the wavelength is not limited thereto, and lasers such as a laser having an oscillation wavelength of about 600 nm and a blue laser having an oscillation wavelength near from 400 nm to 450 nm may also be used. In addition, in order to form color images, a surface-emitting type of laser beam source which realizes multi-beam output is also effective.

As the developing device 11, for example, a general developing device may be used which performs developing by bringing or not brining a magnetic or non-magnetic single- or two-component developer or the like into contact with the photoreceptor. The developing device is not particularly limited as long as it has the function described above, and is selected according to purposes. For example, a known developing device or the like is used which has a function of attaching the single- or two-component developer to the photoreceptor 7 by using a brush, a roll, or the like. Among these, a developing device that uses a developing roll holding the developer on the surface thereof is desirable.

Examples of the transfer device 40 include known transfer charging devices such as a contact-type transfer charging device using a belt, a roll, a film, a rubber blade, or the like, a scorotron transfer charging device using corona discharge, and a corotron transfer charging device.

As the intermediate transfer member 50, semiconductivity-imparted polyimide, polyamideimide, polycarbonate, polyarylate, polyester, or rubber, which is shaped like a belt (intermediate transfer belt), is used. In addition, as an embodiment of the intermediate transfer member 50, a drum-like member is used in addition to the belt-like member.

The image forming apparatus 100 may include, for example, an optical erasing device that performs optical erasing on the photoreceptor 7, in addition to the respective devices described above.

Figure 5:
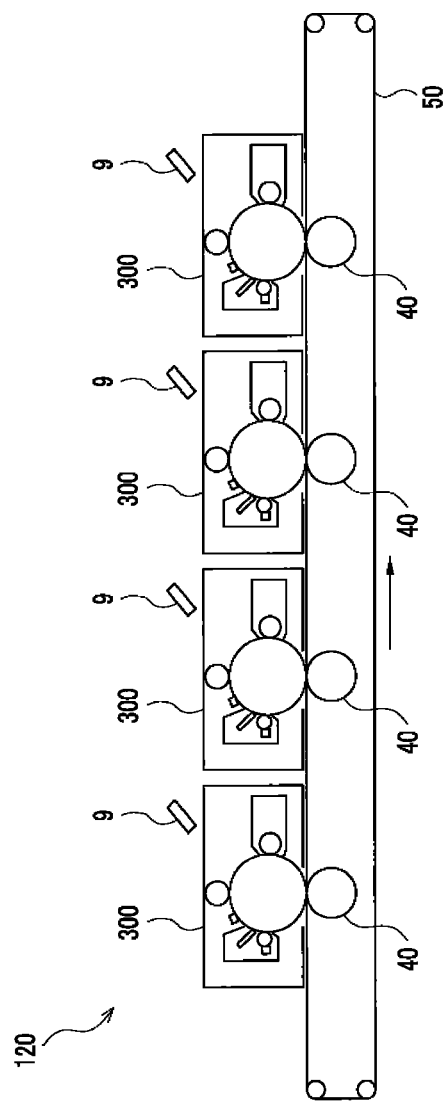
FIG. 5 is a schematic configuration view showing an image forming apparatus according to another exemplary embodiment.

FIG. 5 is a schematic cross-sectional view showing an image forming apparatus 120 according to another embodiment.

The image forming apparatus 120 shown in FIG. 5 is a tandem type color image forming apparatus on which four process cartridges 300 are mounted.

The image forming apparatus 120 has a configuration in which the four process cartridges 300 are arranged on the intermediate transfer member 50 in parallel, and one electrophotographic photoreceptor is used for a color. The image forming apparatus 120 has the same configuration as that of the image forming apparatus 100, except that the image forming apparatus 120 employs a tandem method.

The image forming apparatus according to the exemplary embodiment is not limited to the above-described configurations, and other image forming apparatuses that employ known methods may also be applied.

EXAMPLE

Hereinafter, the invention will be described in more detail based on examples, but the invention is not limited to the examples.

Synthesis Example 1

Synthesis of CTM-39

CTM-39 as an example compound is synthesized in the following scheme.

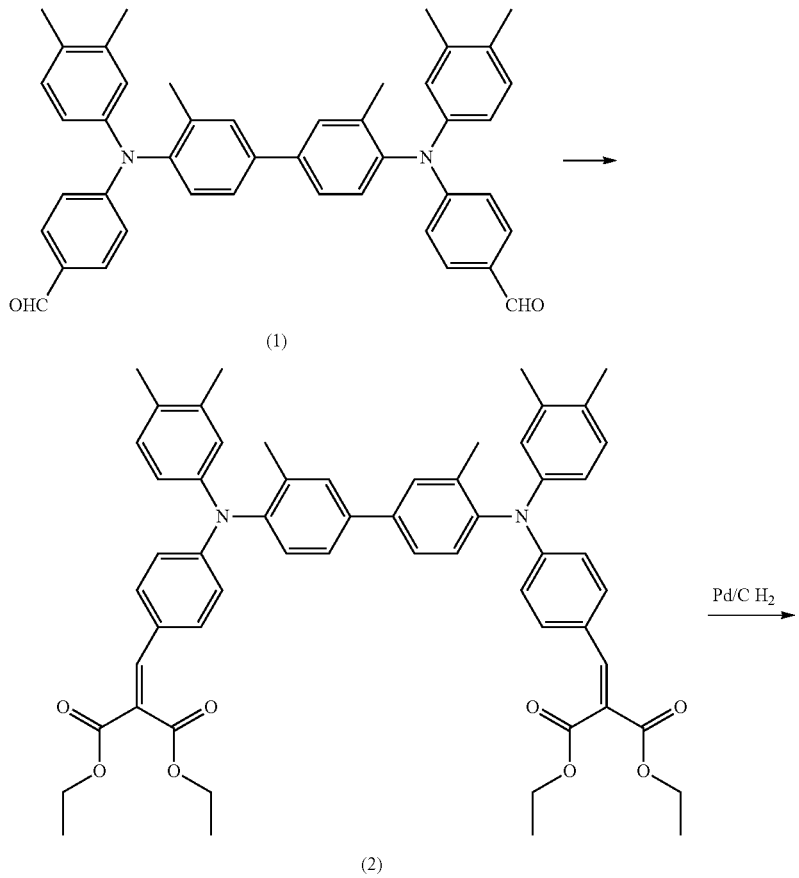

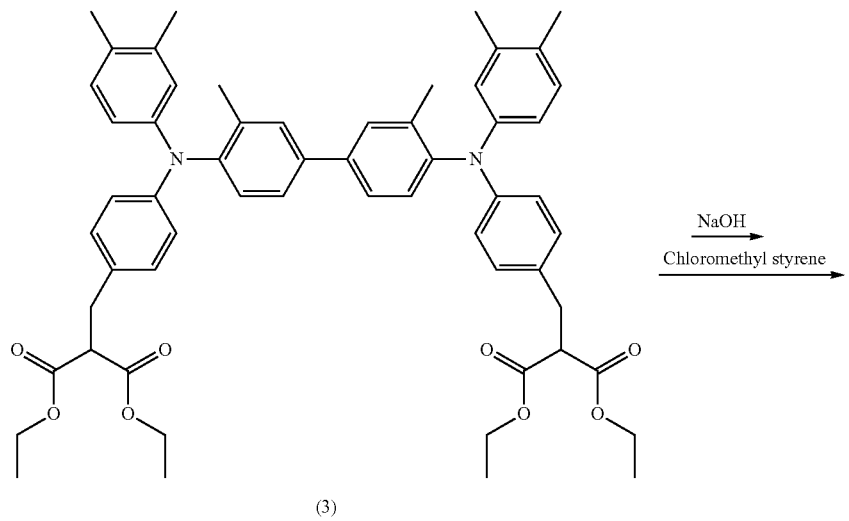

(3)

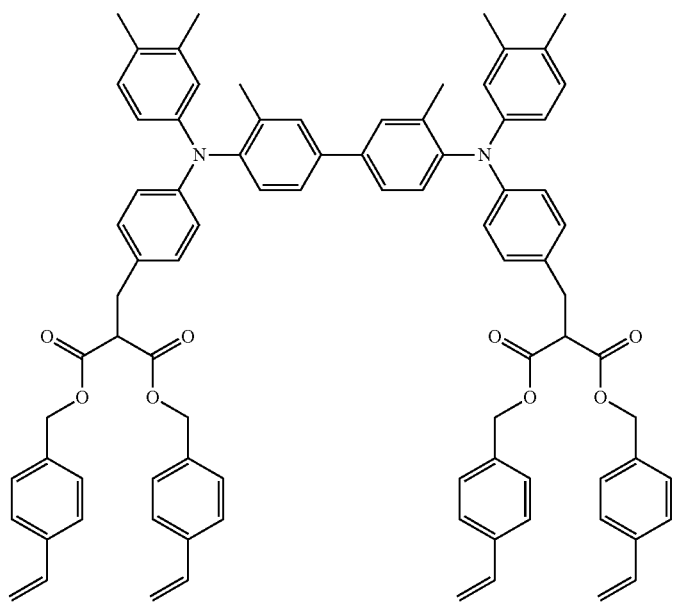

CTM-39

To a three-neck flask, 25 g of the compound (1), 250 ml of toluene, and 12.8 g of EthylMaronate are introduced and dissolved. Thereafter, 3.4 g of piperidine and 3.6 g of acetic acid are added thereto, followed by stirring at 130° C. for 2 hours. Then 0.68 g of piperidine and 0.72 g of acetic acid are further added thereto, followed by stirring at 130° C. for 1 hour. Subsequently, the temperature is cooled to room temperature, 250 ml of toluene is added thereto, and an organic layer is washed three times with 250 ml of distilled water. The resultant is dried with anhydrous sodium sulfate, and then the solvent is distilled away under reduced pressure. Thereafter, the resultant is purified by column chromatography (adsorbent: silica gel, solvent: toluene/ethyl acetate=10/1), thereby obtaining 33.3 of the oily compound (2).

Subsequently, to an eggplant-shaped flask, 33.3 g of the oily compound (2) is introduced and dissolved in 200 ml of tetrahydrofuran (hereinafter, written as "THF"), and 50 ml of ethanol and 2 g of 10% Pd/C are added thereto. The resultant is stirred for 24 hours while being connected to a source of hydrogen gas, and the solvent is distilled away under reduced pressure. Thereafter, the resultant is purified by column chromatography (adsorbent: silica gel, solvent: toluene/ethyl acetate=20/1), thereby obtaining 32.3 g of the oily compound (3).

Next, 25 g of the oily compound (3) is introduced to an eggplant-shaped flask and dissolved in 200 ml of THF and 50 ml of ethanol, and a solution obtained by dissolving 8.7 g of sodium hydroxide in 25 ml of distilled water is slowly added dropwise thereto at 0° C., followed by stirring for 2 hours at room temperature. The precipitated solid is washed two times with 100 ml of toluene, and then this solid is stirred at room temperature for 15 minutes and at 70° C. for 7 hours together with 200 ml of DMF and 40 g of chloromethyl styrene. Thereafter, the temperature is cooled to room temperature, and 500 ml of toluene is added thereto. An organic layer is then washed three times with 500 ml of distilled water and dried with anhydrous sodium sulfate, and then the solvent is distilled away under reduced pressure. Subsequently, the resultant is purified by column chromatography (adsorbent: silica gel, solvent: toluene/ethyl acetate=20/1), thereby obtaining 27.1 g of oily compound CTM-39.

The structure of the obtained CTM-39 is identified by an IR spectrum.

Figure 7:
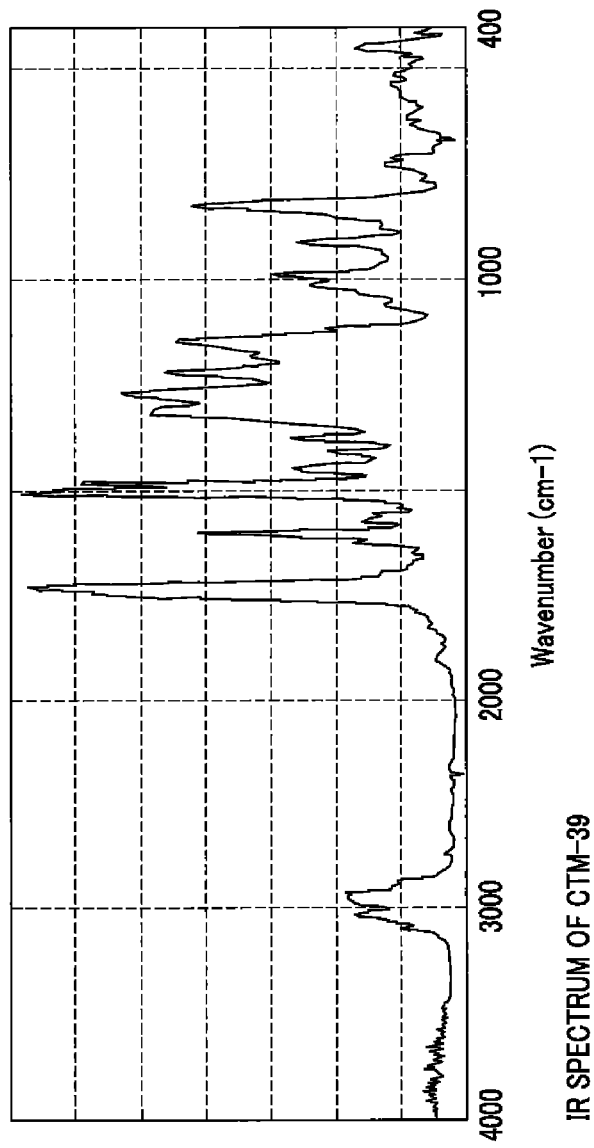
FIG. 7 is IR spectrum data of an example compound CTM-39.

The IR spectrum data of CTM-39 is shown in FIG. 7.

Synthesis Example 2

Synthesis of CTM-40

CTM-40 as an example compound is synthesized in the following scheme.

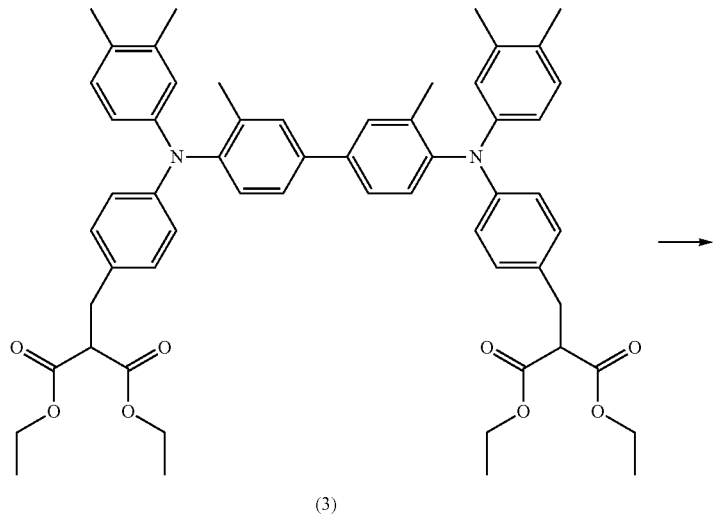

(3)

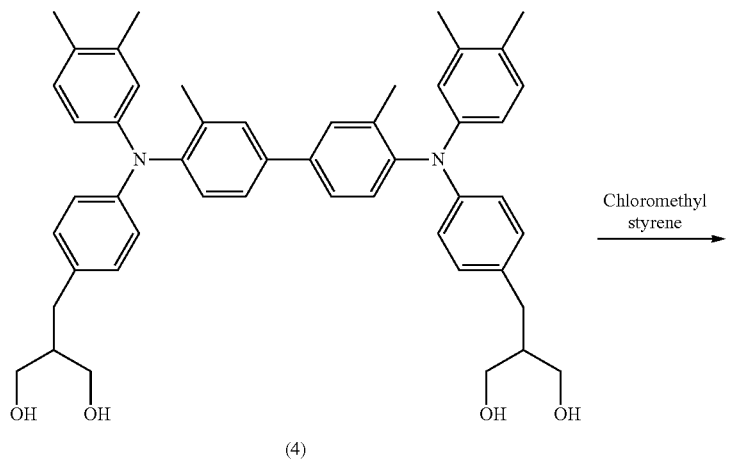

(4)

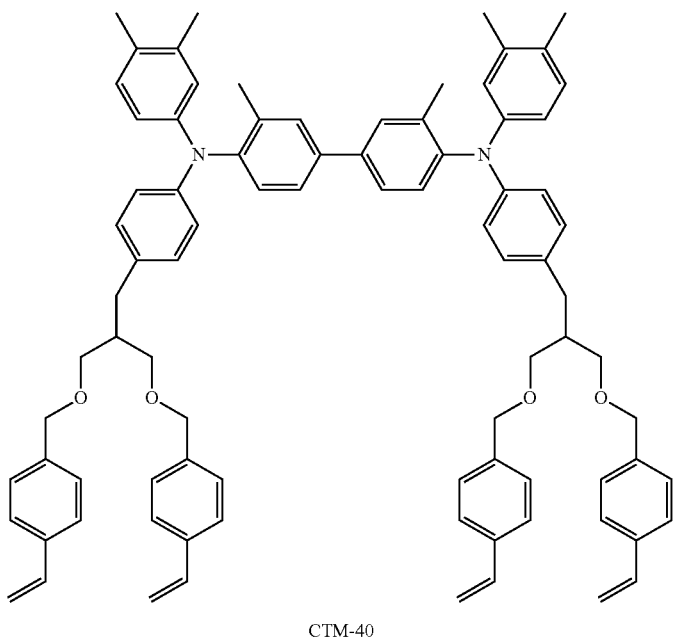 [SMILES: C=Cc1ccc(COC(=O)C(Cc2ccc(N(c3ccc(C)c(C)c3)c3ccc(-c4ccc(N(c5ccc(CC(C(=O)OCc6ccc(C=C)cc6)C(=O)OCc6ccc(C=C)cc6)cc5)c5ccc(C)c(C)c5)c(C)c4)cc3C)cc2)C(=O)OCc2ccc(C=C)cc2)cc1]

CTM-40

25 g of the compound (3) that is synthesized in the same manner as Synthesize Example 1 is dissolved in 250 ml of THF, and 8.9 g of lithium aluminum hydride is added thereto, followed by stirring at room temperature for 2 hours. Subsequently, 500 ml of water and 1 L of toluene are added thereto, and a solid content is filtered through filter paper lined with diatomite (celite, manufactured by Celite Corporation.). An organic layer is washed three times with 500 ml of distilled water and dried with anhydrous sodium sulfate, and then the solvent is distilled away under reduced pressure. Thereafter, the resultant is recrystallized from 20 ml of hexane and 30 ml of ethyl acetate, thereby obtaining 18.5 g of the solid-like compound (4) with a light peach color.

Subsequently, 16.5 g of the solid-like compound (4) is dissolved in 200 ml of THF, and 18 g of 4-chloromethyl styrene and 11.9 g of potassium tert-butoxide are slowly added thereto, followed by stirring at 70° C. for 16 hours. The temperature is then cooled to room temperature, and 250 ml of toluene is added thereto. An organic layer is washed three times with 250 ml of distilled water and dried with anhydrous sodium sulfate, and then the solvent is distilled away under reduced pressure. Thereafter, the resultant is purified by column chromatography (adsorbent: silica gel, solvent: toluene/ethyl acetate=20/1), thereby obtaining 20.3 g of oily CTM-40.

The structure of the obtained CTM-40 is identified by an IR spectrum.

Figure 8:
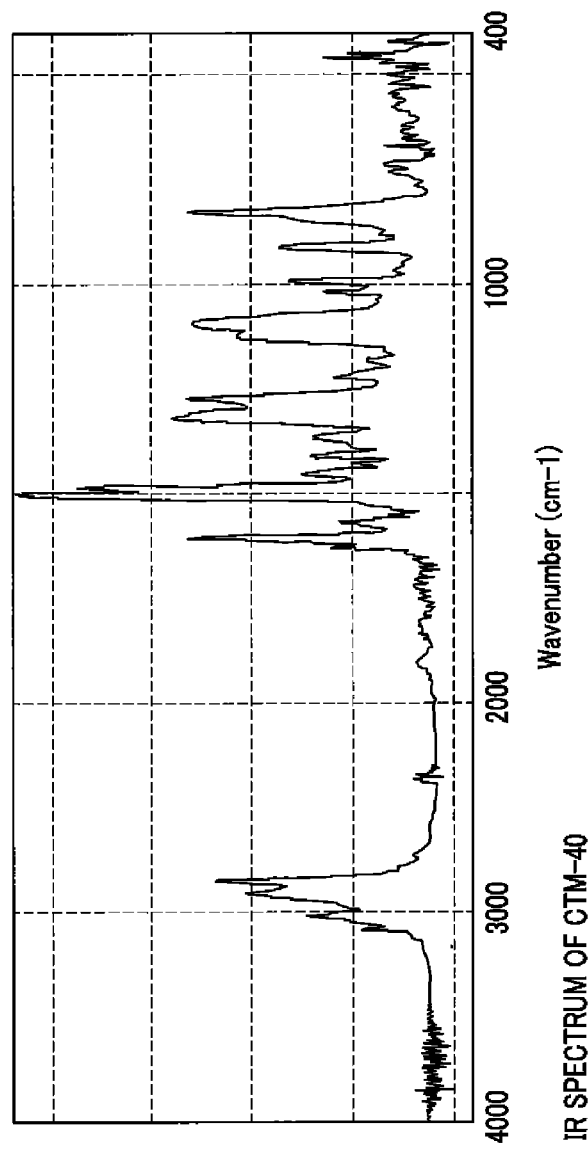
FIG. 8 is IR spectrum data of an example compound CTM-40.

The IR spectrum data of CTM-40 is shown in FIG. 8.

Synthesis Example 3

Synthesis of CTM-44

CTM-44 as an example compound is synthesized in the following scheme.

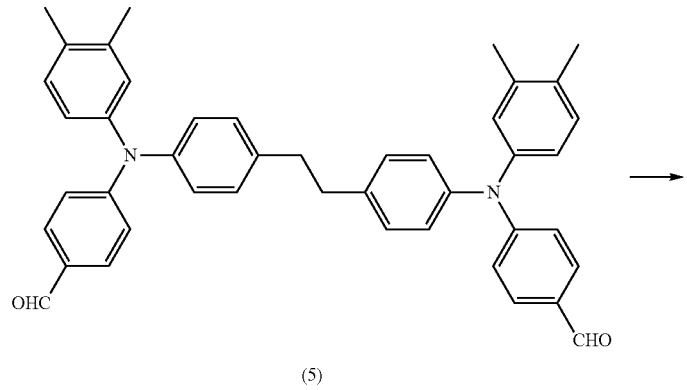

(5)

-continued
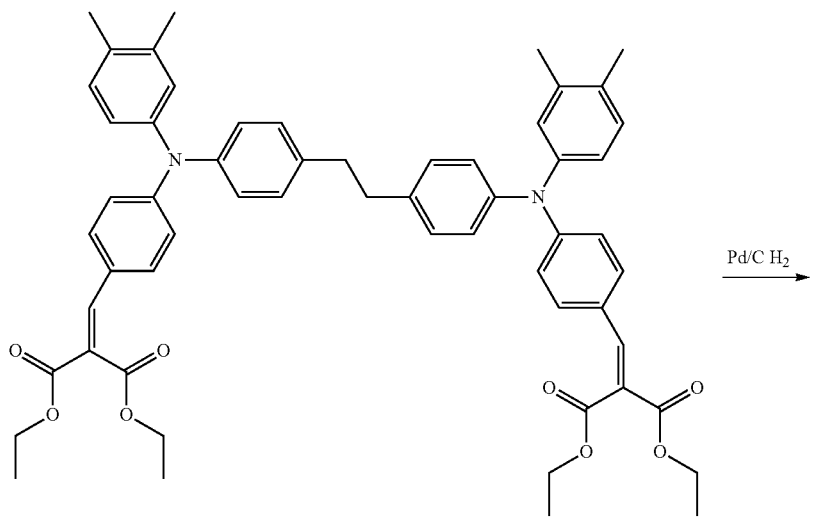
(6)
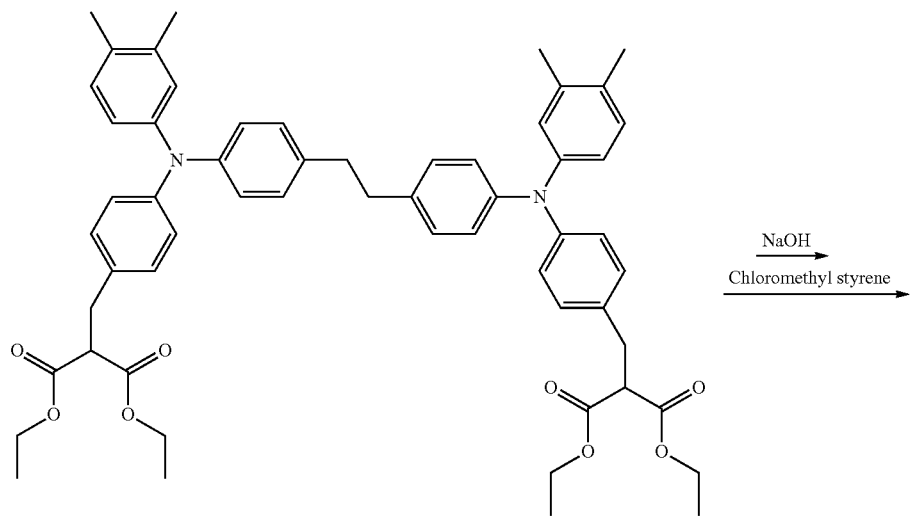
(7)

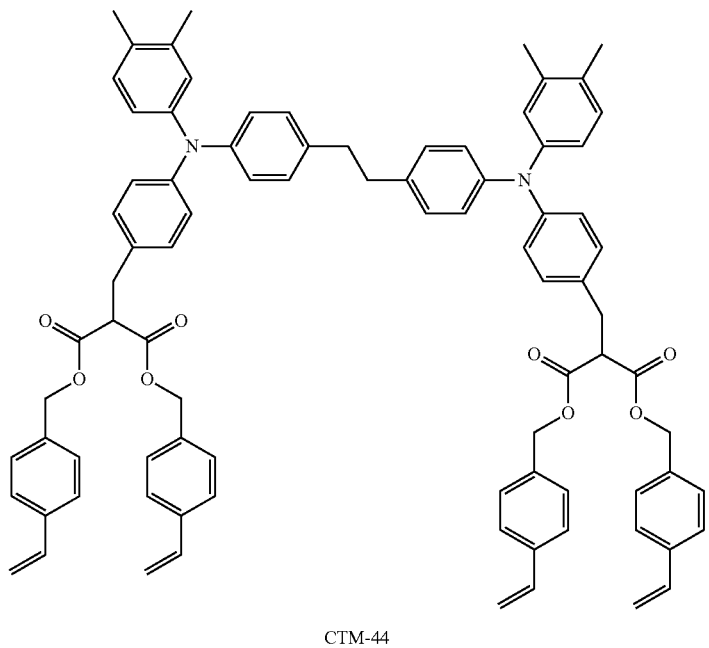 [SMILES: C=Cc1ccc(COC(=O)C(Cc2ccc(N(c3ccc(CCc4ccc(N(c5ccc(CC(C(=O)OCc6ccc(C=C)cc6)C(=O)OCc6ccc(C=C)cc6)cc5)c5ccc(C)c(C)c5)cc4)cc3)c3ccc(C)c(C)c3)cc2)C(=O)OCc2ccc(C=C)cc2)cc1]

CTM-44

To a three-neck flask, 25 g of the compound (5), 250 ml of toluene, and 12.8 g of EthylMaronate are introduced and dissolved. Thereafter, 3.4 g of piperidine and 3.6 g of acetic acid are added thereto, followed by stirring at 130° C. for 2 hours. Then 0.68 g of piperidine and 0.72 g of acetic acid are further added thereto, followed by stirring at 130° C. for 1 hour. Subsequently, the temperature is cooled to room temperature, 250 ml of toluene is added thereto, and an organic layer is washed three times with 250 ml of distilled water. The resultant is dried with anhydrous sodium sulfate, and then the solvent is distilled away under reduced pressure. Thereafter, the resultant is purified by column chromatography (adsorbent: silica gel, solvent: toluene/ethyl acetate=20/1), thereby obtaining 31.2 g of the oily compound (6).

Subsequently, to an eggplant-shaped flask, 31.2 g of the oily compound (6) is introduced and dissolved in 200 ml of THF, and 50 ml of ethanol and 2 g of 10% Pd/C are added thereto. The resultant is stirred for 24 hours while being connected to a source of hydrogen gas, and the solvent is distilled away under reduced pressure. Thereafter, the resultant is purified by column chromatography (adsorbent: silica gel, solvent: toluene/ethyl acetate-20/1), thereby obtaining 29.8 g of the oily compound (7).

Next, 25 g of the oily compound (7) is introduced to an eggplant-shaped flask and dissolved in 200 ml of THF and 50 ml of ethanol, and a solution obtained by dissolving 8.7 g of sodium hydroxide in 25 ml of distilled water is slowly added dropwise thereto at 0° C., followed by stirring for 2 hours at room temperature. The precipitated solid is washed two times with 100 ml of toluene, and then this solid is stirred at room temperature for 15 minutes and at 70° C. for 7 hours together with 200 ml of DMF and 40 g of chloromethyl styrene. Thereafter, the temperature is cooled to room temperature, and 500 ml of toluene is added thereto. An organic layer is then washed three times with 500 ml of distilled water and dried with anhydrous sodium sulfate, and then the solvent is distilled away under reduced pressure. Subsequently, the resultant is purified by column chromatography (adsorbent: silica gel, solvent: toluene/ethyl acetate-20/1), thereby obtaining 25.3 g of oily compound CTM-44.

The structure of the obtained CTM-44 is identified by an IR spectrum.

Figure 9:
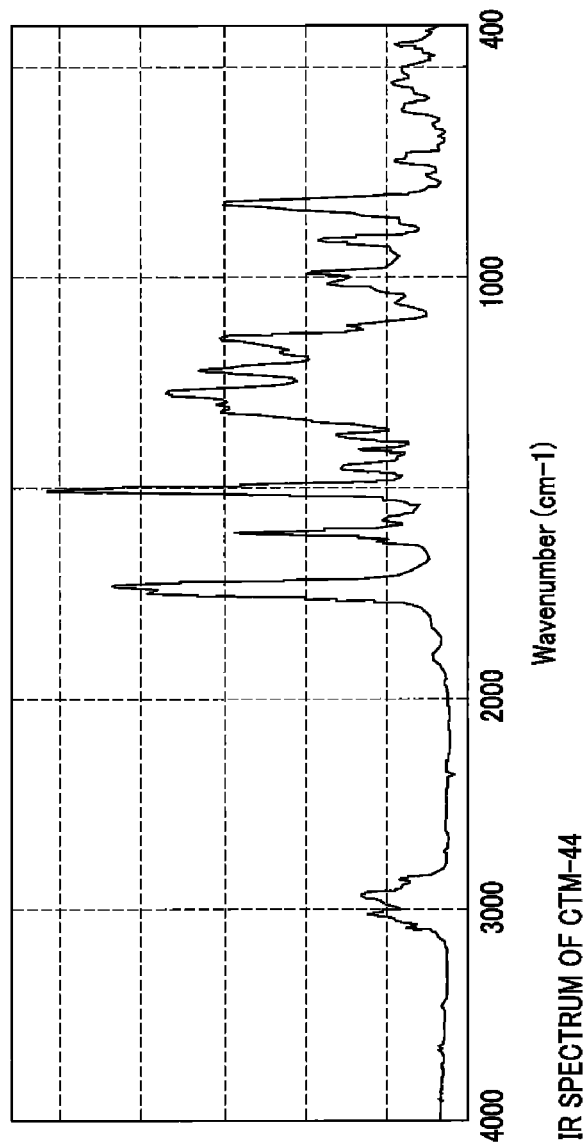
FIG. 9 is IR spectrum data of an example compound CTM-44.

The IR spectrum data of CTM-44 is shown in FIG. 9.

Synthesis Example 4

Synthesis of CTM-45

CTM-45 as an example compound is synthesized in the following scheme.

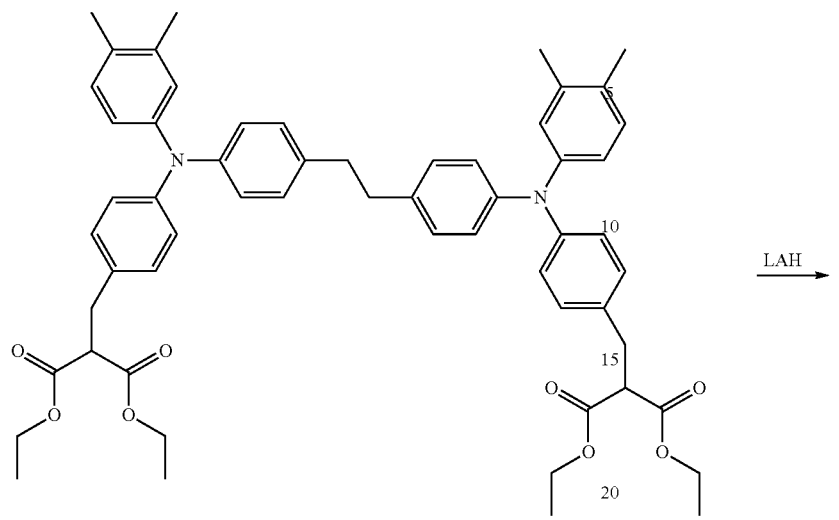
(7)
$\xrightarrow{\text{LAH}}$
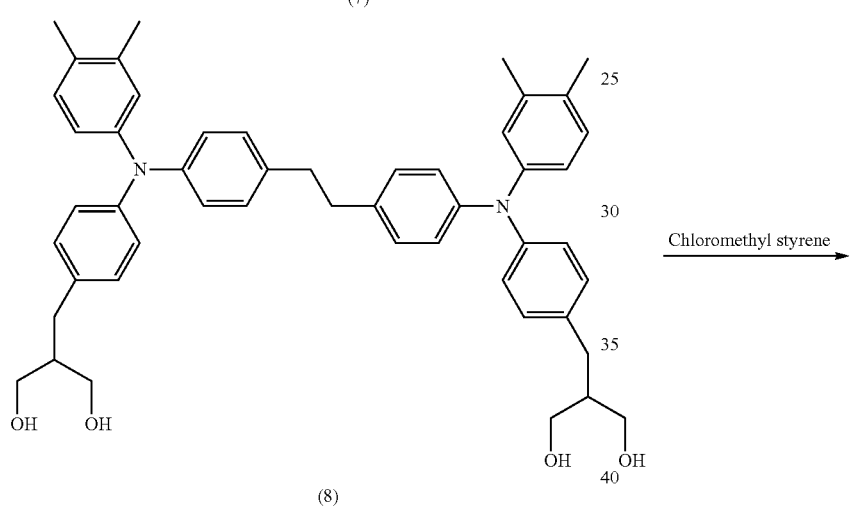
(8)
$\xrightarrow{\text{Chloromethyl styrene}}$
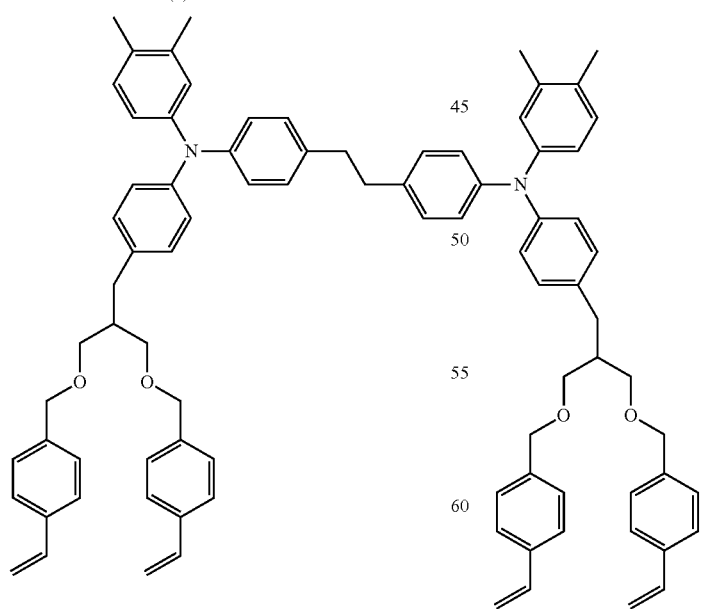
CTM-45

25 g of the compound (7) that is synthesized in the same manner as Synthesize Example 3 is dissolved in 250 ml of THF, and 9.2 g of lithium aluminum hydride is added thereto, followed by stirring at room temperature for 2 hours. Subsequently, 500 ml of water and 1 L of toluene are added thereto, and a solid content is filtered through filter paper lined with diatomite (celite, manufactured by Celite Corporation.). An organic layer is washed three times with 500 ml of distilled water and dried with anhydrous sodium sulfate, and then the solvent is distilled away under reduced pressure. Thereafter, the resultant is purified by column chromatography (adsorbent: silica gel, solvent: toluene/ethyl acetate=2/1), thereby obtaining 17.8 g of the oily compound (8).

Subsequently, 16.0 g of the oily compound (8) is dissolved in 200 ml of THF, and 17.5 g of 4-chloromethyl styrene and 11.2 g of potassium tert-butoxide are slowly added thereto, followed by stirring at 70° C. for 16 hours. The temperature is then cooled to room temperature, and 250 ml of toluene is added thereto. An organic layer is washed three times with 250 ml of distilled water and dried with anhydrous sodium sulfate, and then the solvent is distilled away under reduced pressure. Thereafter, the resultant is purified by column chromatography (adsorbent: silica gel, solvent: toluene/ethyl acetate=20/1), thereby obtaining 18.7 g of oily CTM-45.

The structure of the obtained CTM-45 is identified by an IR spectrum.

Figure 10:
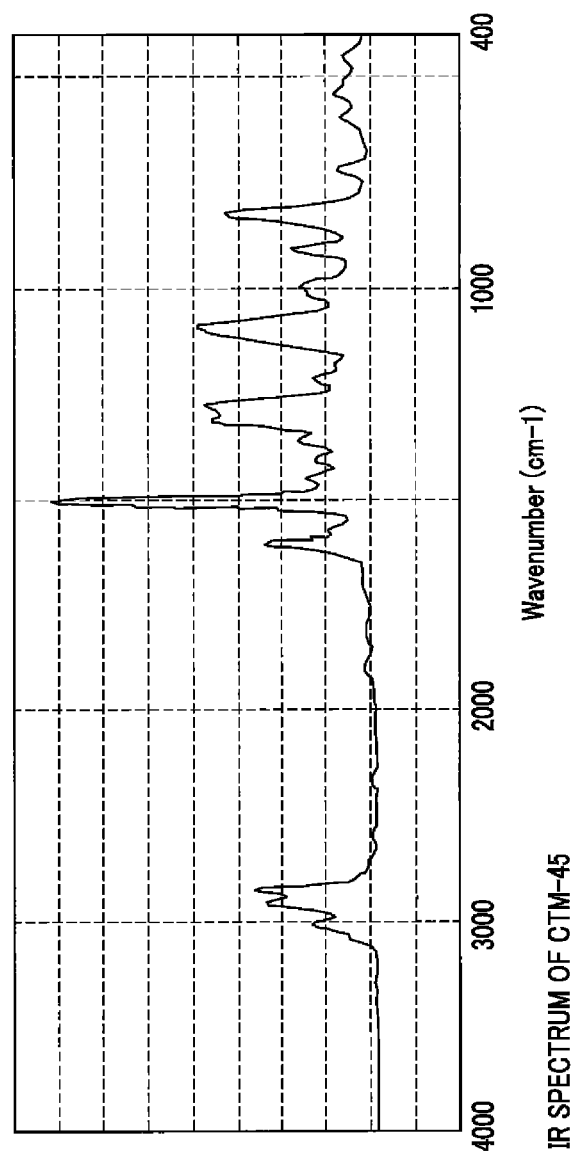
FIG. 10 is IR spectrum data of an example compound CTM-45.

The IR spectrum data of CTM-45 is shown in FIG. 10.

Synthesis Example 5

Synthesis of CTM-46

CTM-46 as an example compound is synthesized in the following scheme.

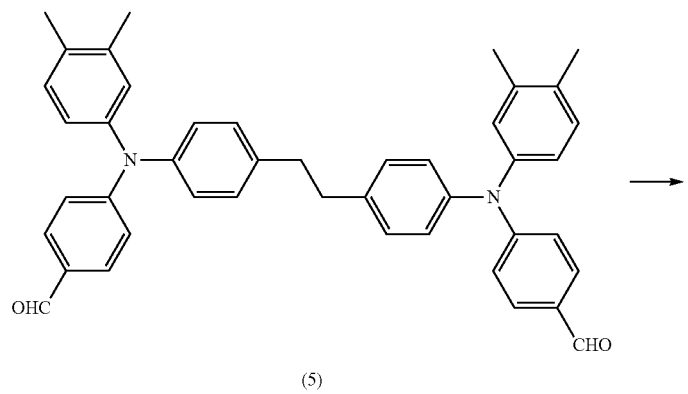

(5)

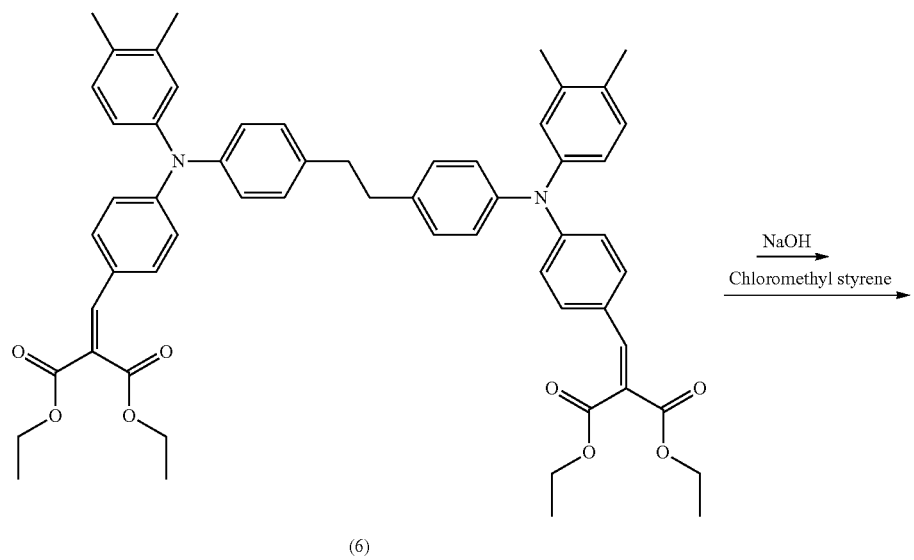

(6)

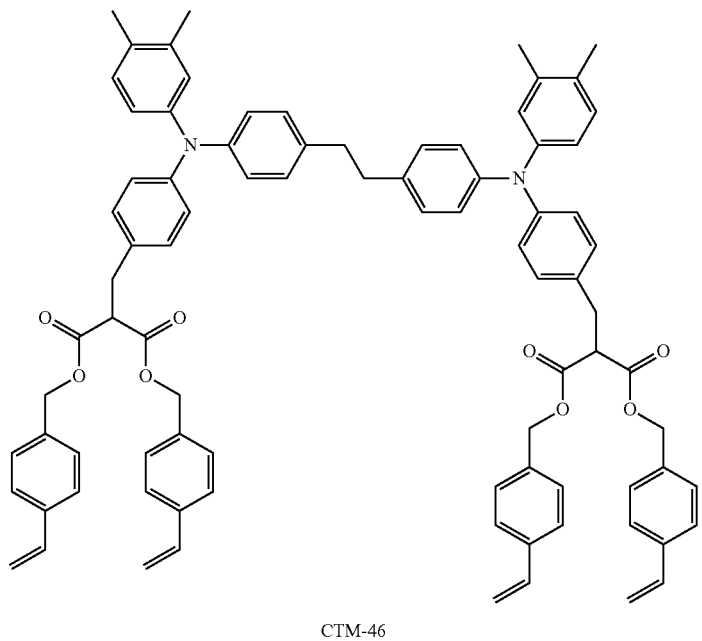

CTM-46

The compound (6) is synthesized from the compound (5) in the same manner as Synthesize Example 3.

27.5 g of the oily compound (6) is introduced to an eggplant-shaped flask and dissolved in 200 ml of THF and 50 ml of ethanol, and a solution obtained by dissolving 8.7 g of sodium hydroxide in 25 ml of distilled water is slowly added dropwise thereto at 0° C., followed by stirring for 2 hours at room temperature. A lower layer divided into two layers is washed two times with 100 ml of toluene, and then this lower layer is stirred at room temperature for 15 minutes and at 70° C. for 7 hours together with 200 ml of DMF and 40 g of chloromethyl styrene. Thereafter, the temperature is cooled to room temperature, and 500 ml of ethyl acetate is added thereto. An organic layer is then washed three times with 500 ml of distilled water and dried with anhydrous sodium sulfate, and then the solvent is distilled away under reduced pressure. Subsequently, the resultant is purified by column chromatography (adsorbent: silica gel, solvent: toluene/ethyl acetate=20/1), thereby obtaining 18.4 g of oily compound CTM-46.

The structure of the obtained CTM-46 is identified by an IR spectrum.

Figure 11:
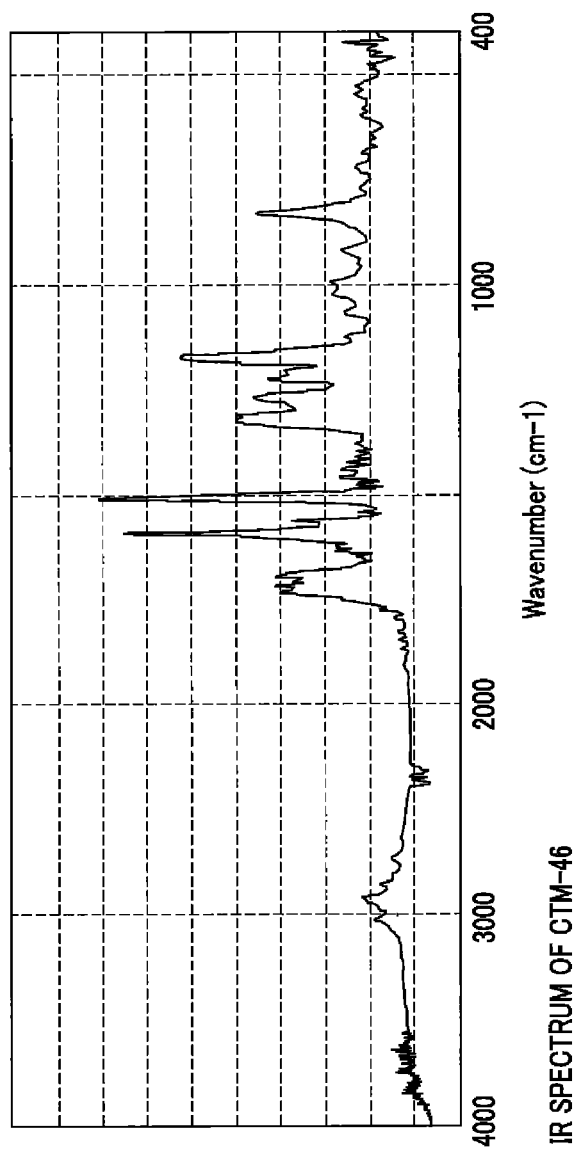
FIG. 11 is IR spectrum data of an example compound CTM-46.

The IR spectrum data of CTM-46 is shown in FIG. 11.

Example 1A (Preparation of Charge Transporting Film and Confirmation of Charge Transport Performance Thereof)
—Sample Preparation—

0.23 g of CTM-39 synthesized in the above-described manner is taken and dissolved in 0.77 g of THF that does not contain a stabilizer, and in this resultant, 0.005 g of a thermal radical generator V-601 is dissolved. The thus obtained solution is coated onto an ITO surface by a gap coater, and a film is formed at 145° C. for 35 minutes in a glove box with an oxygen concentration of 200 ppm or less, thereby obtaining a film having a thickness of about 7 μm.

Thereafter, a semitransparent gold electrode is prepared by sputtering, thereby preparing a CTL single layer sandwich type cell.

—Measurement of Charge Mobility—The charge mobility is measured by a Time of Flight (TOF) method. The charge mobility of CTM-11 in an electric field of 30 [V/μm] is $6.0 \times 10^{-6}$ [cm$^2$/Vs].

Examples 2A to 5A

For each of CTM-40, CTM-44, CTM-45, and CTM-46 synthesized in the above-described manner, samples are prepared in the same manner as Example 1A, and the charge mobility is measured in the same manner as Example 1A.

As a result, the charge mobility of the compounds in an electric field of 30 [V/μm] is CTM-40: $3.2 \times 10^{-5}$ [cm$^2$/Vs], CTM-44: $3.81 \times 10^{-6}$ [cm$^2$/Vs], CTM-45: $3.3 \times 10^{-5}$ [cm$^2$/Vs], and CTM-46: $4.0 \times 10^{-6}$ [cm$^2$/Vs], respectively.

Comparative Examples 1A and 2A

For CTM-ref1 and CTM-ref2 shown below, samples are prepared in the same manner as Example 1A, and the charge mobility is measured in the same manner as Example 1A.

As a result, the charge mobility of the compounds in an electric field of 30 [V/μm] is CTM-ref1: $8.4 \times 10^{-7}$ [cm$^2$/Vs] and CTM-ref2: $7.1 \times 10^{-7}$ [cm$^2$/Vs], respectively.

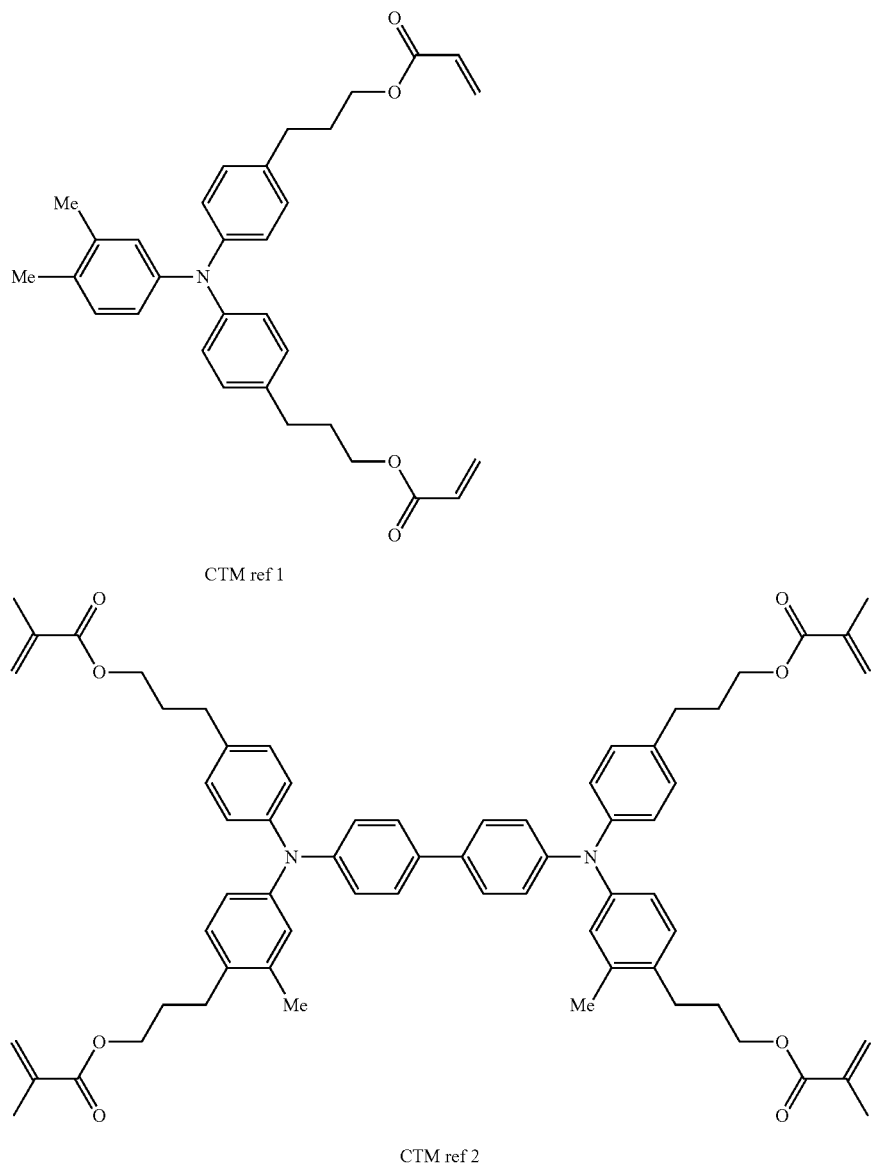

CTM ref 1

CTM ref 2

From Examples 1A to 4A and Comparative Examples 1A and 2A, it is understood that the cured film (charge transporting film) using the novel compound according to the exemplary embodiment has a very excellent charge transport function, compared to the cured film (charge transporting film) using CTM-ref1 or CTM-ref2 that has been known in the related art.

The charge transporting film containing the polymer of the novel compound according to the exemplary embodiment may be used for various photoelectric conversion devices.

Examples of the photoelectric conversion device include an electrophotographic photoreceptor, an organic EL device, an organic transistor, an organic solar cell, and the like. Hereinafter, an organic EL device will be shown as an example of the exemplary embodiment, but the invention is not limited to this example.

Example B1

An ITO glass substrate that includes an ITO film on a glass substrate is prepared, and the ITO film is etched into an approximately strip shape having a width of 2 mm, thereby forming an ITO electrode (anode). This ITO glass substrate is subjected to ultrasonic cleaning by using isopropanol (used in the field of electronic industry, manufactured by KANTO KAGAKU) and then dried using a spin coater.

Thereafter, in the ITO glass substrate, copper phthalocyanine prepared by sublimation is vacuum-deposited onto the surface where the ITO electrode has been formed, thereby forming a thin film having a thickness of 0.015 μm.

Subsequently, 2 parts by weight of CTM-15 synthesized in the above-described manner is dissolved in 100 parts by weight of THF that does not contain a stabilizer, and in this resultant, 0.3 parts by weight of an initiator V-601 (manufactured by Wako Pure Chemical Industries, Ltd.) is dissolved, thereby obtaining a coating liquid for forming a thin film. This coating liquid is coated onto the copper phthalocyanine film, followed by heating at 150° C. for 40 minutes in an atmosphere in which an oxygen concentration of about 80 ppm, thereby forming a thin film having a thickness of 0.050 μm.

Thereafter, as a luminous material, a compound (Alq₃) represented by the following formula is vapor-deposited onto the above thin film, thereby forming a luminous layer having a thickness of 0.060 μm.

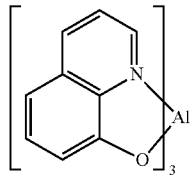

In addition, on the luminous layer, an Mg—Ag alloy is vapor-deposited by codeposition, thereby forming an Mg—Ag electrode (cathode) with an approximately strip shape having a width of 2 mm and a thickness of 0.13 μm. In this manner, an organic electroluminescence element is obtained. The ITO electrode and Mg—Ag electrode are formed such that these electrodes extend at right angles to each other. An effective area of the obtained organic electroluminescence element is 0.04 cm².

In vacuum (0.133 Pa), the ITO electrode is used as a positive electrode (anode), and the Mg—Ag electrode is used as a negative electrode (cathode). DC voltage is applied to these electrodes so as to cause the electrodes to emit light. At this time, maximum luminance is 850 cd/m², driving voltage is 8.4 mA/cm², and element lifetime is 45 hours.

As described so far, it is confirmed that the organic electroluminescence element using the charge transporting film containing the polymer of the novel compound according to the exemplary embodiment may obtain excellent electrical characteristics and may form elements having a long lifetime without morphological change.

Example 1

(Preparation of Electrophotographic Photoreceptor)
—Preparation of Undercoat Layer—
100 parts by weight of zinc oxide (average particle size of 70 nm: manufactured by TAYCA: specific surface area of 15 m²/g) is mixed with 500 parts by weight of toluene under stirring, and 1.3 part by weight of a silane coupling agent (KBM503: manufactured by Shin-Etsu Chemical Co., Ltd.) is added thereto, followed by stirring for 2 hours. Thereafter, toluene is distilled away through distillation under reduced pressure, and the resultant is baked at 120° C. for 3 hours, thereby obtaining zinc oxide that has been surface-treated with the silane coupling agent.

110 parts by weight of the surface-treated zinc oxide is mixed with 500 parts by weight of tetrahydrofuran under stirring, and a solution obtained by dissolving 0.6 parts by weight of alizarin in 50 parts by weight of tetrahydrofuran is added thereto, followed by stirring at 50° C. for 5 hours. Thereafter, the alizarin-imparted zinc oxide is filtered by filtration under reduced pressure, followed by drying at 60° C. under reduced pressure, thereby obtaining alizarin-imparted zinc oxide.

38 parts by weight of a solution obtained by mixing 60 parts by weight of the alizarin-imparted zinc oxide, 13.5 parts by weight of a curing agent (blocked isocyanate Sumidur 3175, manufactured by Sumitomo Bayer Urethane Co., Ltd.), and 15 parts by weight of a butyral resin (S-LEC BM-1, manufactured by SEKISUI CHEMICAL CO., LTD.) with 85 parts by weight of methyl ethyl ketone are mixed with 25 parts by weight of methyl ethyl ketone, and the resultant is dispersed with a sand mill for 2 hours by using glass beads having a diameter of 1 mmφ, thereby obtaining a dispersion.

To the obtained dispersion, 0.005 parts by weight of dioctyltin dilaurate and 40 parts by weight of silicone resin particles (Tospearl 145, manufactured by GE Toshiba Silicones, Co., Ltd.) are added as a catalyst, thereby obtaining a coating liquid for forming an undercoat layer. This coating liquid is coated onto an aluminum substrate by dip coating, followed by drying and curing at 175° C. for 40 minutes, thereby obtaining an undercoat layer having a thickness of 22 μm.

—Preparation of Charge Generating Layer—
A mixture including 15 parts by weight of hydroxy gallium phthalocyanine as a charge generating material in which the Bragg angle)(2θ±0.2°) of an X-ray diffraction spectrum using X-rays having Cukα characteristics has diffraction peaks at positions of at least 7.3°, 16.0°, 24.9°, and 28.0°, 10 parts by weight of a vinyl chloride-vinyl acetate copolymer resin (VMCH, manufactured by Nippon Unicar Co., Ltd.) as a binder resin, and 200 parts by weight of n-butyl acetate is dispersed with a sand mill for 4 hours by using glass beads having a diameter of 1 mmφ. To the obtained dispersion, 175 parts by weight of n-butyl acetate and 180 parts by weight of methyl ethyl ketone are added, followed by stirring, thereby obtaining a coating liquid for forming a charge generating layer. This coating liquid for forming a charge generating layer is coated onto the undercoat layer by dip-coating, followed by drying at room temperature (25° C.), thereby forming a charge generating layer having a film thickness of 0.15 μm.

—Preparation of Charge Transporting Layer—
48 parts by weight of N,N'-diphenyl-N,N'-bis(3-methylphenyl)-[1,1']biphenyl-4,4'-diamine (hereinafter, written as "TPD") and 52 parts by weight of Bisphenol Z polycarbonate resin (hereinafter, written as "PCZ 500", viscosity average molecular weight: 50000) are added to 800 parts by weight of chlorobenzene, followed by dissolving, thereby obtaining a coating liquid for forming a charge transporting layer. This coating liquid is coated onto the charge generating layer, followed by drying at 130° C. for 45 minutes, thereby obtaining a charge transporting layer having a film thickness of 22 μm.

—Preparation of Protective Layer—
20 parts by weight of the compound (the example compound CTM-9) represented by General Formula (I) is dissolved in 15 parts by weight of THF that does not contain a stabilizer and 15 parts by weight of cyclopentyl methyl ether, and in this resultant, 3.8 parts by weight of an initiator V-601 (manufactured by Wako Pure Chemical Industries, Ltd.) is dissolved, thereby obtaining a coating liquid for forming a protective layer. This coating liquid is coated onto the charge transporting layer, followed by heating at 155° C. for 40 minutes in an atmosphere in which an oxygen concentration of about 80 ppm, thereby forming a protective layer having a thickness of 7 μm.

In this manner, an electrophotographic photoreceptor is obtained. This photoreceptor is taken as a photoreceptor 1.

(Evaluation)
(1) Measurement of Charged Potential (Surface Potential) and Residual Potential
The obtained electrophotographic photoreceptor is subjected to the following steps (A) to (C) at a high temperature and high humidity (28° C., 67% RH).
(A) Charging the electrophotographic photoreceptor with a scorotron charging device of grid applied voltage of −700 V (B) Exposing in which light of 10.0 erg/cm² is emitted after 1 second of the step (A) by using a semiconductor laser having a wavelength of 780 nm (C) Erasing in which red LED light of 50.0 erg/cm² is emitted after 3 seconds of the step (A)

At this time, the above steps are repeated 100K cycles by using a laser printer-modified scanner.

VH (surface potential that the photoreceptor has after being charged in step (A)), VL (surface potential that the photoreceptor has after being exposed in step (B)), and VRP (surface potential (residual potential) that the photoreceptor has after being erased in step (C)) are measured initially and after 100K cycles, and the initial VH, VL, and VRP and variances ΔVH, ΔVL, and ΔVRP from the initial value are calculated.

For the surface potential (residual potential) measurement, a surface electrometer MODEL 344 (manufactured by TREK JAPAN) is used.

Evaluation indices are as follows.
(Evaluation Indices for VL)
A: −240 V or more
B: −280 V or more and less than −240 V
C: −300 V or more and less than −280 V
D: less than −300 V
(Evaluation Indices for VRP)
A: −130 V or more
B: −150 V or more and less than −130 V
C: −170 V or more and less than −150 V
D: less than −170 V
(Evaluation Indices for ΔVH, ΔVL, and ΔVRP)
A: 10 V or less
B: more than 10 V and 20 V or less
C: more than 20 V and 30 V or less
D: more than 30 V The results of these evaluations are shown in Table 2. P (2) Initial Image Quality Evaluation: Ghost Evaluation The prepared electrophotographic photoreceptor is mounted on "DocuCentre-III C7600 (Black color)" manufactured by Fuji Xerox Co., Ltd., and the ghost evaluation (test 1) is conducted in the following manner in an environment of 28° C. and 67% RH.

For this evaluation, P paper (A4 size, fed in the transverse direction) manufactured by Fuji Xerox Co., Ltd. is used.

—Ghost Evaluation—

Figure 6:
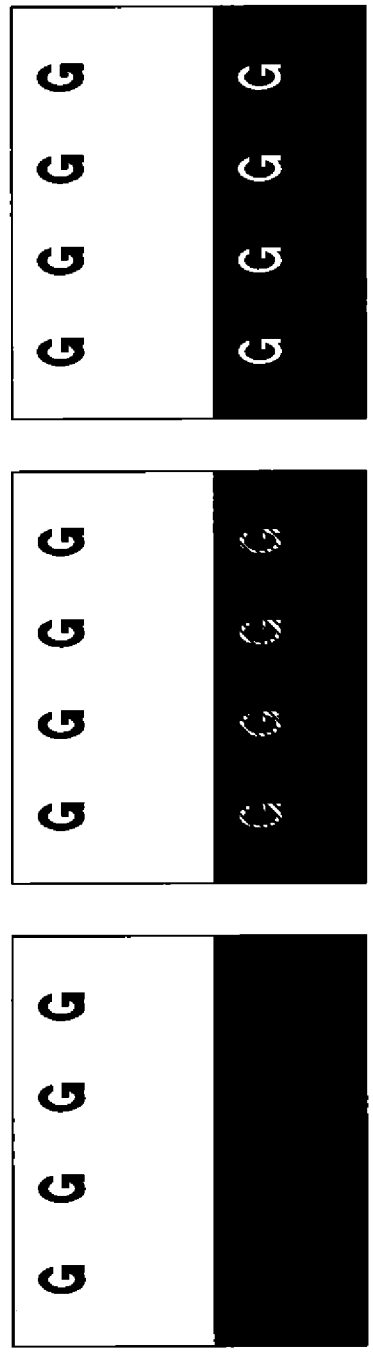
FIGS. 6A to 6C are views for illustrating ghost evaluation criteria respectively.

Ghost is evaluated by printing charts of a pattern having G and a black area, which is shown in FIG. 6A, and visually observing how the letter G appears in the black area.

A: ghost is excellent or slightly shown as in FIG. 6A.
B: ghost is slightly noticeable as shown in FIG. 6B.
C: ghost is obviously noticeable as shown in FIG. 6C.

(3) Image Quality Evaluation after Printing Test: Ghost Evaluation

The prepared electrophotographic photoreceptor is mounted on "DocuCentre-III C7600 (Black color)" manufactured by Fuji Xerox Co., Ltd., and 10000 sheets with 15% half tone are printed for a test in an environment of 28° C. and 67% RH. For this evaluation, P paper (A4 size, fed in the transverse direction) manufactured by Fuji Xerox Co., Ltd. is used.

Thereafter, ghost evaluation (test 2) is conducted in the same manner as described above in an environment of 28° C. and 67% RH.

(4) Initial Surface Observation

The surface of the electrophotographic photoreceptor at the time of the "(2) Initial image quality evaluation: ghost evaluation" is observed, and surface observation (test 1) is conducted in the following manner.

—Surface Observation—

The surface of the electrophotographic photoreceptor is observed and evaluated in the following manner.

A: excellent. Scratches or extraneous matter are not found even if the image is magnified 20×.

B: extraneous matter is found when the image is magnified 20×.

C: slight scratches are found when the image is magnified 20×.

D: slight scratches or extraneous matter are found by the naked eye.

E: scratches or extraneous matter are obviously found by the naked eye.

(5) Surface Observation after Printing Test

The surface of the electrophotographic photoreceptor at the time of "(3) Image quality evaluation after printing test: ghost evaluation" is observed, and surface observation (test 2) is conducted in the same manner as described above.

Examples 2 to 14 and Comparative Example 1

(Preparation of Electrophotographic Photoreceptor)

The same manner as Example 1 is applied until the charge transporting layer is prepared, and the composition of materials used for forming the protective layer is changed as shown in Table 2, thereby obtaining coating liquids for forming a protective layer. The respective coating liquids are coated onto the charge transporting layer, followed by heating at 155° C. for 40 minutes in an atmosphere in which an oxygen concentration of about 80 ppm, thereby forming a protective layer having a thickness of 7 μm.

In this manner, electrophotographic photoreceptors are obtained. These electrophotographic photoreceptors are taken as photoreceptors 2 to 14 and a comparative photoreceptor 1.

Herein, Ref CT-1 which is used as the compound having a charge transport performance in Comparative Example 1 is shown below.

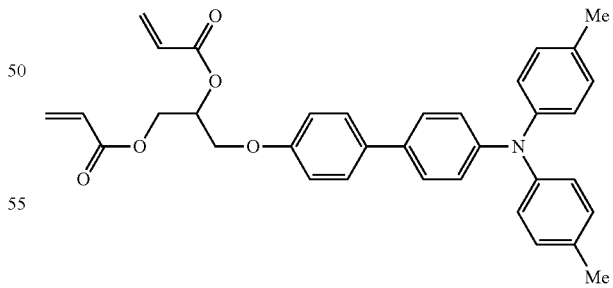

Ref CT-1

(Evaluation)

The obtained photoreceptors are evaluated in the same manner as Example 1, and the results are shown in Table 3.

TABLE 2

|  | Example | | | | |
|---|---|---|---|---|---|
|  | Example 1 | Example 2 | Example 3 | Example 4 | Example 5 |
| (1) | CTM-9 | CTM-39 | CTM-40 | CTM-41 | CTM-42 |
| Amount (part by weight) | 20 | 20 | 20 | 20 | 20 |
| Initiator | V-601 | V-601 | V-601 | V-601 | V-601 |
| Amount (part by weight) | 3.8 | 3.8 | 3.8 | 3.8 | 3.8 |
| Photoreceptor name | Photoreceptor 1 | Photoreceptor 2 | Photoreceptor 3 | Photoreceptor 4 | Photoreceptor 5 |

|  | Example | | | | |
|---|---|---|---|---|---|
|  | Example 6 | Example 7 | Example 8 | Example 9 | Example 10 |
| (1) | CTM-44 | CTM-45 | CTM-46 | CTM-47 | CTM-48 |
| Amount (part by weight) | 20 | 20 | 20 | 20 | 20 |
| Initiator | V-601 | V-601 | V-601 | V-601 | V-601 |
| Amount (part by weight) | 3.8 | 3.8 | 3.8 | 3.8 | 3.8 |
| Photoreceptor name | Photoreceptor 6 | Photoreceptor 7 | Photoreceptor 8 | Photoreceptor 9 | Photoreceptor 10 |

|  | Example | | | | Comparative Example 1 |
|---|---|---|---|---|---|
|  | Example 11 | Example 12 | Example 13 | Example 14 |  |
| (1) | CTM-49 | CTM-50 | CTM-51 | CTM-62 | Ref CTM-1 |
| Amount (part by weight) | 20 | 20 | 20 | 20 | 20 |
| Initiator | V-601 | V-601 | V-601 | V-601 | V-601 |
| Amount (part by weight) | 3.8 | 3.8 | 3.8 | 3.8 | 3.8 |
| Photoreceptor name | Photoreceptor 11 | Photoreceptor 12 | Photoreceptor 13 | Photoreceptor 14 | Photoreceptor R1 |

TABLE 3

|  |  | Example 1 | Example 2 | Example 3 | Example 4 | Example 5 |
|---|---|---|---|---|---|---|
| Test (1) | VL | A | A | A | A | A |
|  | VRP | A | A | A | A | A |
|  | Ghost | A | A | A | A | A |
|  | Surface observation | A | A | A | A | A |
| Test (2) | ΔVH | A | A | A | A | A |
|  | ΔVL | B | B | A | B | A |
|  | ΔVRP | A | A | A | A | B |
|  | Ghost | B | A | A | B | A |
|  | Surface observation | C | A | A | A | A |

|  |  | Example 6 | Example 7 | Example 8 | Example 9 | Example 10 |
|---|---|---|---|---|---|---|
| Test (1) | VL | A | A | A | A | A |
|  | VRP | A | A | A | A | A |
|  | Ghost | A | A | A | A | B |
|  | Surface observation | A | A | A | A | A |
| Test (2) | ΔVH | A | A | A | A | A |
|  | ΔVL | B | A | B | A | B |
|  | ΔVRP | A | A | B | B | B |
|  | Ghost | A | A | A | A | B |
|  | Surface observation | A | A | A | A | A |

|  |  | Example 11 | Example 12 | Example 13 | Example 14 | Comparative Example 1 |
|---|---|---|---|---|---|---|
| Test (1) | VL | A | A | A | A | B |
|  | VRP | A | A | A | A | B |
|  | Ghost | A | A | A | A | C |
|  | Surface observation | A | A | A | A | A |
| Test (2) | ΔVH | A | A | A | A | B |
|  | ΔVL | B | B | B | B | C |
|  | ΔVRP | B | B | B | A | D |
|  | Ghost | B | A | A | A | D |
|  | Surface observation | A | A | A | A | D |

From the above results, it is understood that the examples are excellent in VL and VRP and in variances ΔVH, ΔVL, and ΔVRP from the initial value, compared to the comparative example.

Moreover, in the examples, ghost is excellent in both the initial stage and after the printing test, and the surface observation after the printing test also obtains excellent results, compared to the comparative example.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A compound represented by the following General Formula (I):

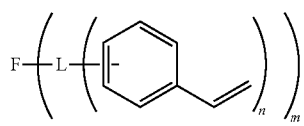

(I)

wherein in General Formula (I), F represents a charge transporting subunit, L represents a linking group having a valency of (n+1) that is formed by combining two or more kinds selected from the group consisting of an alkylene group, —C═C— (an alkenylene group), —C(═O)—, —N(R)—, —O—, and —S—, and R represents a hydrogen atom, an alkyl group, an aryl group, or an aralkyl group, m represents an integer of from 1 to 6, and n represents an integer of from 2 to 3.

2. The compound according to claim 1, which is represented by the following General Formula (II):

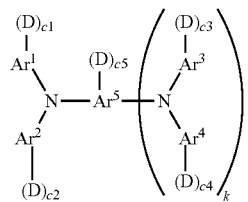

(II)

wherein in General Formula (II), each of $Ar^1$ to $Ar^4$ independently represents a substituted or unsubstituted aryl group, $Ar^5$ represents a substituted or unsubstituted aryl group or a substituted or unsubstituted arylene group, D represents a group represented by General Formula (III), k represents 0 or 1, each of c1 to c5 represents an integer of from 0 to 2, and at least one of c1 to c5 is not 0:

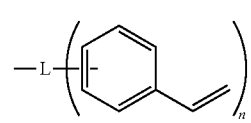

(III)

wherein in General Formula (III), L represents a linking group having a valency of (n+1) that is formed by combining two or more kinds selected from the group consisting of an alkylene group, —C═C— (an alkenylene group), —C(═O)—, N(R)—, —O—, and —S—, R represents a hydrogen atom, an alkyl group, an aryl group, or an aralkyl group, and n represents an integer of from 2 to 3.

3. The compound according to claim 1,
wherein the following partial structure in the compound represented by General Formula (I) is a group represented by the following General Formula (IV-1) or a group represented by the following General Formula (IV-2):

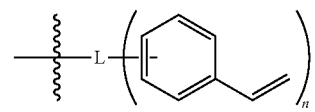

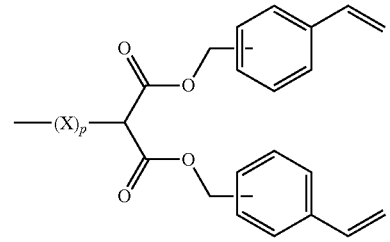

(IV-1)

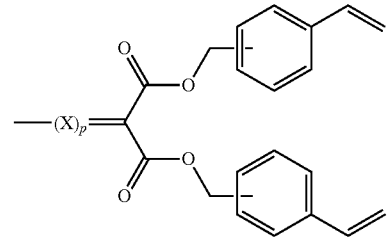

(IV-2)

wherein in General Formulae (IV-1) and (IV-2), X represents a divalent group, and p represents 0 or 1, and the wavy line in the above partial structure represents a site binding to the charge transporting subunit represented by F.

4. The compound according to claim 1,
wherein the following partial structure in the compound represented by General Formula (I) is a group represented by the following General Formula (V-1) or a group represented by the following General Formula (V-2):

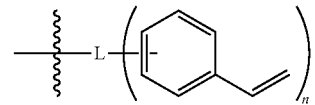

-continued

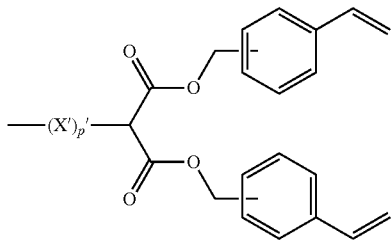
(V-1)

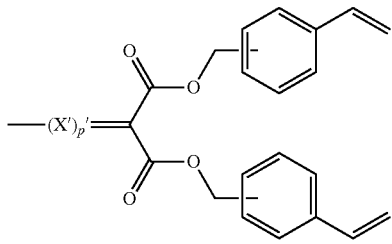
(V-2)

wherein in General Formulae (V-1) and (V-2), X' represents a divalent group, and p' represents 0 or 1, and the wavy line in the above partial structure represents a site binding to the charge transporting subunit represented by F.

5. A charge transporting film comprising a polymer of the compound according to claim 1.

6. The charge transporting film according to claim 5, further comprising a thermal radical generator or a derivative thereof.

7. A photoelectric conversion device comprising the charge transporting film according to claim 5.

8. An electrophotographic photoreceptor comprising a charge transporting layer that contains a polymer of a compound represented by the following General Formula (I):

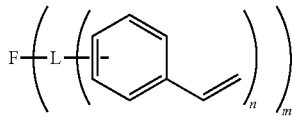
(I)

wherein in General Formula (I), F represents a charge transporting subunit, L represents a linking group having a valency of (n+1) that is formed by combining two or more kinds selected from the group consisting of an alkylene group, —C═C— (an alkenylene group), —C(═O)—, —N(R)—, —O—, and —S—, and R represents a hydrogen atom, an alkyl group, an aryl group, or an aralkyl group, m represents an integer of from 1 to 6, and n represents an integer of from 2 to 3.

9. The electrophotographic photoreceptor according to claim 8,
wherein the compound represented by General Formula (I) is a compound represented by the following General Formula (II):

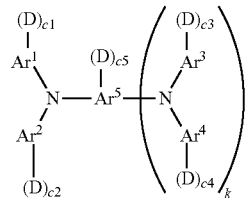
(II)

wherein in General Formula (II), each of $Ar^1$ to $Ar^4$ independently represents a substituted or unsubstituted aryl group, $Ar^5$ represents a substituted or unsubstituted aryl group or a substituted or unsubstituted arylene group, D represents a group represented by General Formula (III), k represents 0 or 1, each of c1 to c5 represents an integer of from 0 to 2, and at least one of c1 to c5 is not 0:

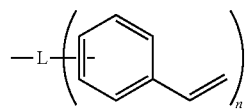
(III)

wherein in General Formula (III), L represents a linking group having a valency of (n+1) that is formed by combining two or more kinds selected from the group consisting of an alkylene group, —C═C— (an alkenylene group), —C(═O)—, —N(R)—, —O—, and —S—, R represents a hydrogen atom, an alkyl group, an aryl group, or an aralkyl group, and n represents an integer of from 2 to 3.

10. The electrophotographic photoreceptor according to claim 8,
wherein the following partial structure in the compound represented by General Formula (I) is a group represented by the following General Formula (IV-1) or a group represented by the following General Formula (IV-2):

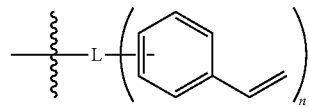

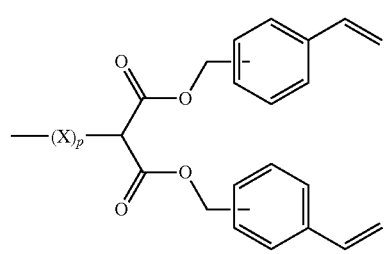
(IV-1)

-continued

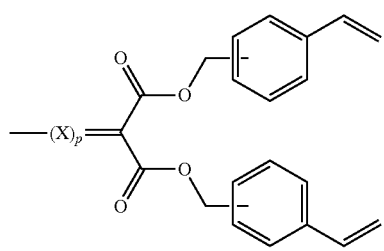

(IV-2)

wherein in General Formulae (IV-1) and (IV-2), X represents a divalent group, and p represents 0 or 1, and the wavy line in the above partial structure represents a site binding to the charge transporting subunit represented by F.

11. The electrophotographic photoreceptor according to claim 8,
wherein the following partial structure in the compound represented by General Formula (I) is a group represented by the following General Formula (V-1) or a group represented by the following General Formula (V-2):

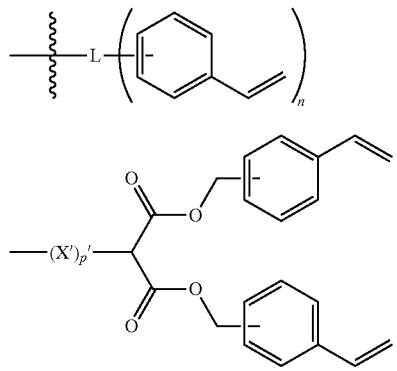

(V-1)

-continued

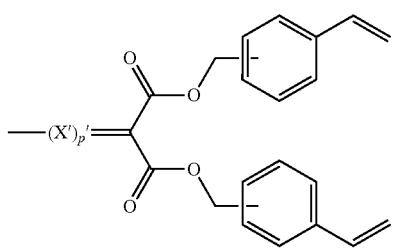

(V-2)

wherein in General Formulae (V-1) and (V-2), X' represents a divalent group, and p' represents 0 or 1, and the wavy line in the above partial structure represents a site binding to the charge transporting subunit represented by F.

12. The electrophotographic photoreceptor according to claim 8, comprising the charge transporting layer as an outermost surface layer.

13. The electrophotographic photoreceptor according to claim 8,
wherein the charge transporting layer further contains a thermal radical generator or a derivative thereof.

14. A process cartridge comprising the electrophotographic photoreceptor according to claim 8,
wherein the process cartridge is detachable from an image forming apparatus.

15. An image forming apparatus comprising:
the electrophotographic photoreceptor according to claim 8,
a charging device that charges the electrophotographic photoreceptor;
an electrostatic latent image forming unit that forms an electrostatic latent image on the charged electrophotographic photoreceptor;
a developing unit that develops the electrostatic latent image formed on the electrophotographic photoreceptor by using a toner to form a toner image; and
a transfer unit that transfers the toner image to a transfer medium.

* * * * *